(12) United States Patent
Milz et al.

(10) Patent No.: US 11,033,302 B2
(45) Date of Patent: Jun. 15, 2021

(54) PIVOTING VERTEBRAL PLATE

(71) Applicant: Stryker European Holdings I, LLC, Kalamazoo, MI (US)

(72) Inventors: Bryan D. Milz, Florida, NY (US); Dan Boljonis, Middletown, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 29 days.

(21) Appl. No.: 16/171,469

(22) Filed: Oct. 26, 2018

(65) Prior Publication Data

US 2019/0059956 A1  Feb. 28, 2019

Related U.S. Application Data

(63) Continuation of application No. 14/509,252, filed on Oct. 8, 2014, now Pat. No. 10,143,499.

(Continued)

(51) Int. Cl.
*A61B 17/70* (2006.01)
*A61B 17/17* (2006.01)
(Continued)

(52) U.S. Cl.
CPC .......... *A61B 17/7059* (2013.01); *A61B 17/16* (2013.01); *A61B 17/1757* (2013.01); *A61B 17/7074* (2013.01); *A61B 17/808* (2013.01); *A61B 17/846* (2013.01); *A61B 17/8875* (2013.01); *A61B 17/8888* (2013.01); *A61B 17/92* (2013.01); *A61F 2/447* (2013.01); *A61F 2/4455* (2013.01); *A61B 17/1604* (2013.01);
(Continued)

(58) Field of Classification Search
CPC ............ A61B 17/7059; A61B 17/7074; A61B 17/1757; A61B 17/808; A61B 17/8872; A61B 17/8894; A61B 17/92; A61F 2/4611; A61F 2002/4622; A61F 2002/4624; A61F 2002/4628
See application file for complete search history.

(56) References Cited

U.S. PATENT DOCUMENTS 5,020,519 A  6/1991 Hayes et al.
5,601,553 A  2/1997 Trebing et al.
(Continued)

FOREIGN PATENT DOCUMENTS

FR   2574499 A1   6/1986
WO   2014188280 A2   11/2014

OTHER PUBLICATIONS

DePuy Spine, Aegis, 2007.
(Continued)

*Primary Examiner* — Kevin T Truong
*Assistant Examiner* — Tracy L Kamikawa
(74) *Attorney, Agent, or Firm* — Lerner, David, Littenberg, Krumholz & Mentlik, LLP

(57) ABSTRACT

A surgical system includes an implant having a first attachment mechanism and an insertion instrument having a proximal end, a distal end, and a second attachment mechanism disposed at the distal end for removable connection with the first attachment mechanism. The proximal end of the insertion instrument is pivotable with respect to the implant. The insertion instrument can include an inserter and a guide. A method of using the surgical system is provided.

12 Claims, 36 Drawing Sheets

Related U.S. Application Data

(60) Provisional application No. 61/955,494, filed on Mar. 19, 2014, provisional application No. 61/948,954, filed on Mar. 6, 2014, provisional application No. 61/888,677, filed on Oct. 9, 2013.

(51) Int. Cl.

| | | |
|---|---|---|
| *A61B 17/80* | (2006.01) | |
| *A61F 2/44* | (2006.01) | |
| *A61B 17/00* | (2006.01) | |
| *A61B 17/88* | (2006.01) | |
| *A61F 2/30* | (2006.01) | |
| *A61F 2/46* | (2006.01) | |
| *A61B 17/16* | (2006.01) | |
| *A61B 17/84* | (2006.01) | |
| *A61B 17/92* | (2006.01) | |

(52) U.S. Cl.
CPC ....... *A61B 17/1671* (2013.01); *A61B 17/8894* (2013.01); *A61B 2017/00464* (2013.01); *A61B 2017/00477* (2013.01); *A61F 2/30724* (2013.01); *A61F 2002/30331* (2013.01); *A61F 2002/30375* (2013.01); *A61F 2002/30517* (2013.01); *A61F 2002/30576* (2013.01); *A61F 2002/30578* (2013.01); *A61F 2002/30607* (2013.01); *A61F 2002/30784* (2013.01); *A61F 2002/4615* (2013.01)

(56) References Cited

U.S. PATENT DOCUMENTS

| | | | |
|---|---|---|---|
| 6,102,934 A | 8/2000 | Li | |
| 6,156,037 A | 12/2000 | LeHuec et al. | |
| 6,224,602 B1 | 5/2001 | Hayes | |
| 6,228,085 B1 | 5/2001 | Theken et al. | |
| 6,235,034 B1 | 5/2001 | Bray | |
| 6,319,257 B1 * | 11/2001 | Carignan | A61F 2/4601 606/205 |
| 6,342,057 B1 | 1/2002 | Brace et al. | |
| 6,379,364 B1 | 4/2002 | Brace et al. | |
| 6,503,250 B2 | 1/2003 | Paul | |
| 6,565,571 B1 | 5/2003 | Jackowski et al. | |
| 6,602,255 B1 | 8/2003 | Campbell et al. | |
| 6,602,256 B1 | 8/2003 | Hayes | |
| 6,740,088 B1 | 5/2004 | Kozak et al. | |
| 6,793,658 B2 | 9/2004 | LeHuec et al. | |
| 6,830,574 B2 | 12/2004 | Heckele et al. | |
| 6,884,242 B2 | 4/2005 | LeHuec et al. | |
| 6,960,216 B2 | 11/2005 | Kolb et al. | |
| 6,989,012 B2 | 1/2006 | LeHuec et al. | |
| 7,011,665 B2 | 3/2006 | Null et al. | |
| 7,081,119 B2 | 7/2006 | Stihl | |
| 7,303,564 B2 | 12/2007 | Freid et al. | |
| 7,341,587 B2 | 3/2008 | Molz, IV et al. | |
| 7,416,553 B2 | 8/2008 | Patel et al. | |
| 7,572,276 B2 | 8/2009 | Lim et al. | |
| 7,604,638 B2 | 10/2009 | Jacene et al. | |
| 7,648,506 B2 | 1/2010 | McCord et al. | |
| 7,648,507 B2 * | 1/2010 | Techiera | A61B 17/7002 606/86 A |
| 7,678,113 B2 | 3/2010 | Melkent | |
| 7,763,029 B2 * | 7/2010 | Rathbun | A61B 17/1728 606/280 |
| 7,776,047 B2 | 8/2010 | Fanger et al. | |
| 7,909,829 B2 | 3/2011 | Patel et al. | |
| 7,909,848 B2 | 3/2011 | Patel et al. | |
| 7,935,123 B2 | 5/2011 | Fanger et al. | |
| 7,988,695 B2 | 8/2011 | Dye | |
| 8,097,027 B2 | 1/2012 | Lim et al. | |
| 8,109,934 B2 | 2/2012 | Guenther et al. | |
| 8,118,872 B2 | 2/2012 | Trudeau et al. | |
| 8,123,757 B2 | 2/2012 | Zalenski et al. | |
| 8,172,854 B2 * | 5/2012 | Blain | A61B 17/1728 606/86 A |
| 8,282,642 B2 | 10/2012 | McClintock et al. | |
| 8,343,160 B2 | 1/2013 | Techiera et al. | |
| 8,394,107 B2 | 3/2013 | Fanger et al. | |
| 8,449,582 B2 | 5/2013 | McLain | |
| 10,022,245 B2 * | 7/2018 | Frasier | A61F 2/442 |
| 2002/0045896 A1 | 4/2002 | Michelson | |
| 2003/0225409 A1 | 12/2003 | Freid et al. | |
| 2005/0038444 A1 | 2/2005 | Binder et al. | |
| 2005/0090824 A1 * | 4/2005 | Shluzas | A61B 17/7083 606/60 |
| 2005/0131419 A1 | 6/2005 | McCord et al. | |
| 2005/0131420 A1 | 6/2005 | Techiera et al. | |
| 2006/0155283 A1 * | 7/2006 | Doherty | A61B 17/1615 606/915 |
| 2006/0189997 A1 | 8/2006 | Guenther et al. | |
| 2006/0235426 A1 | 10/2006 | Lim et al. | |
| 2007/0162138 A1 * | 7/2007 | Heinz | A61F 2/4611 623/17.16 |
| 2007/0167953 A1 | 7/2007 | Prien et al. | |
| 2007/0233150 A1 | 10/2007 | Blain et al. | |
| 2008/0097443 A1 | 4/2008 | Campbell | |
| 2008/0306550 A1 | 12/2008 | Matityahu | |
| 2009/0024132 A1 | 1/2009 | Blain et al. | |
| 2009/0048604 A1 | 2/2009 | Milz et al. | |
| 2009/0131988 A1 | 5/2009 | Bush, Jr. et al. | |
| 2010/0100131 A1 | 4/2010 | Wallenstein | |
| 2010/0312345 A1 * | 12/2010 | Duffield | A61F 2/4465 623/17.16 |
| 2011/0015685 A1 | 1/2011 | Fanger et al. | |
| 2011/0106259 A1 | 5/2011 | Lindenmann et al. | |
| 2011/0172776 A1 | 7/2011 | Warnick et al. | |
| 2012/0191141 A1 | 7/2012 | Costabile | |
| 2013/0023889 A1 | 1/2013 | Blain et al. | |
| 2013/0060291 A1 | 3/2013 | Petersheim | |
| 2013/0060337 A1 | 3/2013 | Petersheim et al. | |
| 2013/0096626 A1 | 4/2013 | Techiera et al. | |
| 2013/0123793 A1 | 5/2013 | Kehres et al. | |
| 2013/0190825 A1 * | 7/2013 | Perrow | A61B 17/8042 606/281 |
| 2013/0211462 A1 | 8/2013 | Walker | |

OTHER PUBLICATIONS

Extended European Search Report for Application No. 14188062.5 dated Apr. 1, 2015.
Medtronic Sofamor Danek, Xantus, 2003.
Medtronic, Pyramid, 2002.
NuVasive, XLP, 2011.
Synthes, Antegra-T Instruments and Impants, 2008.
Synthes, ATB Anterior Tension Band Plate, Nov. 2010.
Synthes, Oracle Plate System, 2009.

\* cited by examiner

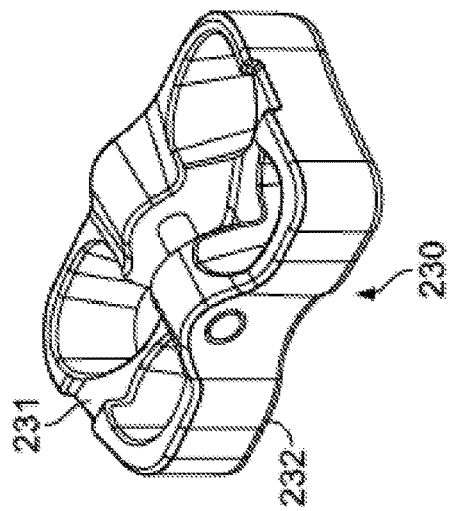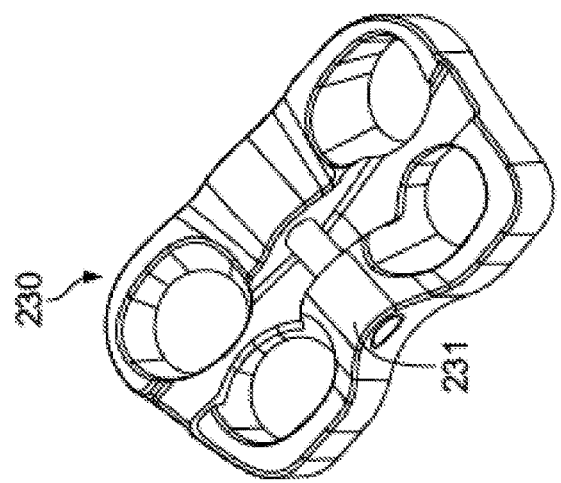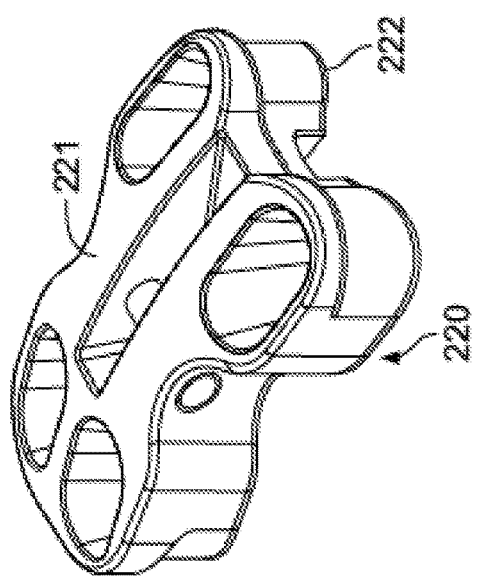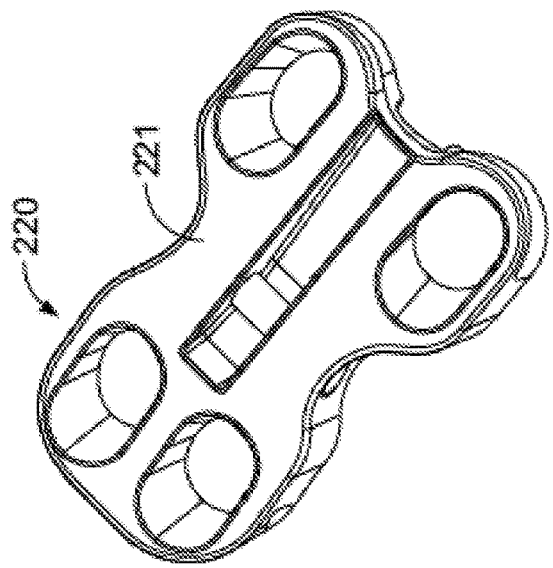

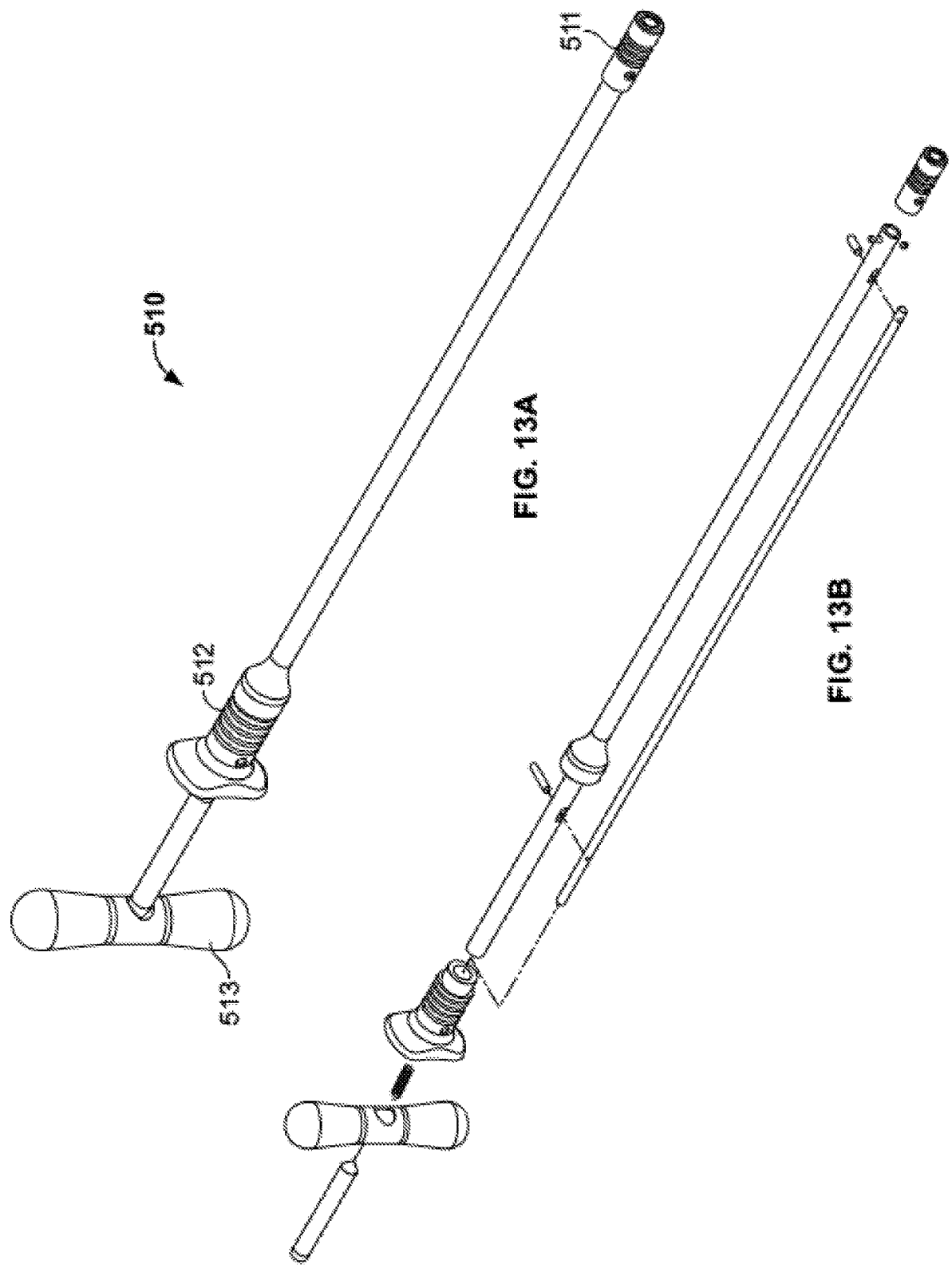

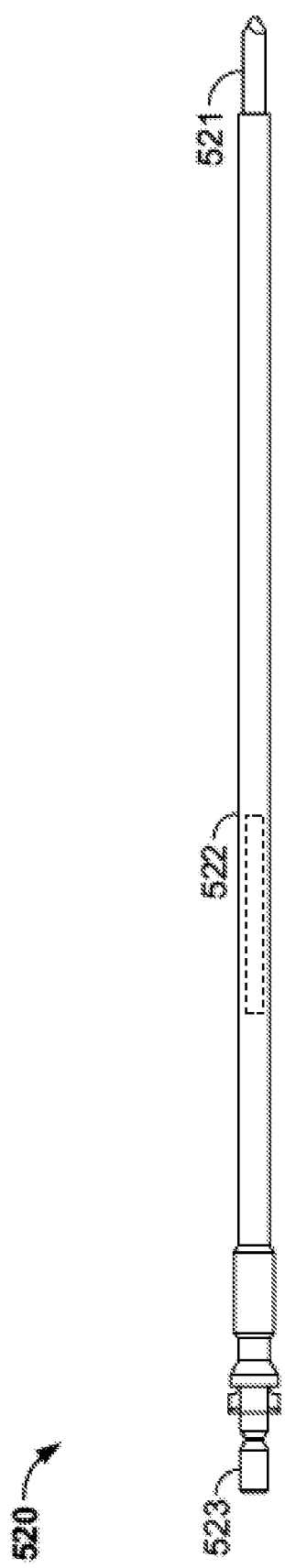
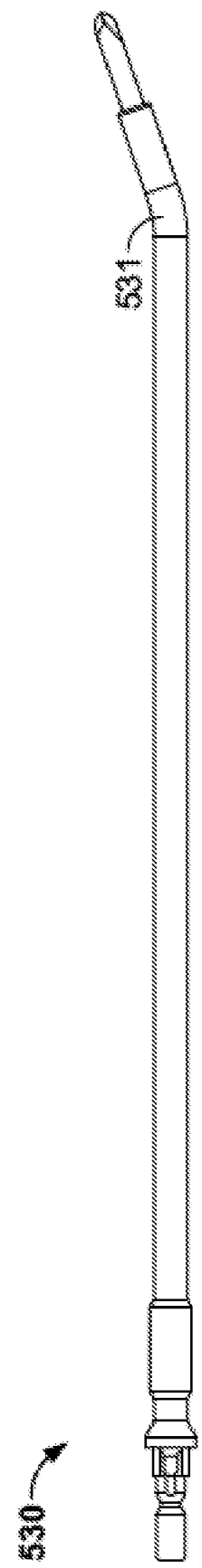
FIG. 14A
FIG. 14B

PIVOTING VERTEBRAL PLATE

CROSS-REFERENCE TO RELATED APPLICATIONS

The present application is a continuation of U.S. patent application Ser. No. 14/509,252, filed Oct. 8, 2014, which claims the benefit of the filing dates of U.S. Provisional Patent Application No. 61/888,677 filed Oct. 9, 2013, U.S. Provisional Patent Application No. 61/948,954 filed Mar. 6, 2014, and U.S. Provisional Patent Application No. 61/955,494 filed Mar. 19, 2014, the disclosures of which are hereby incorporated herein by reference.

BACKGROUND OF THE INVENTION

The present invention relates to vertebral plates and methods of implanting such plates. More particularly, the present invention relates to vertebral plates, kits of different vertebral plates, guides configured to be used with such plates, and an insertion instrument for manipulating the guide and plate, as well as the associated methods of insertion.

Back pain can be caused by many different things, including any one of several problems that affect the intervertebral discs of the spine. These disc problems include, for instance, degeneration, bulging, herniation, thinning of a disc, and abnormal movement. Pain is generally attributable to friction or pressure that inevitably occurs when one adjacent vertebra exerts uneven pressure or when both adjacent vertebrae exert such pressure on the disc. Oftentimes, disc problems lead to the vertebrae impinging on one of the very many nerves located in the spinal column.

One surgical method utilized to correct such disc problems is a fusion procedure where a surgeon fuses together adjacent vertebrae in single or multiple levels. Traditional interbody fusion (IF) techniques generally involve removing at least a portion of the troublesome disc from the patient, inserting a spinal implant into the space, and adding bone graft material into the interbody space between the vertebrae adjacent to the disc. A further step in a fusion procedure can include securing a vertebral plate against the adjacent vertebrae across the space to hold the graft material in place and to support the vertebrae while solid bone mass forms therebetween.

The many variations of the IF technique may be performed through open surgeries or by performing a more minimally invasive surgical (MIS) procedure. In MIS procedures, portals are used to access the locations in the patient's body, which cause less trauma to the adjacent tissue, reduces recovery time and pain, and may be performed in some cases under only local anesthesia. Surgeons may use tubes, portals, channels, and retraction-type instruments to work in the working channel for MIS procedures. Among the types of instruments used are insertion instruments that help place the vertebral plate into its proper position adjacent the vertebral bodies.

As incisions for MIS procedures are generally very small, there is a need for instruments that are easier to utilize through a portal in a small working channel, perform their function once at the site, and interact with other instruments if need be.

In the insertion of vertebral plates, many current products utilize static or rigid connections between an insertion instrument and a vertebral plate. Such rigid connections limit the ability of the the instrument to manipulate the vertebral plate toward and onto the vertebrae.

There is therefore a need for a vertebral plate insertion system and method of using same that can be utilized through a small working channel and that can allow for greater manipulation and autonomy during the procedure. There is also a need for vertebral plates that are more particularly configured and tailored to be used with different portions of the vertebral column, and kits containing multiple of such different plates.

SUMMARY OF THE INVENTION

A first aspect of the present invention is a surgical system including an implant having a first attachment mechanism, and an insertion instrument having a proximal end, a distal end, and a second attachment mechanism disposed at the distal end for removable connection with the first attachment mechanism, wherein the proximal end of the insertion instrument is pivotable with respect to the implant.

In accordance with other embodiments of the first aspect, the insertion instrument may include an inserter and a guide, with the guide including the second attachment mechanism for connection with the first attachment mechanism. The inserter may be pivotally and removably connected with the guide. The guide may include a pin and the inserter may include two clips configured to pivotally and removably grasp the pin. The inserter may include a sleeve movable from an unlocked position in which the sleeve is disengaged from the clips and the clips can move apart from one another to a locked position in which the sleeve overlaps at least a portion of the clips to at least partially prevent the clips from moving apart from one another. The second attachment mechanism may be a male feature and the first attachment mechanism may be a female feature. The male and female features may be further secured with a ball-detent feature therebetween. The male feature may be a split shank and the female feature may be an aperture configured to receive the split shank. The guide may be configured to be dedicated to a single configuration of the implant. The guide may be configured to be attachable to multiple different configurations of the implant. The guide may include an aperture configured to align with a screw hole of the implant. The system may further include a second insertion instrument having a proximal end, a distal end, and a third attachment mechanism disposed at the distal end for connection with the first attachment mechanism, the second insertion instrument being an inserter directly engageable with the implant. The first attachment mechanism may be configured to connect with both the second attachment mechanism and the third attachment mechanism.

The insertion instrument may be an inserter directly engageable with the implant. The insertion instrument may include a pivoting joint adjacent the distal end thereof. The second attachment mechanism may be a male feature and the first attachment mechanism may be a female feature. The male and female features may be further secured with a ball-detent feature therebetween. The distal end of the insertion instrument may define a longitudinal axis, and the male feature may be rotatable about the longitudinal axis and may have a non-circular cross-section in a plane perpendicular to the longitudinal axis. The male feature may be a split shank and the female feature may be an aperture configured to receive the split shank.

The proximal end of the insertion instrument may include a quick connect attachment for interfacing with a handle. The implant may have a first configuration, and the system may further include one or more additional implants each having a configuration different from the first configuration.

The system may further include a screw for insertion through a screw hole of the implant. The system may further include at least one tool selected from the group consisting of: a fixation pin, a fixation pin inserter, a straight awl, an angled awl, a screwdriver, a self-retaining screwdriver, a finishing screwdriver, and a flexible screwdriver.

A second aspect of the present invention is a method of using a surgical system including the steps of removably attaching an insertion instrument to an implant, manipulating the insertion instrument to guide the implant, and pivoting a proximal end of the insertion instrument with respect to the implant to guide the implant into its final positioning.

In accordance with other embodiments of the second aspect, the insertion instrument may include an inserter and a guide, and the step of removably attaching may include removably attaching the guide to the implant and removably attaching the inserter to the guide. The method may further include the step of inserting a screw through a screw hole of the implant. The step of inserting the screw may include inserting the screw through an aperture of the guide aligned with the screw hole of the implant. The method may further include the step of removing the insertion instrument from the guide with the implant at least temporarily anchored to the adjacent vertebra. The step of pivoting may include pivoting the inserter with respect to the guide about a junction between the inserter and the guide. The step of removably attaching may include removably attaching two clips of the insertion instrument to pivotally grasp a pin of the guide. The method may further include the step of moving a sleeve of the insertion instrument from an unlocked position in which the sleeve is disengaged from the clips and the clips can move apart from one another to a locked position in which the sleeve overlaps at least a portion of the clips to at least partially prevent the clips from moving apart from one another.

The step of removably attaching may include removably attaching the insertion instrument directly to the implant. The method may further include the step of removing the insertion instrument from the guide with the implant at least temporarily anchored to the adjacent vertebra. The method may further include the step of inserting a screw through a screw hole of the implant. The step of pivoting may include pivoting the proximal end of the insertion instrument with respect to a distal end of the insertion instrument about a pivoting joint of the insertion instrument.

The method may further include the step of rotating the insertion instrument with respect to the implant by rotating an engagement feature at a distal end of the instrument about a longitudinal axis defined by the distal end. The method may further include the step of selecting the implant from a group of differently configured implants. The method may further include the step of inserting a screw through a screw hole of the implant by using a self-retaining screwdriver. The method may further include the step of inserting a screw through a screw hole of the implant by using a finishing screwdriver. The method may further include the step of inserting a screw through a screw hole of the implant by using a flexible screwdriver. The method may further include the step of attaching a handle to a quick connect attachment at a proximal end of the insertion instrument. The method may further include the step of inserting a fixation pin through a screw hole of the implant to temporarily anchor the implant to the adjacent vertebra. The method may further include the step of creating a pilot hole in the vertebra adjacent a screw hole of the implant by using an awl. The step of manipulating may include manipulating the insertion instrument to guide the implant through a working channel.

A third aspect of the present invention is a method of using a surgical system including the steps of selecting one of two instrument systems, a first of the instrument systems including an inserter and a guide engageable with an implant, and a second of the insertion systems including an inserter directly engageable with an implant, removably attaching the selected insertion instrument to an implant, manipulating the insertion instrument to guide the implant, and pivoting a proximal end of the insertion instrument with respect to the implant to guide the implant into its final positioning.

A fourth aspect of the present invention is an anterior vertebral plate kit including a universal anterior vertebral plate, a sacral anterior vertebral plate, a buttress anterior vertebral plate, and at least one screw for use with one of the plates. In accordance with other embodiments of the fourth aspect, the kit further includes instrumentation for insertion of the plates and screw.

A fifth aspect of the present invention is an anterior vertebral plate kit including a plurality of universal anterior vertebral plates of different sizes, a plurality of sacral anterior vertebral plates of different sizes, a plurality of buttress anterior vertebral plates of different sizes, and at least one screw for use with one of the plates. In accordance with other embodiments of the fifth aspect, the kit further includes instrumentation for insertion of the plates and screw.

A sixth aspect of the present invention is a lateral vertebral plate kit including a lateral vertebral plate having four screw holes, a lateral vertebral plate having two screw holes, and at least one screw for use with one of the plates. In accordance with other embodiments of the sixth aspect, the kit further includes instrumentation for insertion of the plates and screw.

A seventh aspect of the present invention is a lateral vertebral plate kit including a plurality of lateral vertebral plates having four screw holes of different sizes, a plurality of lateral vertebral plates having two screw holes of different sizes, and at least one screw for use with one of the plates. In accordance with other embodiments of the seventh aspect, the kit further includes instrumentation for insertion of the plates and screw.

An eighth aspect of the present invention is an instrument kit including a first insertion instrument including an inserter having a proximal end, and a guide having an attachment mechanism for removable connection with an attachment mechanism of an implant, wherein the proximal end of the inserter is pivotable with respect to the implant, and a second insertion instrument including a proximal end, a distal end, and an attachment mechanism disposed at the distal end thereof for removable connection with the attachment mechanism of the implant, wherein the proximal end of the second insertion instrument is pivotable with respect to the implant, and wherein the second insertion instrument is an inserter directly engageable with the implant.

A ninth aspect of the present invention is a system including the anterior vertebral plate kit of the fifth aspect and the instrument kit of the eighth aspect.

A tenth aspect of the present invention is a system including the lateral vertebral plate kit of the seventh aspect and the instrument kit the eighth aspect.

An eleventh aspect of the present invention is a system including the anterior vertebral plate kit of the fifth aspect, the lateral vertebral plate kit of the seventh aspect, and the instrument kit the eighth aspect.

A twelfth aspect of the present invention is a surgical system including an intervertebral implant for insertion into an intervertebral disc space between first and second vertebral bodies, a vertebral plate for attachment to at least one of the first and second vertebral bodies, and a spacer configured to be coupled to the vertebral plate and to extend at least partially into the intervertebral disc space.

In accordance with other embodiments of the twelfth aspect, the spacer may include an implant contacting surface having a V shape. The spacer may include a plate contacting surface and an engagement member extending therefrom for interfacing with the plate. The engagement member may be dimensioned to be press-fit into an aperture in the plate. The engagement member may have an oval cross-section. The engagement member may extend perpendicularly from the plate contacting surface. A contour of the plate contacting surface may correspond to a profile of plate.

When the spacer is coupled to the vertebral plate and in its implanted position, the spacer may not be fixedly connected with the intervertebral implant. When the spacer is coupled to the vertebral plate and in its implanted position, the spacer may be configured to prevent the intervertebral implant from moving substantially away from its implanted location. When the spacer is coupled to the vertebral plate and in its implanted position, the spacer may not contact the intervertebral implant. The spacer may have a thickness extending between an implant contacting surface and a plate contacting surface thereof, and the system may further include one or more additional spacers, wherein each spacer has a different thickness.

A thirteenth aspect of the present invention is a surgical system including a vertebral plate for attachment to a vertebral body, and a spacer configured to be coupled to the vertebral plate and to extend at least partially into an intervertebral disc space adjacent the vertebral body.

A fourteenth aspect of the present invention is a surgical system including an intervertebral implant for insertion into an intervertebral disc space between first and second vertebral bodies, and a spacer configured to be coupled to a vertebral plate that is for attachment to at least one of the first and second vertebral bodies, the spacer configured to extend at least partially into the intervertebral disc space.

A fifteenth aspect of the present invention is a surgical spacer including a body having an implant contacting surface, a plate contacting surface, and an engagement member extending from the plate contacting surface for coupling with a vertebral plate that is for attachment to a vertebral body. The implant contacting surface has a V shape for interfacing with an intervertebral implant inserted into an intervertebral disc space adjacent the vertebral body.

In accordance with other embodiments of the fifteenth aspect, the engagement member may have an oval cross-section. The engagement member may extend perpendicularly from the plate contacting surface. A kit may include two or more of the aforementioned spacers, wherein each spacer has a different thickness extending between the implant contacting surface and the plate contacting surface thereof.

A sixteenth aspect of the present invention is a method of using a surgical system including the steps of inserting an intervertebral implant into the intervertebral disc space, coupling a spacer to a vertebral plate, and attaching the vertebral plate to a vertebral body such that the spacer extends at least partially into an intervertebral disc space adjacent the vertebral body, wherein the spacer is configured to prevent the intervertebral implant from moving substantially away from its implanted location.

In accordance with other embodiments of the sixteenth aspect, the step of coupling may include press-fitting an engagement member of the spacer into a corresponding aperture of the plate. After the step of attaching the vertebral plate to the vertebral body, the spacer may not contact the intervertebral implant. The method may further include providing a kit of two or more spacers having different thicknesses, and selecting one of the spacers to be coupled with the plate based on its thickness.

BRIEF DESCRIPTION OF THE DRAWINGS

A more complete appreciation of the subject matter of the present invention and the various advantages thereof can be realized by reference to the following detailed description in which reference is made to the accompanying drawings, in which:

FIGS. 4A and 4B are perspective views of a screw guide in accordance with another embodiment of the present invention.

FIGS. 4C and 4D are perspective views of a screw guide in accordance with another embodiment of the present invention.

FIGS. 13A and 13B are perspective and exploded views, respectively, of a fixation pin inserter in accordance with an embodiment of the present invention.

FIG. 14A is an elevational side view of a straight awl in accordance with an embodiment of the present invention.

FIG. 14B is an elevational side view of an angled awl in accordance with an embodiment of the present invention.

DETAILED DESCRIPTION

As used herein, when referring to bones or other parts of the body, the term "proximal" means closer to the user and the term "distal" means more distant from the user.

Figures 1A, 1B:
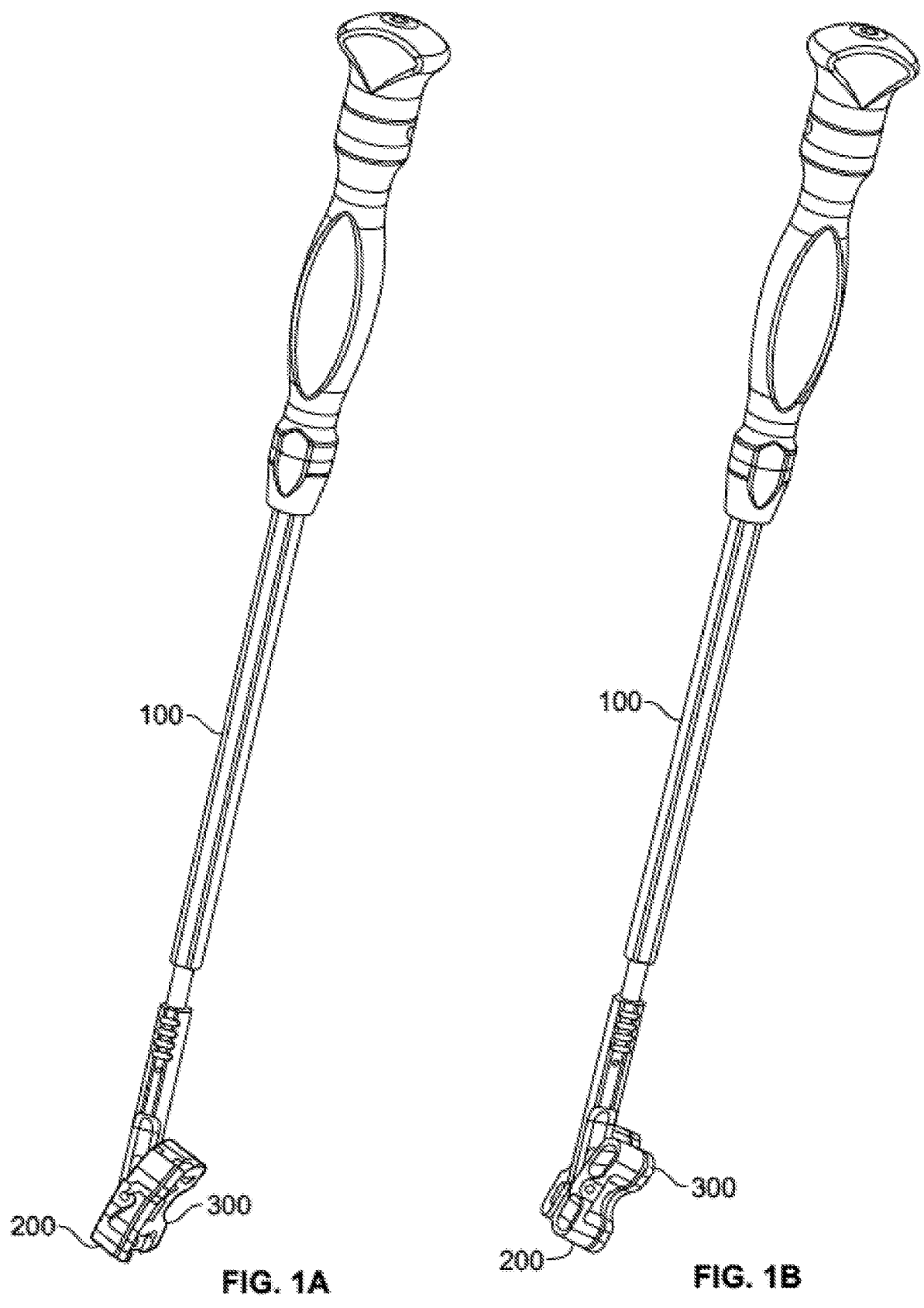
FIGS. 1A and 1B are perspective views of an insertion instrument assembled with a screw guide and a vertebral plate in accordance with an embodiment of the present invention.
Figure 2:
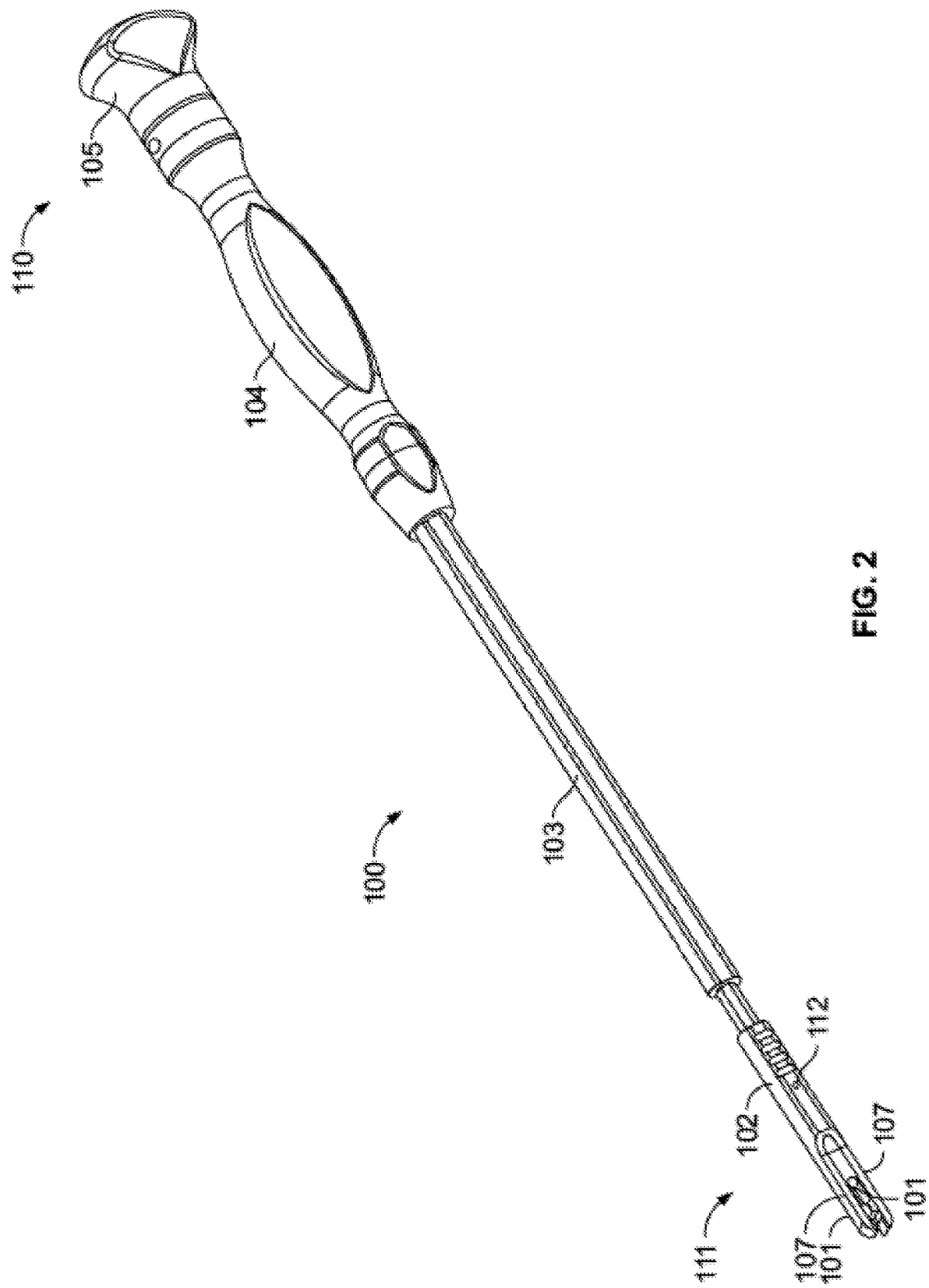
FIG. 2 is a perspective view of the insertion instrument shown in FIG. 1.

In an embodiment of the present invention as shown in FIG. 1A and FIG. 1B, an insertion instrument 100 is removeably engaged with a screw guide 200, which in turn is removeably engaged with a vertebral plate 300. As shown in FIG. 2, instrument 100 has a proximal end 110 and a distal end 111, at which two clips 101 are located. Clips 101 may be any type of spring or locking clips that are elastic or elastically connected with the other components of instrument 100 so that clips 101 can flex toward and away from one another. Clips 101 are fixedly connected to an outer shaft 103, which at its other end is fixedly connected to a handle 104.

A locking sleeve 102 is provided at distal end 111 of instrument 100. Locking sleeve 102 includes fingers 107 that overlap clips 101, respectively. Fingers 107 also define openings at either side of the distal end of locking sleeve 102. Compared with clips 101, fingers 107 are substantially inelastically connected with one another. In this way, when fingers 107 are disposed to overlap clips 101, clips 101 are substantially prevented from separating further apart from one another. That is, locking sleeve 102 acts as a boundary limiting the extent to which clips 101 can flex apart.

Figure 10:
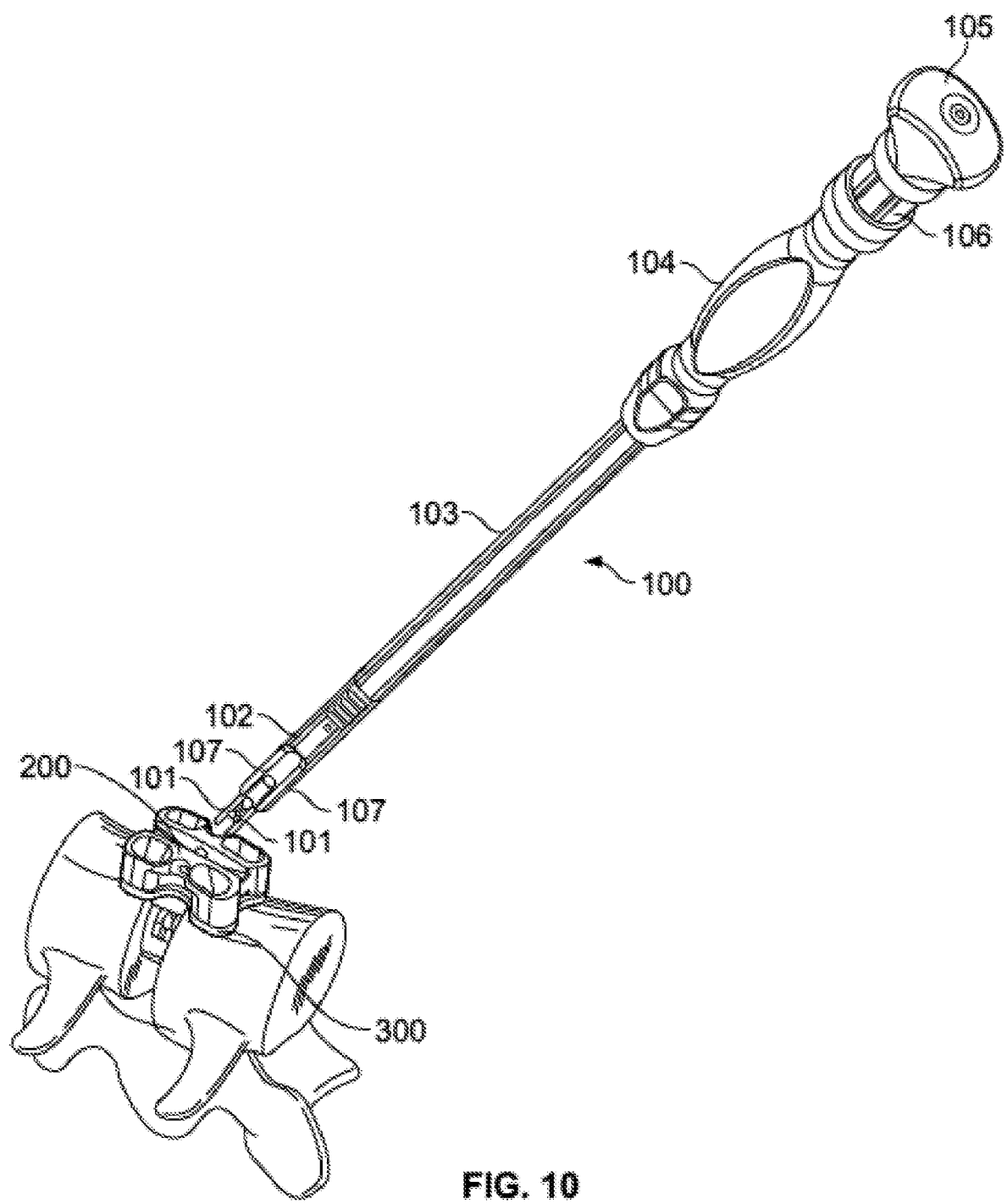

A locking knob 105 is disposed at proximal end 110 of the instrument 100. The straight, slim profile of handle 104 and knob 105 improves the maneuverability of the instrument 100 and increases the amount of space adjacent instrument 100, which space is beneficial to the surgeon so that visibility is enhanced during a procedure. Locking knob 105 is connected to locking sleeve 102 by an inner shaft 106, which is visible at proximal end 110 in the unlocked position as depicted in FIG. 10. Most of inner shaft 106 is enclosed by outer shaft 103. Knob 105 is connected to sleeve 102 via inner shaft 106, such that movement of knob 105 in the proximal-distal direction also moves sleeve 102 in such direction. Sleeve 102 is connected to inner shaft 106 via a cross pin 112.

The instrument 100 is in the fully locked position when locking knob 105 is located distally toward handle 104, making contact with the proximal end of handle 104 as depicted in FIG. 2. As locking knob 105 is pushed toward handle 104 to this position, inner shaft 106 is pushed through outer shaft 103. As a result, locking sleeve 102 is pushed distally until fingers 107 are fully disposed over clips 101 to maintain clips 101 in a closed position, i.e. to prevent clips 101 from flexing away from one another. In this position, clips 101 can be housed in their entirety within the distal portion of sleeve 102. This not only keeps the clips 101 closed, but also protects them from damage and stabilizes them so that they move with the instrument as one unit. In other other embodiments, the fingers of the locking sleeve may hold the clips closed by only housing them partially within the sleeve. As shown in FIG. 2, the sides of clips 101 are visible through the openings on the sides of locking sleeve 102, allowing room for the object with which clips 101 are connected.

The instrument 100 is in the fully unlocked position when locking knob 105 is located proximally away from handle 104. As locking knob 105 moves away from handle 104 to this position, inner shaft 106 is pulled through outer shaft 103, resulting in clips 101 being exposed beneath fingers 107 of sleeve 102. Such exposure permits clips 101 to flex apart from one another so that an element can be placed therebetween.

Instrument 100 includes a ball-detent feature that can assist in maintaining instrument 100 in either its locked or unlocked position. The ball-detent feature can be located at any interface between the knob 105/inner shaft 106/sleeve 102 construct and the handle 104/outer shaft 103/clips 101 construct, which constructs are moveable with respect to one another. The force required to engage and disengage the ball-detent feature is minimal, and the feature provides enough engagement force to hold and maintain handle 104 at a particular location with respect to locking knob 105 during a procedure. The feature also allows for a fluid motion when switching from one position to the other, which can be done by a single hand of a user using, for example, only the user's thumb.

Screw guide 200, depicted in FIGS. 3A-3D, has a proximal surface 201, a distal surface 202, and a plurality of apertures 203. Apertures 203 are configured to be aligned with screw holes of a mating vertebral plate, such as plate 300, and have an internal angulation which allows for screws to be inserted at angles between approximately 0 and 25 degrees relative to an axis generally normal to proximal surface 201. In other embodiments, the apertures 203 may provide for greater or lesser ranges of angulation. The thickness of guide 200 between proximal surface 201 and distal surface 202 can be in the range from 8 to 10 mm, though other values may be used.

Figure 3B:
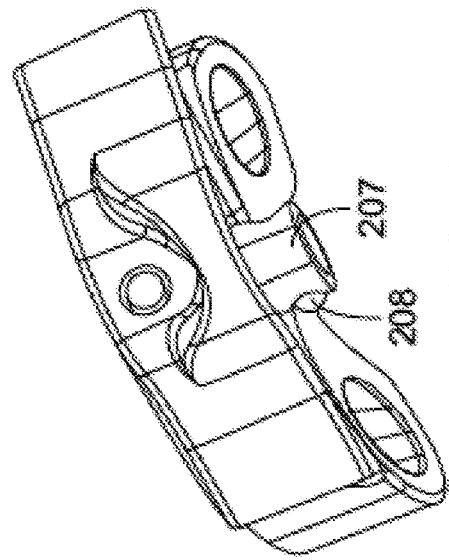
FIGS. 3A and 3B are perspective views of the screw guide shown in FIG. 1.
Figure 3D:
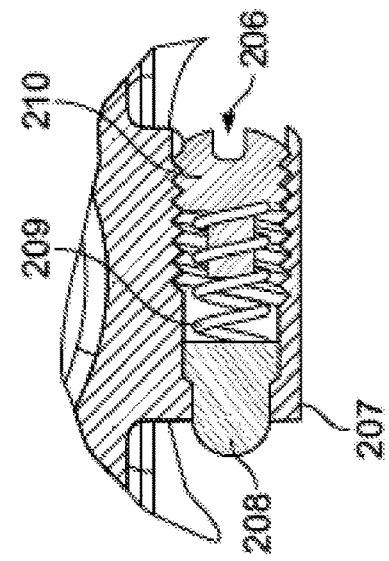
FIG. 3D is a cross-sectional view of the retaining mechanism of the screw guide shown in FIG. 3C.
Figure 3A:
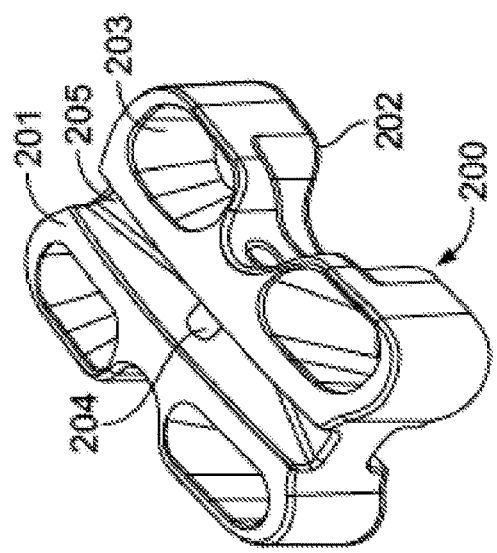
Figure 3C:
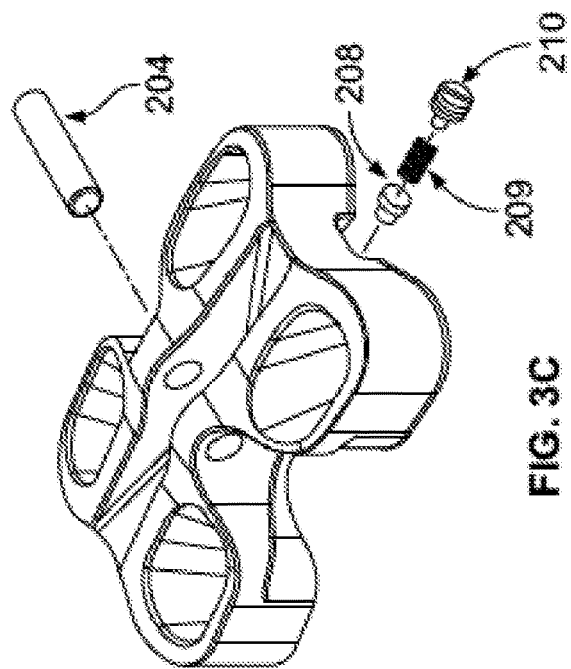
FIG. 3C is an exploded view of the screw guide shown in FIG. 1 showing a pivot pin and a retaining mechanism.

Screw guide 200 further includes a channel 205 accessible at proximal surface 201 and a pivot pin 204 disposed to cross through channel 205. As shown in FIG. 3C, pivot pin 204 can be provided separately and assembled onto guide 200 by inserting it through a hole machined through a side of guide 200. Pivot pin 204 is positioned and configured to be engaged by clips 101 of instrument 100. Channel 205 is configured so that instrument 100, when engaged with guide 200, can pivot freely with minimal obstruction about the axis defined by pivot pin 204.

Figure 5A:
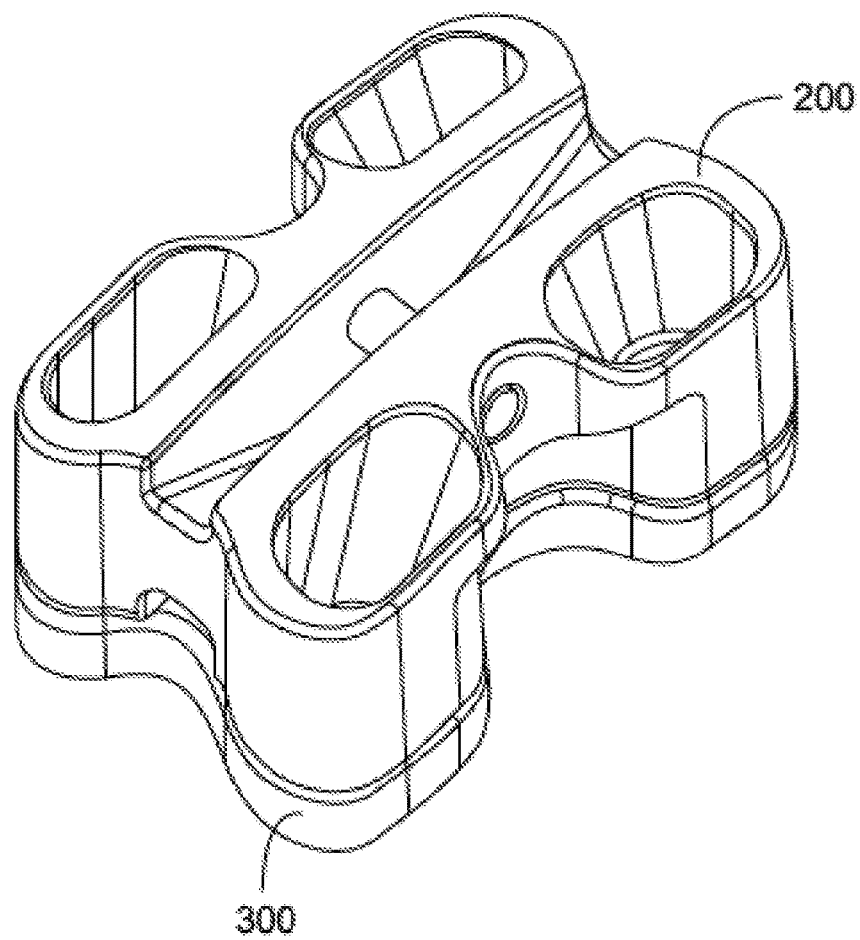
FIGS. 5A and 5B are perspective views of the screw guide assembled with the vertebral plate, both as shown in FIG. 1.
Figure 5B:
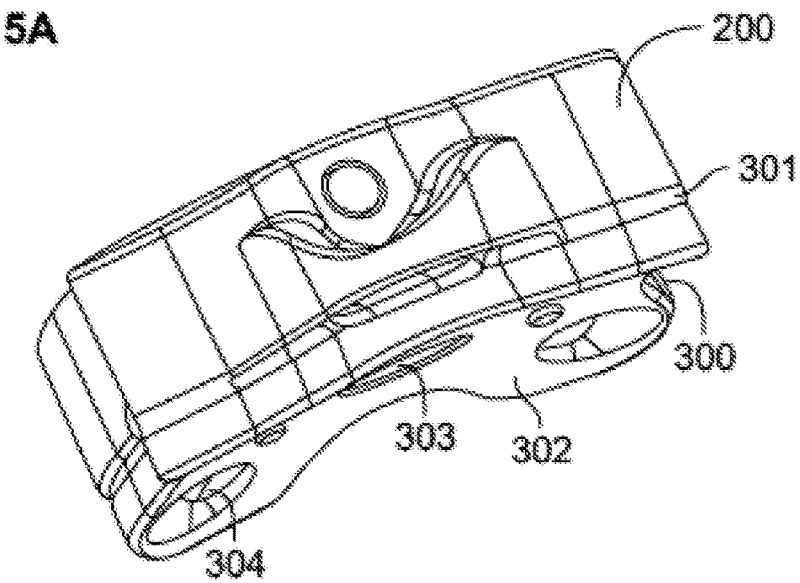
Figure 5C:
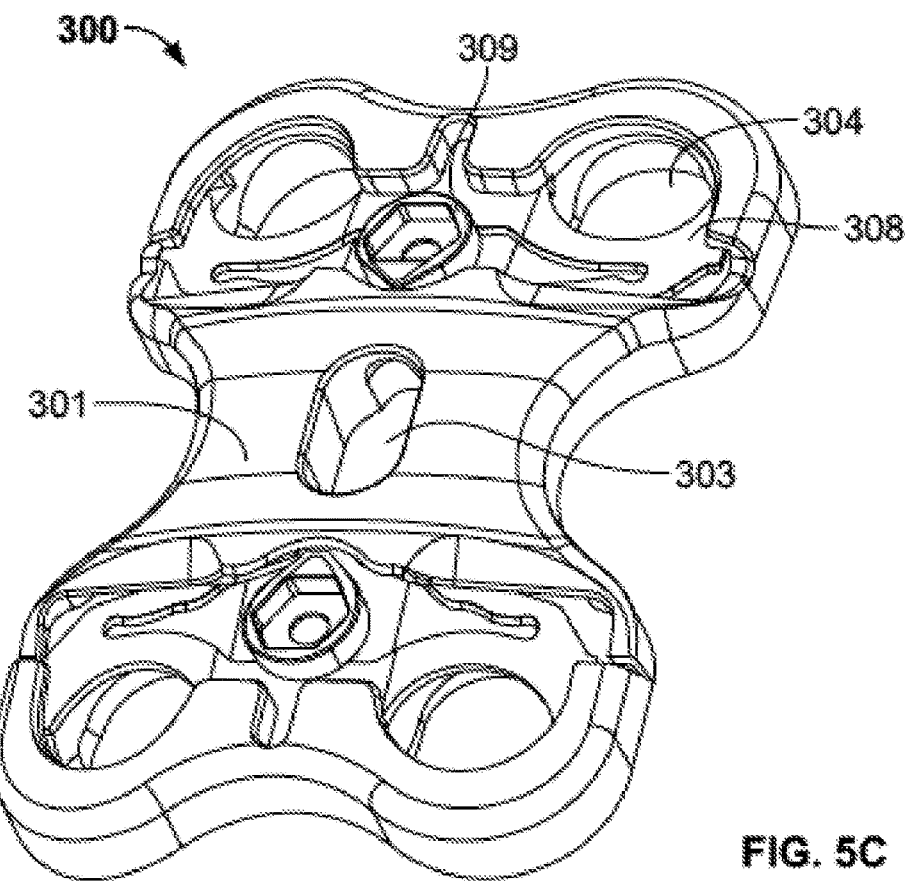
FIGS. 5C and 5D are perspective views of the vertebral plate shown in FIGS. 5A and 5B.

Extending from distal surface 202 of guide 200 is an antirotation (or male) feature 207, which includes a ball-detent feature 206 to assist in holding implant 300 in its removable engagement with guide 200, as shown in FIGS. 5A and 5B. Ball-detent feature 206 includes a bearing 208, a spring 209, and a set screw 210 housed within a passage of antirotation feature 207, as depicted in FIGS. 3C and 3D. The bearing 208 is inserted into the passage within feature 207 and is configured so that it partially protrudes from but cannot fully exit from the other end of the passage. To hold bearing 208 in place in the passage, spring 209 and set screw 210 are also inserted into the passage, with set screw 210 pushing on spring 209 which in turn pushes on bearing 208. Set screw 210 is disposed within a threaded portion of the passage and is preferably inserted so that it does not protrude from the end of passage at which it is inserted to ensure no interference with plate 300. Set screw 210 can be adjusted to provide a fixed distance between it and bearing 208 in which space spring 209 is disposed. That space together with the configuration of spring 209 dictates the external force necessary to push bearing 208 back into the passage. As explained below, feature 207 facilitates easy attachment to and removal from plate 300. There is a volume of material removed from the distal surface of guide 200, shown most clearly in FIG. 3C, so as to allow for manufacturability and assembly of the ball-detent feature. The recessed area of distal surface 202 around male feature 207 allows for easy accessibility to the male feature 207 by plate 300.

Holes 201 may be arranged in any configuration. A first hypothetical medial-lateral plane of a vertical orientation containing the axis of pin 204 divides holes 201 into two holes 201 at one end and two holes 201 at the other. These pairs of holes 201 may be symmetric, as shown in FIG. 3A, may be asymmetric, or any combination thereof. Likewise, a second hypothetical superior-inferior plane of a vertical orientation perpendicular to the axis of pin 204 divides holes 201 into two holes 201 on one side and two holes 201 on the other side. These pairs of holes 201 may be symmetric, as shown in FIG. 3A, may be asymmetric, or any combination thereof.

As shown in FIGS. 4A-4D, guides 220, 230 are alternative embodiments to guide 200 having different dimensions and configurations as compared to guide 200 to demonstrate the various types of guides that can be utilized in accordance with the present invention. Guide 220 includes a proximal surface 221, a distal surface 222, and has two apertures closer together at one end than at the other, with the groove being disposed nearer one end than the other. Guide 220 is configured for use with a plate such as plate 2600, described below. Guide 230 includes a proximal surface 231, a distal surface 232, and has two apertures closer at one side than at the other. Guide 230 is configured for use with a plate such as plate 2700, described below. Many other configurations can be used according to need and according to a particular configuration of a vertebral plate, as will be explained further below. Any of the grooves of the described embodiments may be symmetric or asymmetric about the pin.

Vertebral plate 300 is a universal anterior plate preferably for use in the lumbar spine, for example, the L1 to L5 vertebrae. Plate 300 is shown in FIGS. 5A-5E, and is shown attached to guide in FIGS. 5A and 5B. Plate 300 includes a proximal surface 301, a distal surface 302, a female mating feature 303 located at a center of plate 300, and screw holes 304. Variations of the vertebral plate may have various shape profiles which would correspond to the surgical approach and/or surgical site and may include lateral, universal, and sacral plates, as described in more detail below.

Figure 5D:
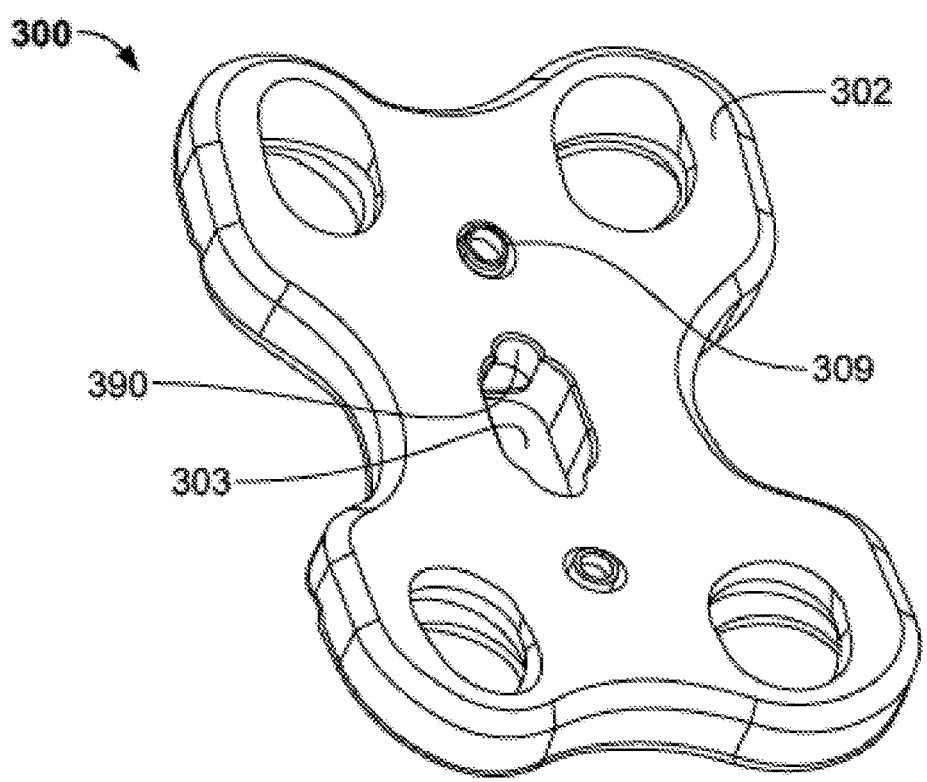
Figure 5E:
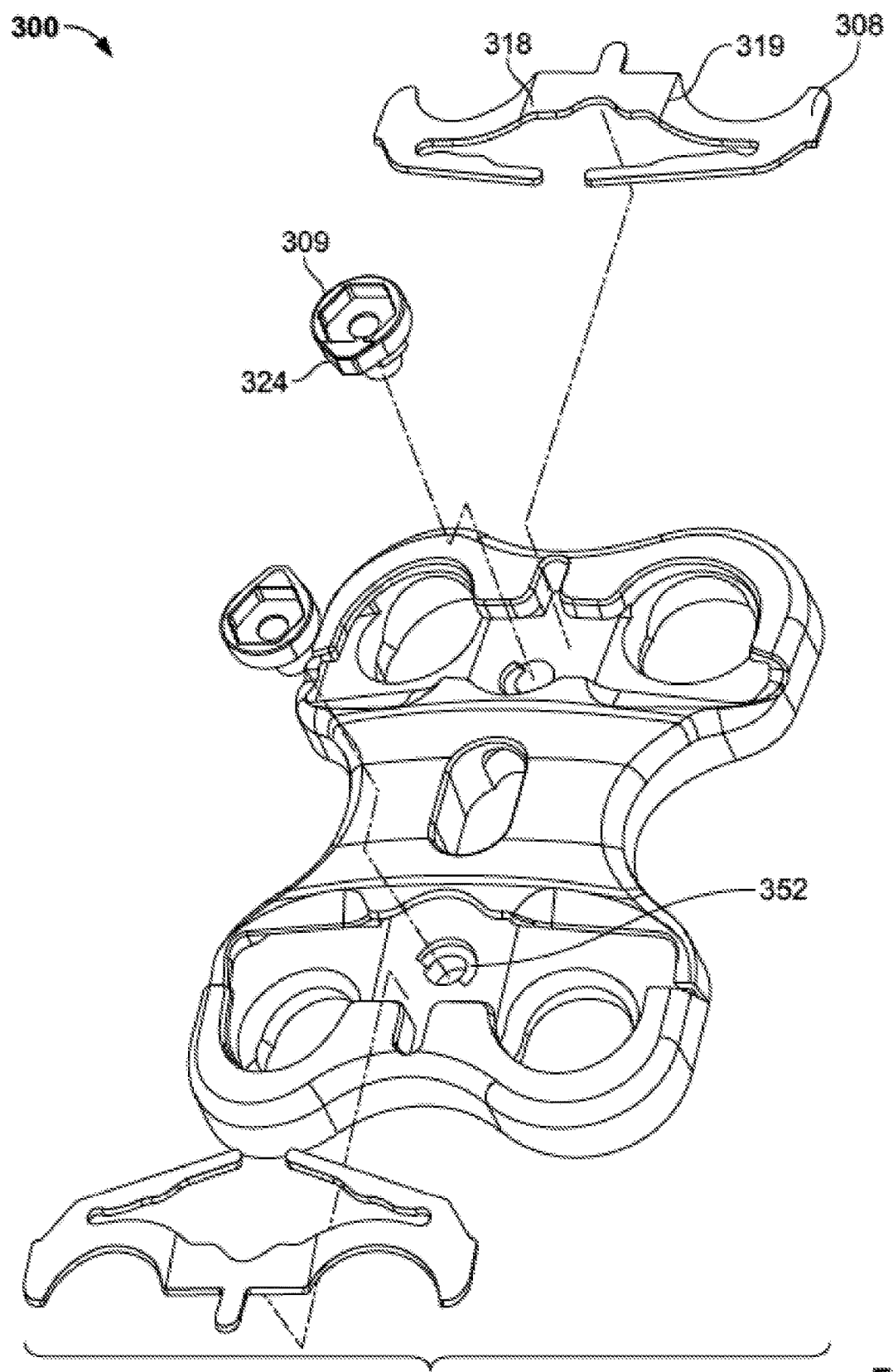
FIG. 5E is an exploded perspective view of the vertebral plate shown in FIGS. 5A and 5B.

Distal surface 202 of guide 200 is preferably configured in its profile and curvature to closely match with proximal surface 301 of plate. Upon engaging guide 200 to plate 300, male feature 207 is disposed within female mating feature 303 and and ball-detent feature 206 enhances the engagement between the two components. This is achieved by bearing 208 being seated within a detent or depression 390 on an inner surface of female mating feature 303, which can include one or more depressions 390 as shown in FIG. 5D. As indicated above, set screw 210 can be actuated to provide more or less force between bearing 208 and the detent or depression, thereby providing for a greater or lesser engagement force between guide 200 and plate 300. While a ball-detent structure is shown, any known locking mechanisms may be used. When attached, guide 200 can be manipulated by an external instrument to move as one unit with plate 300.

Figure 6A:
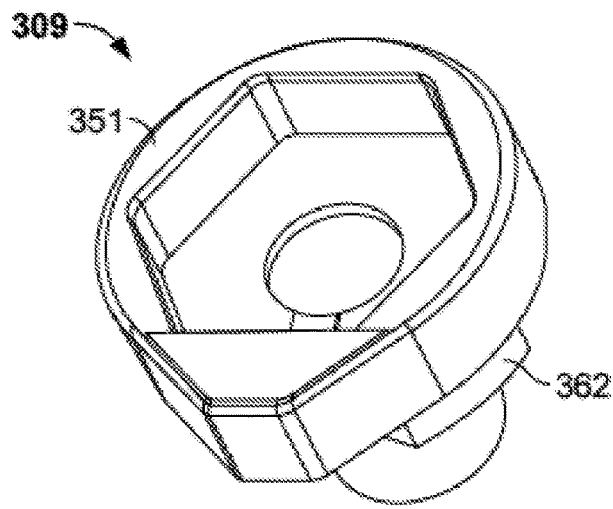
FIGS. 6A-6C are views of a cam of the vertebral plate shown in FIGS. 5A and 5B.
Figure 6B:
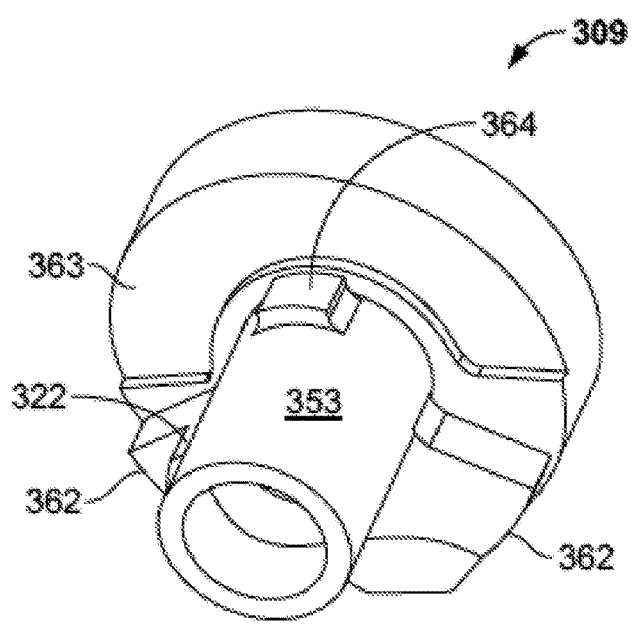
Figure 6C:
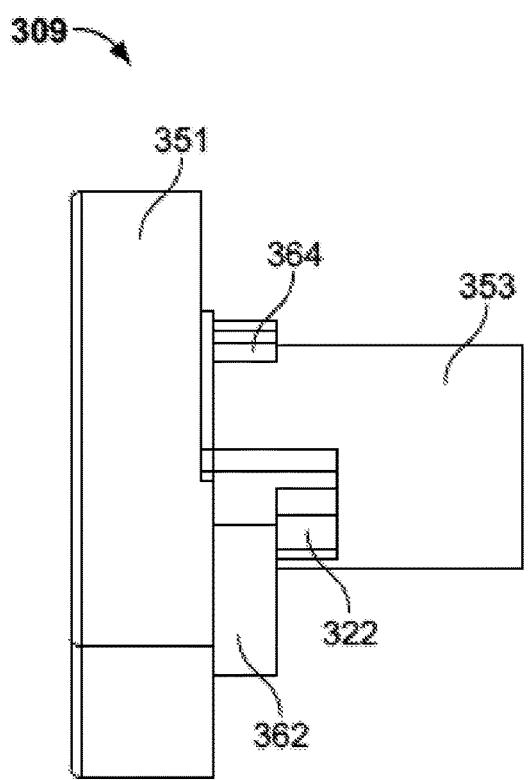

Plate 300 further includes a blocker 308 and a cam 309 configured for rotation between unlocked and locked positions. A top part 351 of cam 309 has an oblong shape, though the recessed camming surface 352 (shown in FIG. 6A) in plate 300 does not follow an oblong path. Cam 309 includes an arrow laser mark for denoting its rotational orientation to the user, and is either flush with or recessed from the top or proximal surface 301 of plate 300 to avoid contact with sensitive anatomy adjacent its intended placement on the vertebrae. The arrow laser mark is intended to be viewed by the surgeon during use. Cam 309 has a knob 322 on a shaft 353 (best seen in FIGS. 6B and 6C) that interfaces with recessed camming surface 352 on plate 300. Recessed camming surface 352 is not fully circular and includes a stop at each end to interface with knob 322 so that the surgeon can discern when cam 309 has been rotated into its fully locked or unlocked position. Wings 362 are located on shaft 353 between top part 351 and knob 322 such that they are either rotated to face and abut blocker 308 in the locked position, or to face away from blocker 308 in the unlocked position. In the locked position, the abutting wings 362 substantially prevent translational movement of blocker 308 toward cam 309, whereas in the unlocked position, at least some movement is allowed by blocker 308. Recessed portion 363 of top part 351 of cam 309 is provided for clearance with plate 300. Extension 364 is provided to enhance engagement of cam 309 with plate 300. Cam 309 includes a hex head 324 for use with a hex driver; of course, other head configurations may be employed. The distal portion of cam 309 is crimped (as shown in FIG. 5D) so that it maintains a rotational connection within a bore of plate 300.

Plate 300 is shown configured for use across a single disc space with a pair of screw holes on each side of the disc space after implantation. Multilevel plates are also contemplated in this along with all of the other plates herein described. Plate 300 includes axial, lordotic, and medial-lateral curvature to accommodate the lumbar anatomy (vertebrae L1-L5) of a patient.

A method of using the instrument 100 and guide 200 for insertion of plate 300 is shown in FIGS. 7-11. The plate utilized can be the aforementioned plate 300, any of the plates herein described, or similar embodiments of same. A plate, such as plate 300, is first selected, which selection can be made from a plurality of plates of different sizes, configurations, and/or geometries as appropriate for the particular surgical location, procedure, and patient. A guide 200 that corresponds with the selected plate is obtained based on the plate selection. Guide 200 may be configured for use with more than one plate or may be dedicated to a single particular plate. Guide 200 assists with the placement of the screws during insertion.

One of the next steps of the surgical process is to assemble the guide 200 to the implant 300. This is done by inserting male feature 207 of guide 200 into female mating feature 303 of plate 300. Screw holes 203 of guide 200 align or match up with the screw holes 304 of plate 300, as depicted in FIGS. 5A-5B. In other embodiments of the invention, the plate 300 may be wider than and therefore extend past the perimeter of guide 200 unlike what is shown in the embodiment in FIGS. 5A-5B.

Another step is to assemble instrument 100 to guide 200 via pivot pin 204. This step can either precede or follow the assembly of guide 200 to plate 300. Instrument 100 starts in an unlocked position with clips 101 open as shown in FIG. 10. After placing clips 101 around pivot pin 204, instrument 100 is moved to a locked position by pushing locking knob 105 toward handle 104. The ball-detent feature of instrument 100 can lock once this locked position is achieved, giving tactile feedback to the surgeon and aiding in maintaining the locked position of instrument 100. Fully assembled, the construct appears as depicted in FIGS. 1A, 1B, and 7.

Guide 200, and plate 300 connected with it, can rotate about the axis through pivot pin 204. Guide 200 may also be able to translate a small distance with respect to instrument 100 with pin 204 moving along the axis of instrument 100 between clips 101. Assembled together, instrument 100 is able to pivot freely about pivot pin 204 through a range of approximately 180 degrees. The connection between instrument 100 and guide 200 allows for sliding between the surfaces of clips 101 and pin 204, yet is preferably secure to the extent that the construct will maintain a particular angular configuration until plate 200 or guide 300 contacts an external structure.

Figure 7:
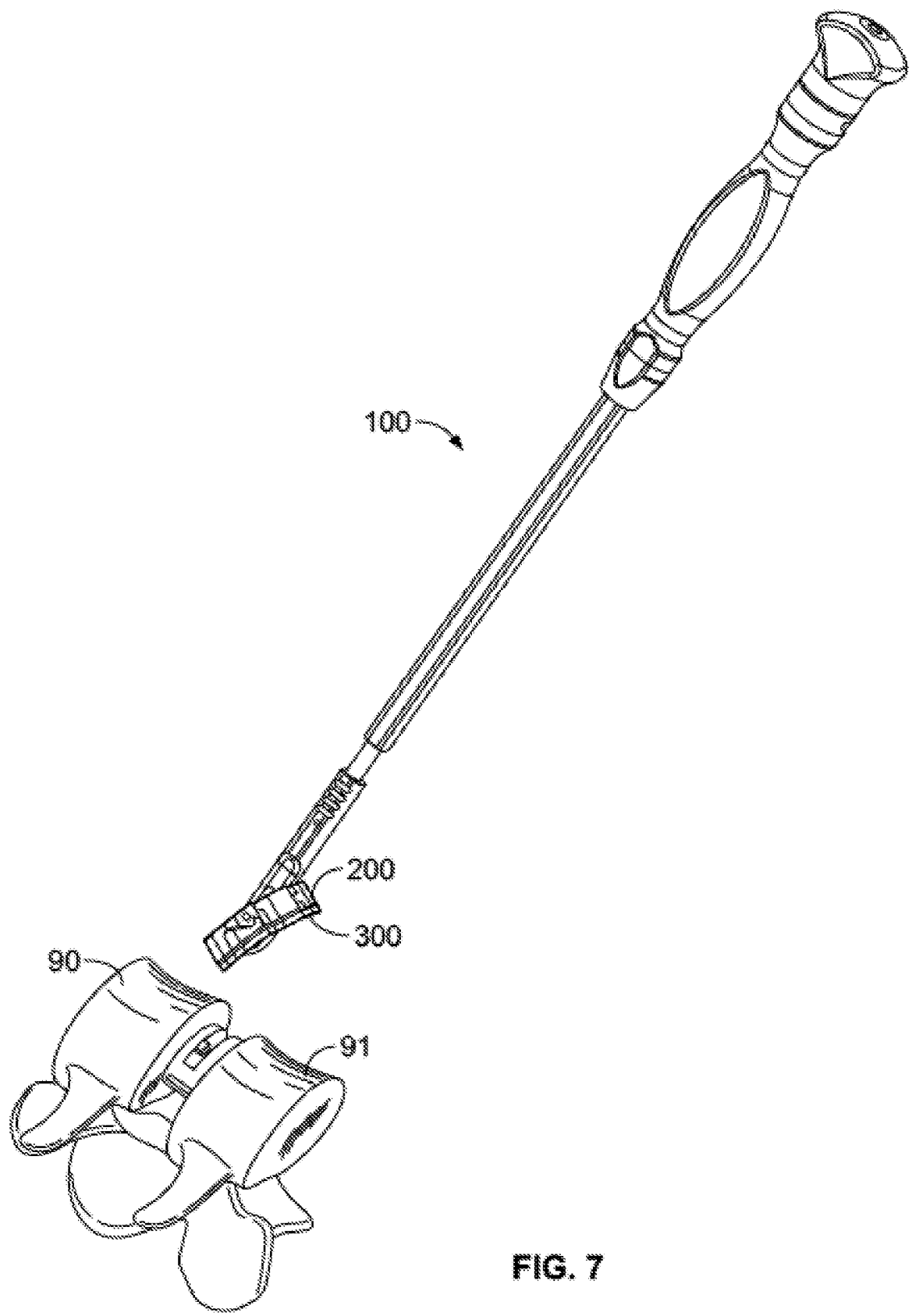
FIGS. 7-11 are perspective views of various stages of the insertion of the vertebral plate onto two vertebral bodies with the insertion instrument and the screw guide, all as shown in FIG. 1.

As shown in FIG. 7, guide 200 is rotated to one extreme end of its range with respect to instrument 100 so that one end of channel 205 is approximately in contact with the instrument 100. This allows the profile of the construct to be reduced so that it can more easily fit through small or narrow working channel.

Figure 8:
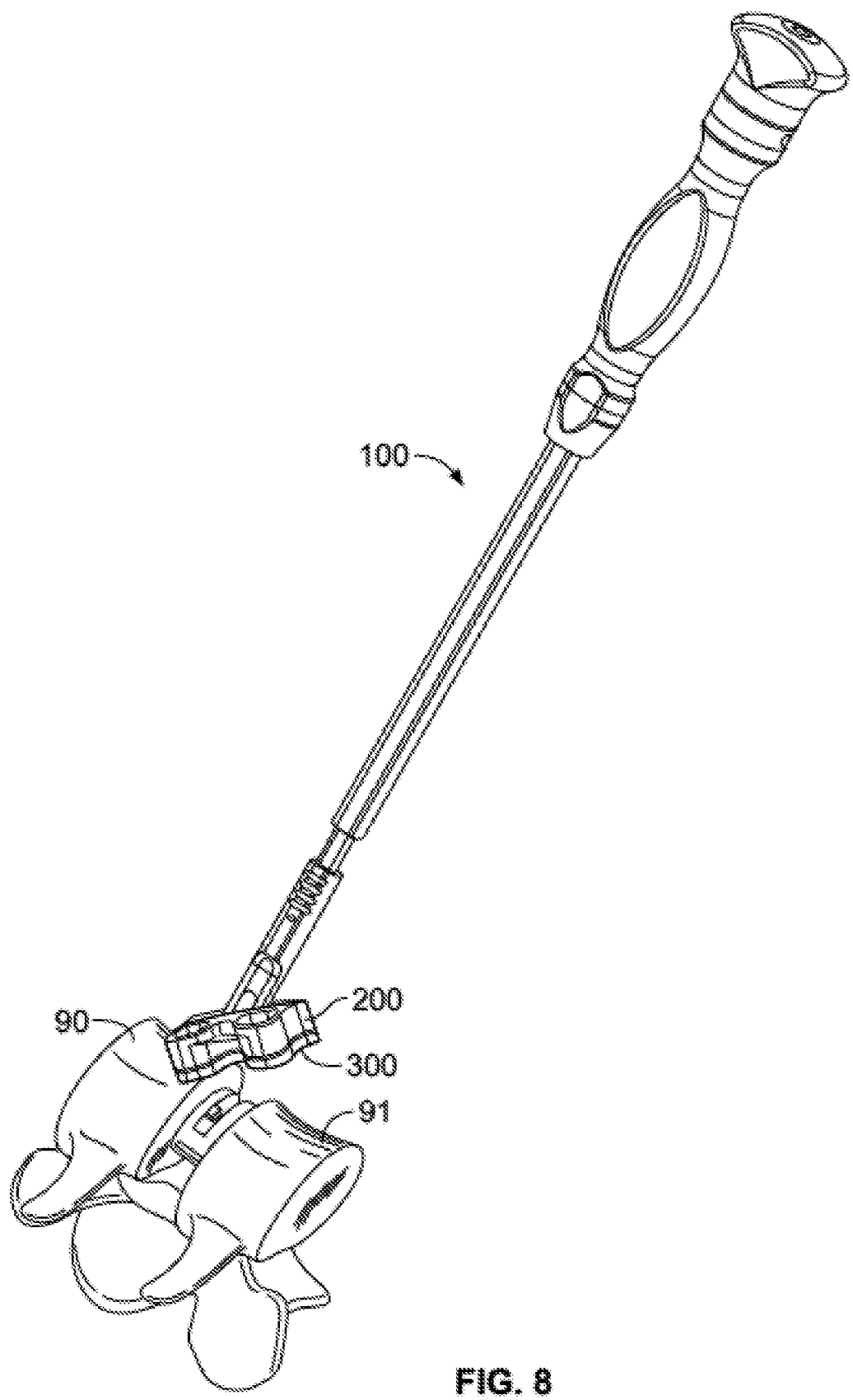
Figure 9:
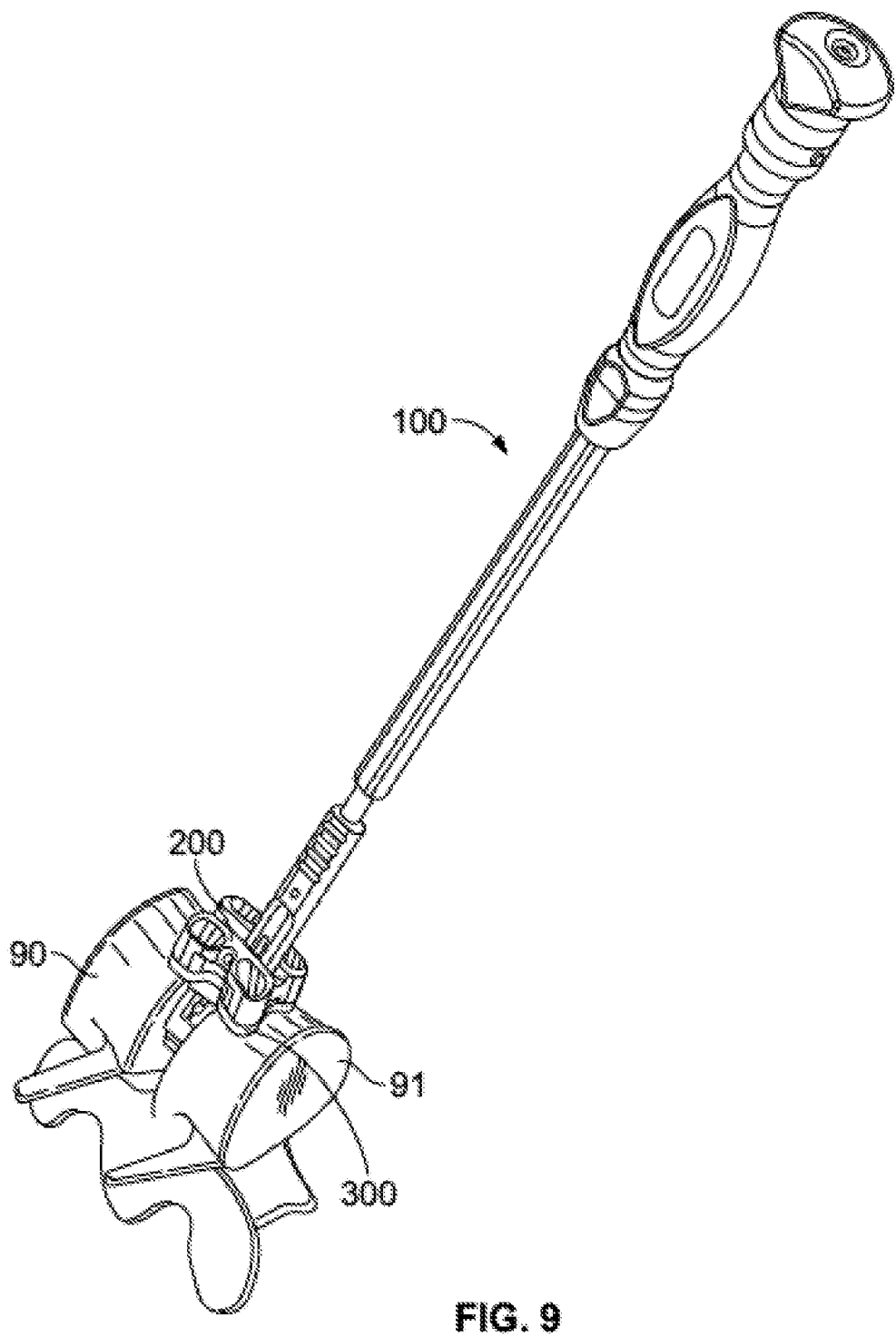

A further step of the procedure is to advance the assembled construct through a working channel, which may be a tube or cannula provided for minimally invasive access to a surgical site at vertebral bodies 90, 91 shown in FIG. 7. To position plate 300 on vertebral bodies 90, 91, the leading end of plate 300 is contacted with vertebral body 90 as shown in FIG. 8. Then, as a longitudinal force is applied on instrument 100, guide 200 pivots with respect to instrument 100 at pivot pin 204 to then rest the other end of plate 300 on vertebral body 91, as shown in FIG. 9.

Figure 12:
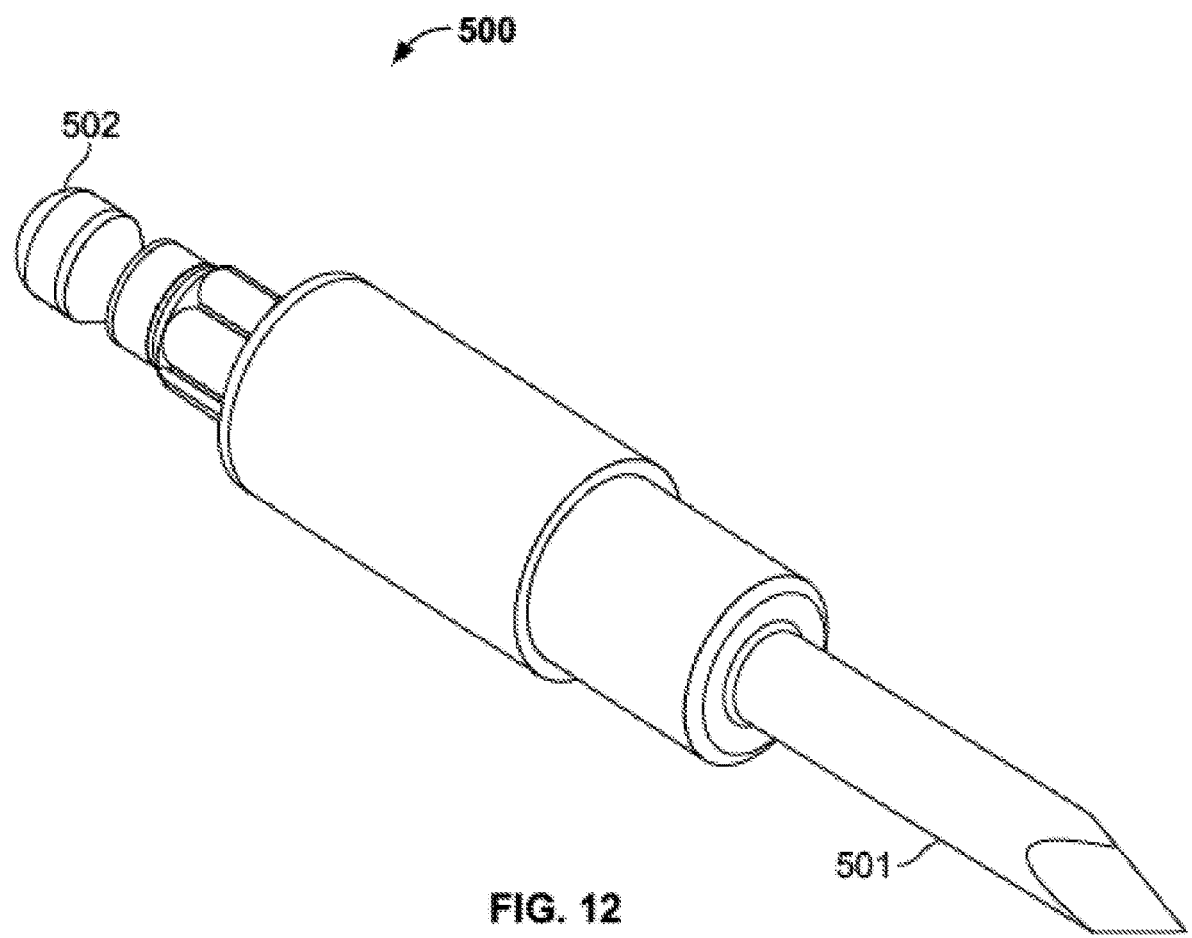
FIG. 12 is a perspective view of a fixation pin in accordance with an embodiment of the present invention.

Once the position of plate 300 is acceptable, the surgeon may insert a fixation pin 500, shown in FIG. 12, through an aperture 203 of guide 200 and an underlying screw hole 304 of plate 300 to temporarily secure plate 300 in place. Pin 500 consists of an attenuated piercing end 501 similar to a small awl at its distal end and a knob 502 at its proximal end. Knob 502 is designed to be gripped by a fixation pin inserter 510, shown in FIGS. 13A and 13B, or by any other embodiment of a pin inserter.

Use of fixation pin inserter 510 includes pulling a handle 512 back toward a proximal end 513. As this occurs, fixation pin 500 is removably attached to a distal end 511 of inserter 510. Distal end 511 can be provided internally with a female hexagonal cross-section for mating with a male hexagonal cross-sectional portion of pin 500 disposed adjacent to knob 502, as shown in FIG. 12. This assembly is advanced through the working channel. When at the surgical site and at the correct angle, handle 512 is released and/or pushed forward toward distal end 511 to release pin 500 and to lodge it into the bone. Before fixation pin inserter 510 releases pin 500, it is either impacted or under an axial load.

In order to securely and temporarily secure plate 300 in place on the vertebrae, two pins 500 are preferably used. After the insertion of pins 500, and at any point until guide 200 is removed from plate 300, insertion instrument 100 may be disengaged from guide 200 by unlocking instrument 100 and removing it from the working channel. This can be done by the surgeon using only one hand. The procedure of removing instrument 100 begins with moving it from its locked position to an unlocked position. Pulling proximally on knob 105 also pulls locking sleeve 102 proximally, exposing clips 101. Clips 101 are then allowed to flex outward and disengage from pivot pin 204 as instrument 100 is pulled proximally. The force required to effect this disengagement is weaker than the force required to disengage guide 200 from plate 300, thus allowing disengagement of instrument 100 from guide 200 before disengagement of guide 200 from plate 300. Set screw 210 of guide 200 can be manipulated to ensure that the force required to disengage guide 200 from plate 300 is relatively greater. Removal of instrument 100 from the working channel can be done to increase the amount of space for viewing and manipulation of other necessary instruments during the insertion procedure.

A further step in the procedure is to prepare pilot holes for centered and easy insertion of screws through any of screw holes 304. Of course, this would be done through any screw holes 304 unoccupied by a pin 500, which has a tip that pierces the bone without requiring a pilot hole. The hole in the bone formed by pin 500 also acts as a pilot hole for a later inserted screw. The surgeon may utilize any number of instruments to make the pilot hole, such as an awl, a drill, a tap, or a screwdriver tip.

An embodiment of a straight awl 520, depicted in FIG. 14A, consists of an attenuated piercing tip 521 at the distal end, a shaft 522, and a quick connect end 523 at the proximal end. Tip 521 is used to puncture a pilot hole in the bone accessible through in the screw holes, breaking the near cortex. An embodiment of an angled awl 530, depicted in FIG. 14B, may also be used to create pilot holes in the bone and includes a quick coupling end. The bend 531 near the distal end of awl 530 allows the surgeon to make pilot holes at greater angles from the longitudinal axis of awl 530.

The quick connect or quick coupling end 523 is designed to allow for interchangeability between different types of quick connect or quick coupling handles, or to allow one handle to be used with multiple different instruments having a quick connect or quick coupling end. It is used in various surgical instruments, some of which are shown in the figures to this application, though its application is not limited to these instruments. Quick connect handles have features that fit over and snap onto the features of quick connect end of various instruments disclosed herein, for example, quick connect end 523.

Figure 15:
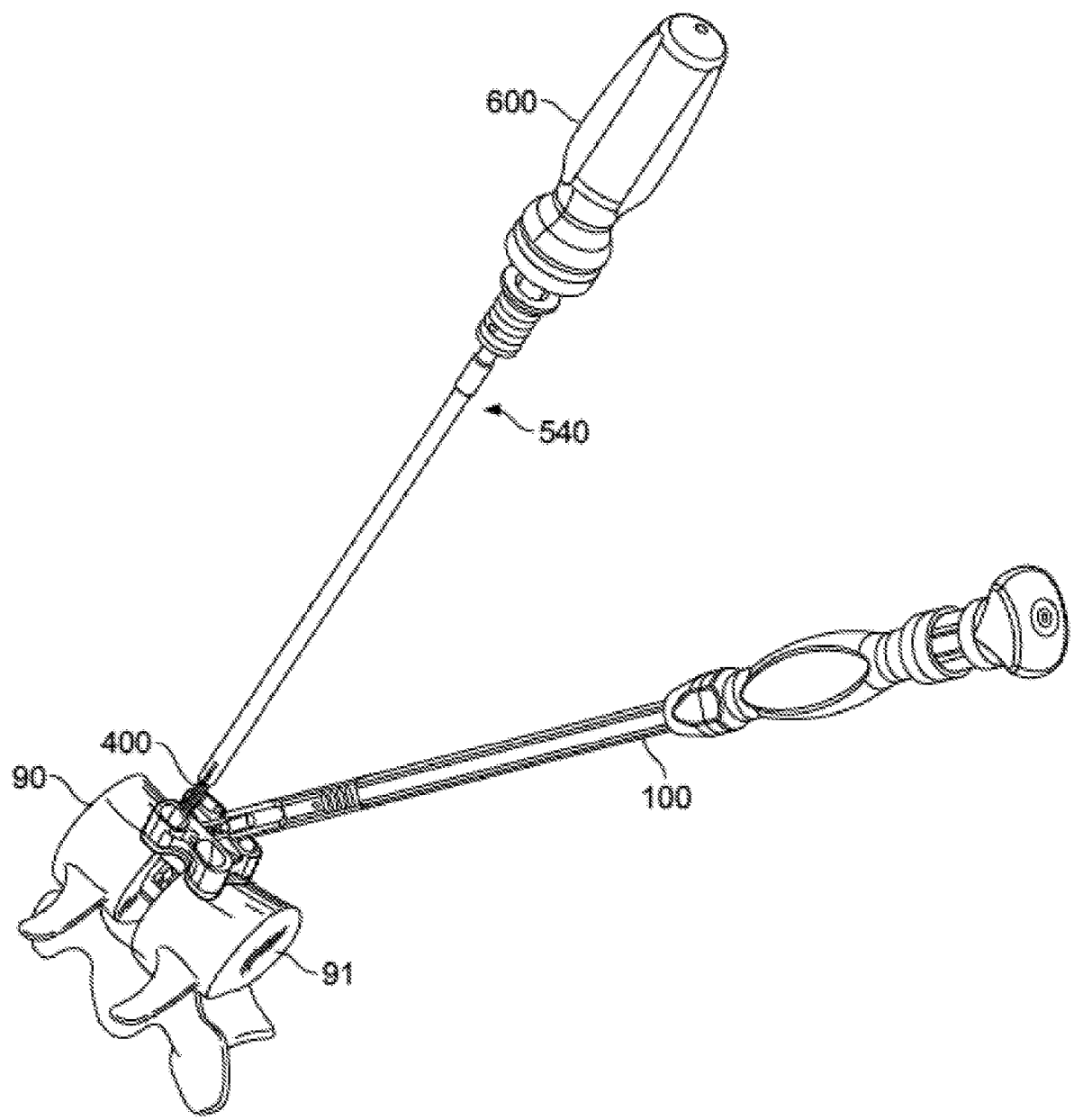
FIGS. 15 and 16 are perspective views of a screwdriver in accordance with an embodiment of the present invention utilized during insertion of the vertebral plate shown in FIG. 1 onto two vertebral bodies.
Figure 16:
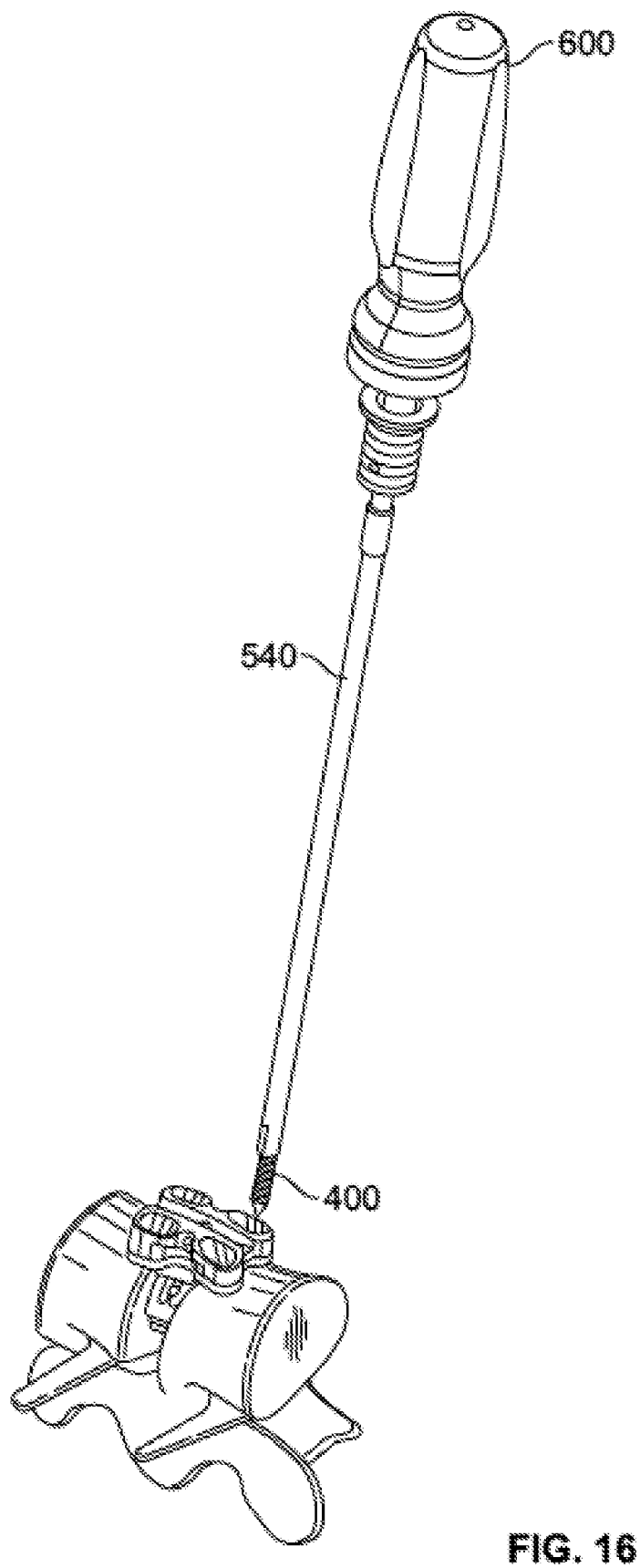

Insertion of screws can be accomplished in several ways. In one embodiment of the invention, insertion instrument 100 may be left assembled to the guide but pivoted out of the way of another instrument such as screwdriver 540, depicted in FIG. 15, which is attached to a quick connect handle 600. The ability of instrument 100 to be pivoted while it is still attached with guide 200 allows the surgeon to increase space and visibility without needing to detach instrument 100 from guide 200. As described above, insertion instrument 100 can be disengaged from the anchored guide 200 and removed completely from the working channel, if not already done so previously.

Shown in FIGS. 17A-17D are several embodiments of screwdrivers that may be used to insert screws 400 to secure plate 300 on the vertebral bodies. A self-retaining screwdriver 540 in FIG. 17A may be used at first to advance a screw 400 through the working channel and at least partially engage it with a vertebra. The self-retaining screwdriver 540 has a split head 541 at its distal end, a shaft 542, and a quick connect end 543 at its proximal end. Split head 541 has a hexagonal face 544 with a small slit 545 across the middle of its face. Slit 545 allows split head 541, which is slightly oversized compared with the similarly configured recess in screw 400, to squeeze into the head of a screw 400 and apply enough outward pressure to hold screw 400 securely on the distal end of screwdriver 540. After screw 400 is advanced through the working channel and at least partially screwed into the bone, the surgeon may then switch to a finishing screwdriver 550, depicted in FIG. 17B, which has a solid hexagonal face 554 without a slit. Finishing screwdriver 550 is used to tighten screw 400 and secure plate 300 against vertebral bodies 90, 91. The head of finishing screwdriver 550 more closely matches the size of the recess in screw 400.

Figure 17A:
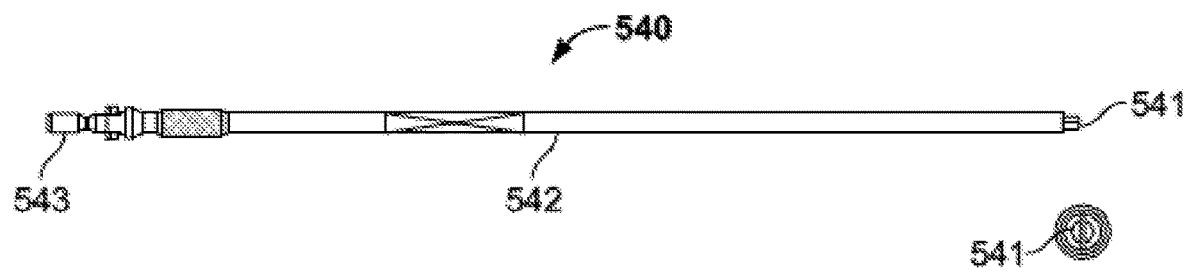
FIG. 17A is an elevational side view of a self-retaining screwdriver in accordance with an embodiment of the present invention.
Figure 17B:
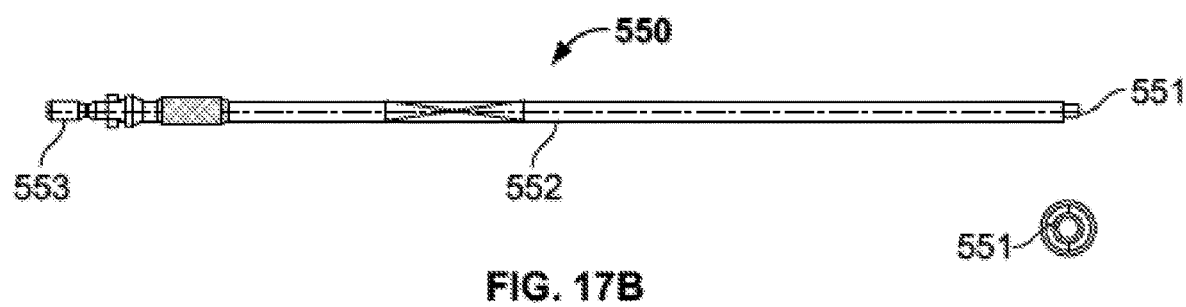
FIG. 17B is an elevational side view of a finishing screwdriver in accordance with an embodiment of the present invention.
Figure 17C:
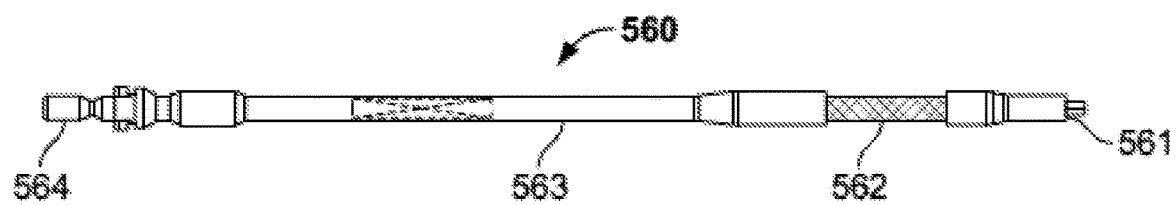
FIGS. 17C and 17D are elevational side views of a flexible screwdriver in accordance with an embodiment of the present invention.
Figure 17D:
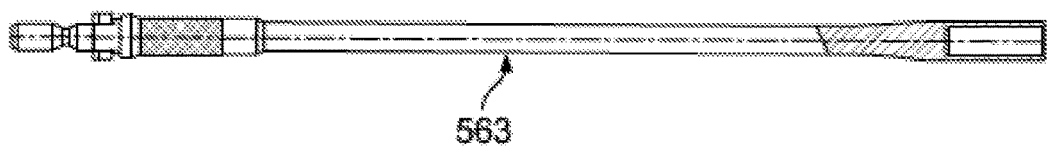
Figure 18:
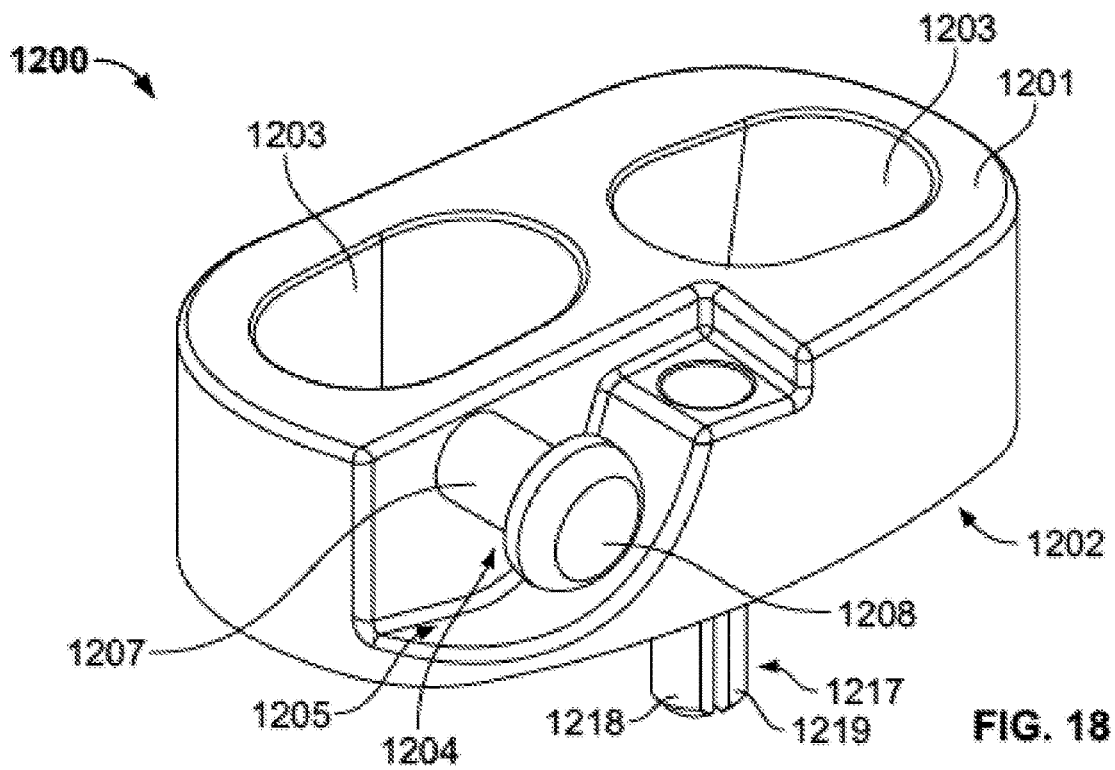
FIG. 18 is a perspective view of a screw guide in accordance with an embodiment of the present invention.

A flexible screwdriver 560, shown in FIGS. 17C and 17D, may also be used in the process of inserting and tightening screws. Similar to the other screwdrivers, this embodiment of a flexible screwdriver 560 comprises a head 561, depicted here as a split head (though it may also not include a split), a shaft 563, and a quick connect end 564. In addition, there is a flexible shaft 562 inserted between shaft 563 and head 561. This flexible shaft 562 can be bent at various angles while transferring torque from the handle to the head. An advantage of using flexible screwdriver 560 is that it can insert screws at angles that would otherwise be hard to reach when using a narrow working channel.

Once screws 400 are placed through the desired open screw holes 304 of plate 300, pins 500 are removed using the quick connect handle. Additional screws can be placed in these vacated screw holes 304 by the method described above.

Figure 11:
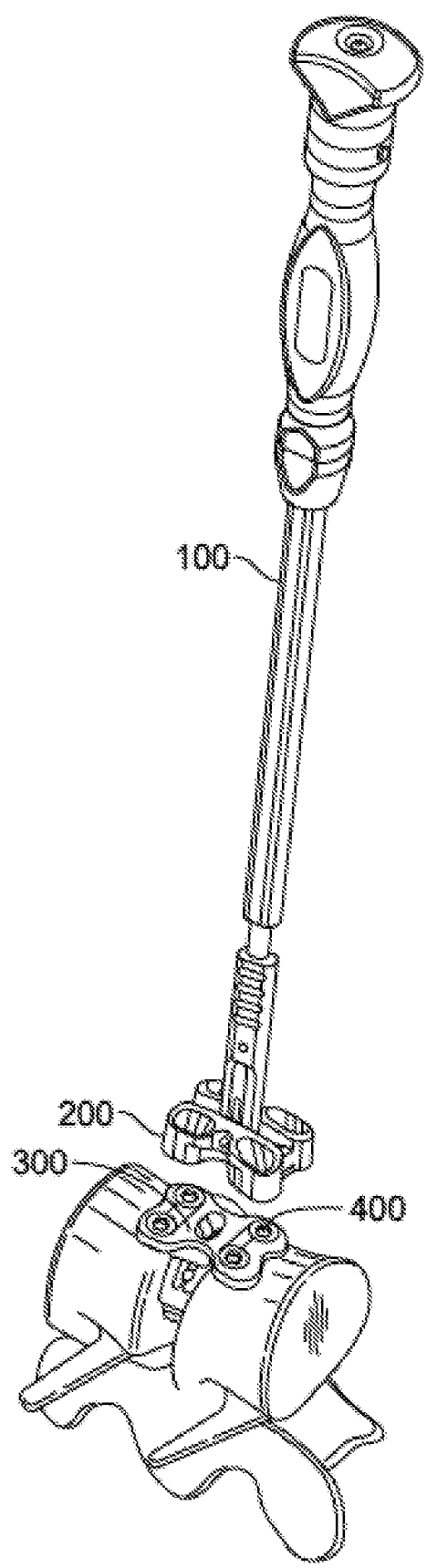

It will be appreciated that apertures 203 of guide 200 are configured for screws 400 to pass entirely therethrough, while screw holes 304 of plate 300 are of course configured so that screws 400 can anchor plate 300 to the adjacent bone. Once screws 400 have all been inserted, guide 200 may be detached from plate 300 by using insertion instrument 100. If instrument 100 was removed previously, it must be reattached by locking clips 101 over locking pin 204 in the manner described above. Then, the surgeon can pull back gently on the locked instrument 100 to disengage ball-detent feature 206 of guide 200 from plate 300, thus detaching the guide 200 from the plate 300 as shown in FIG. 11. Guide 200 may be reoriented with respect to insertion instrument 100 to resemble the position depicted in FIG. 1 through gentle engagement with surrounding anatomy or by using another instrument. Then guide 200 can be withdrawn from the surgical site and the working channel with insertion instrument 100.

The ability of instrument 100 to both pivot with respect to and be removed entirely from guide 200 provides the surgeon with flexibility during the procedure to accommodate the needs of a particular procedure. The simplicity of the control of instrument 100 allows the surgeon to make decisions during the procedure as to whether instrument 100 should be removed or remain engaged with guide 200. The engagement of instrument 100 with pivot pin 204 of guide 200 allows instrument 100 to be angled away without affecting the alignment of apertures 203 and screw holes 304. Thus, guide 200 can be utilized even when the apparatus is at an angled configuration. Moreover, the engagement of instrument 100 with guide 200 and not specifically with plate 300 allows guide 200 to be implanted with plate 300 to assist in screw insertion, and to be easily retrieved should instrument 100 be removed during the procedure.

Another embodiment of a guide 1200 and a 2-hole lateral plate 1300 are shown in FIGS. 18-23C, and can be utilized with instrument 100, described above. Screw guide 1200 has a proximal surface 1201, a distal surface 1202, and a pair of apertures 1203 configured to be aligned with screw holes of plate 1300. A side channel 1205 is located adjacent a side of guide 1200 and is accessible via proximal surface 1201. A pivot pin 1204 extends into side channel 1205 and is positioned and configured to be engaged by clips 101 of instrument 100. Pin 1204 includes a neck 1207 engageable by clips 101 and a knob 1208 at an end of neck 1207 opposite the side wall of guide 1200. Knob 1208 is dimensioned and configured to prevent clips 101 from sliding off to the side of pin 1204 once engaged therewith. As it is with channel 205 of guide 200, channel 1205 is configured so that instrument 100, when engaged with guide 1200, can pivot freely with minimal obstruction about the axis defined by pivot pin 1204.

Figure 19:
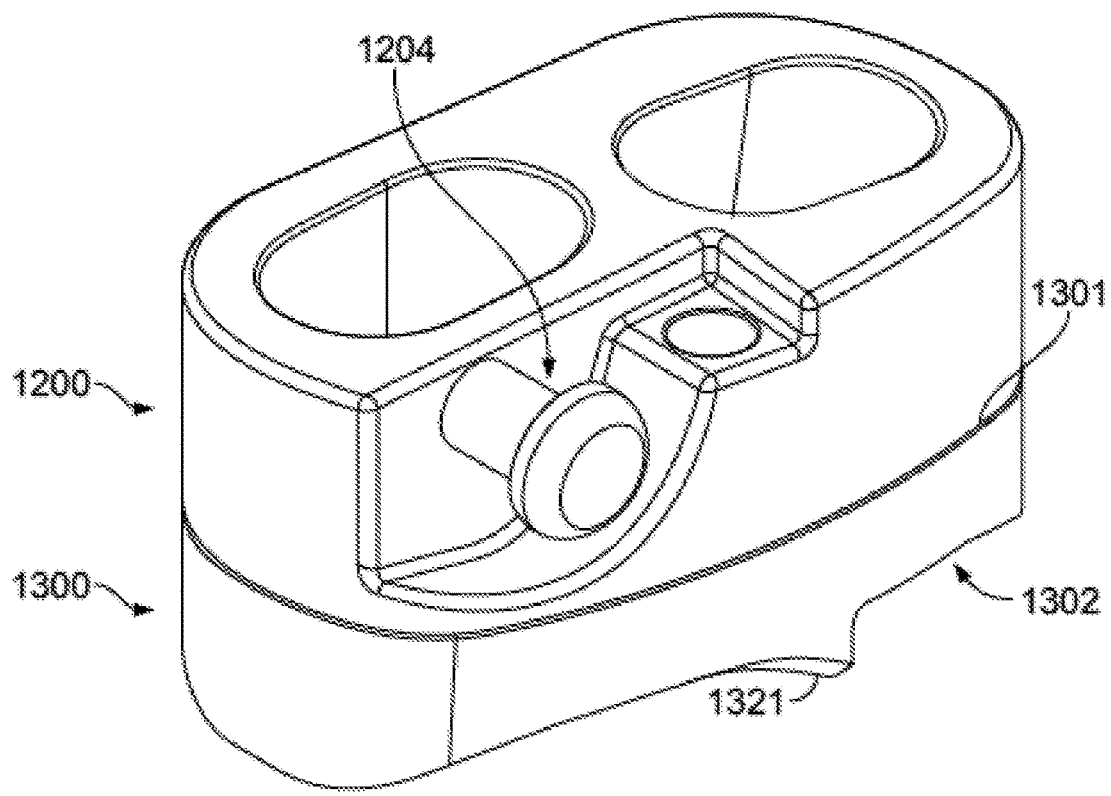
FIG. 19 is a perspective view of the screw guide shown in FIG. 18 assembled with a vertebral plate in accordance with another embodiment of the present invention.
Figure 21:
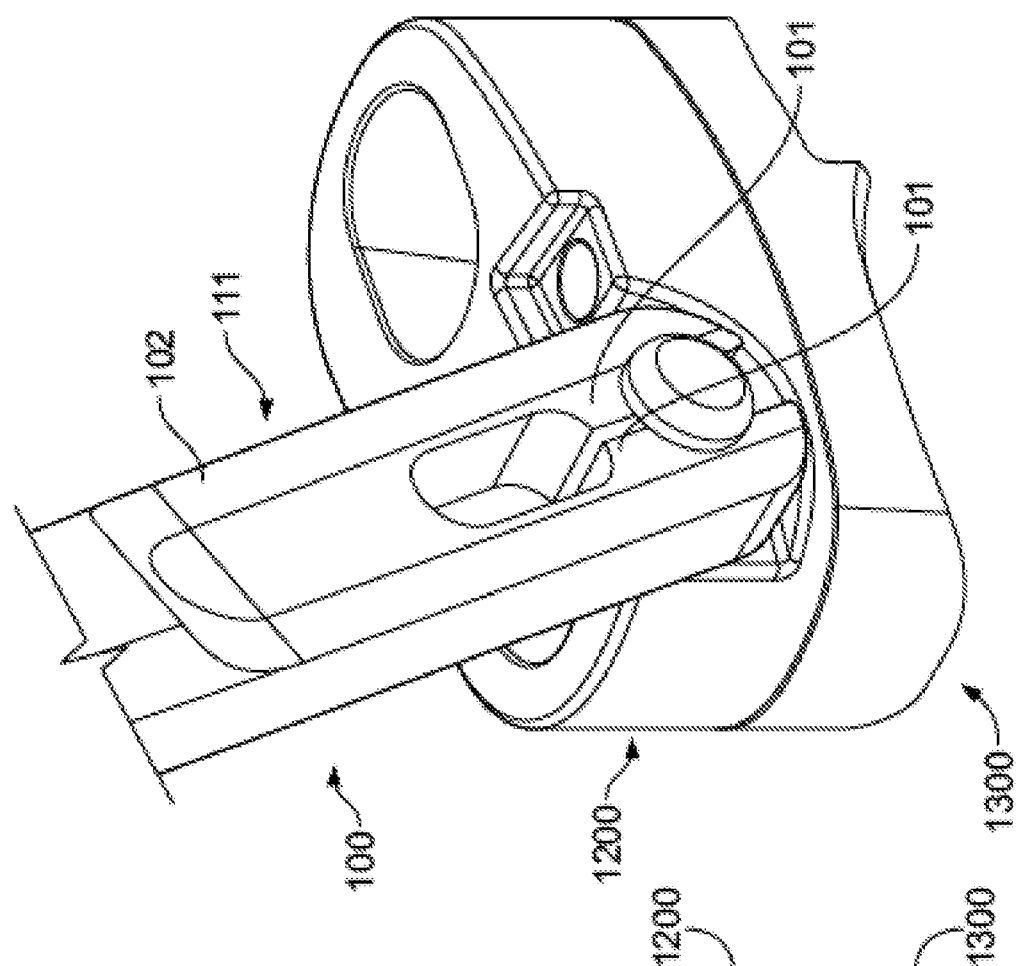
FIGS. 20 and 21 are perspective views of an insertion instrument in accordance with another embodiment of the present invention assembled with the screw guide and vertebral plate shown in FIG. 19.
Figure 20:
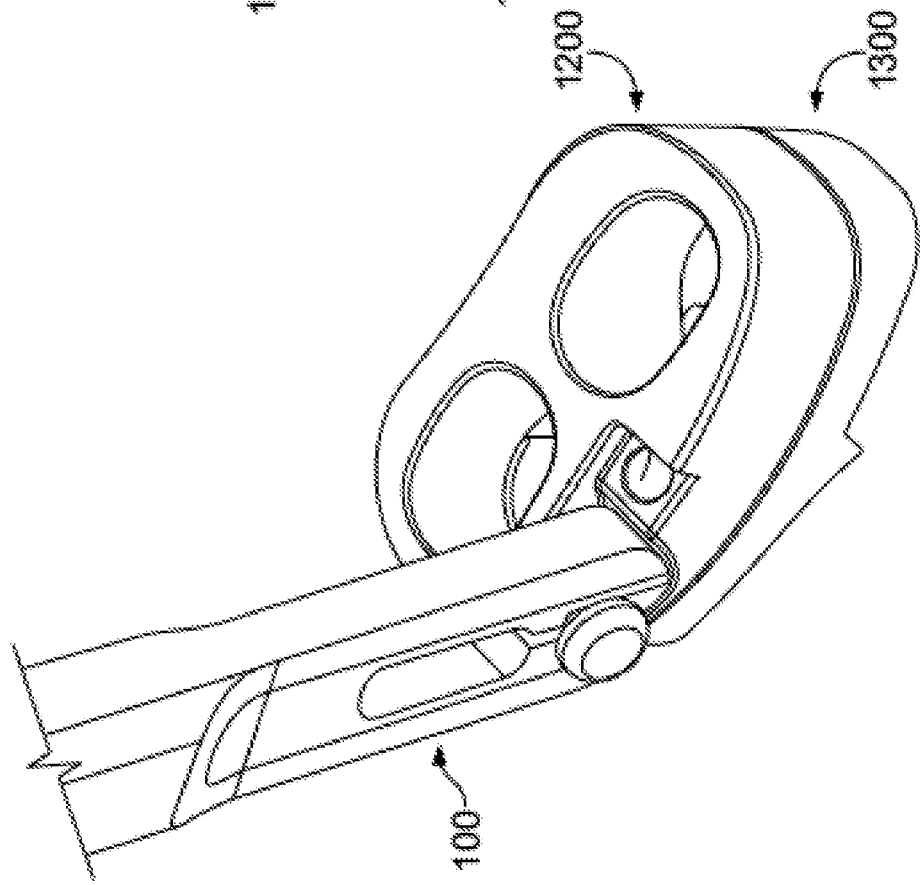

Extending from distal surface 1202 of guide 1200 is a male feature 1217, which can assist in holding plate 1300 in its removable engagement with guide 1200, as shown in FIG. 19. Feature 1217 is split into two complimentary shanks 1218 and 1219 that can seat within an instrument opening 1314 (shown in FIGS. 23A and 23B) of plate 1300. Shanks 1218 and 1219 operate similarly to split head 541 of self-retraining screwdriver 540, described above, when removably engaging the female feature of instrument opening 1314.

Plate 1300 includes a proximal surface 1301, a distal surface 1302, and screw holes 1305 that align with apertures 1203. Each blocker 1308 is dedicated to only a single screw hole 1305. Plate 1300 includes the same cam 1309 as cam 309. A channel 1340 is cut through a side of plate 1300. The curvature and lip features 1312, 1313 accommodate lateral aspects of vertebral bodies (i.e. osteophytes).

Figure 23A:
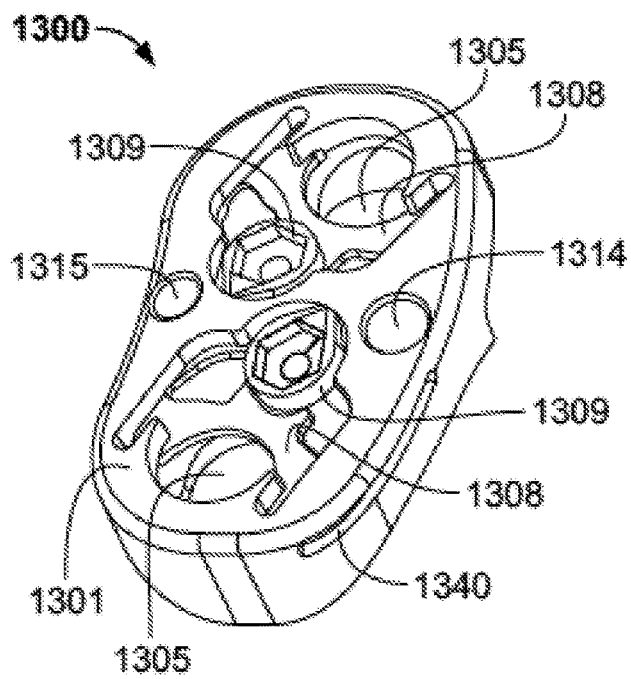
FIGS. 23A-23C are views of a vertebral plate in accordance with another embodiment of the present invention.
Figure 23B:
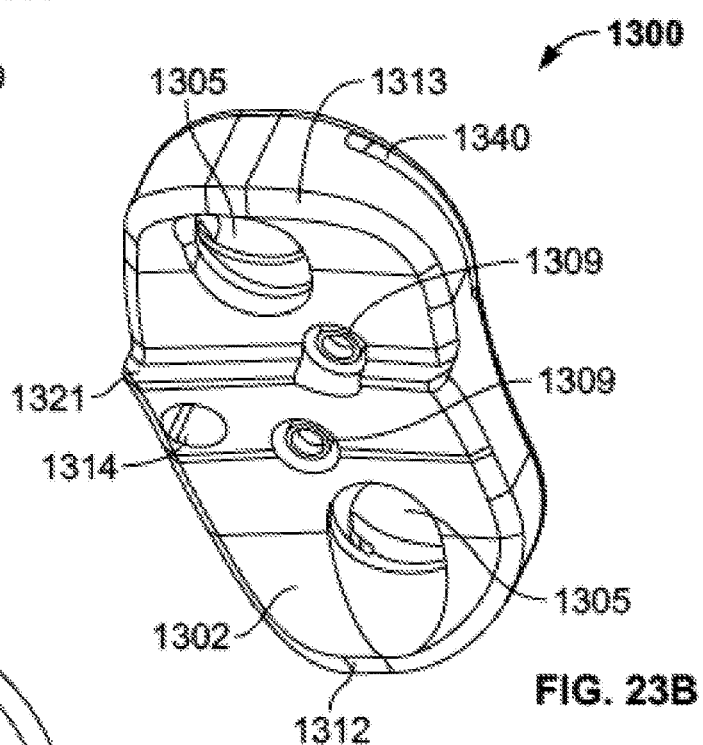
Figure 23C:
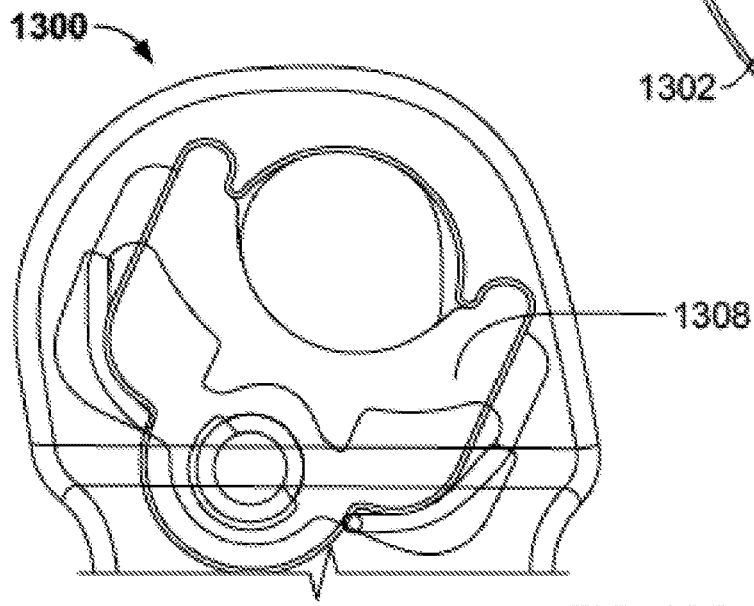

A ledge feature, ridge, or protrusion 1321 extends distally from distal surface 1312 and may be placed to fit between and/or to abut one or both of the adjacent vertebrae upon implantation of plate 1310. Ridge 1321 is configured to be small so that plate 1300 can be easily manipulated and maneuvered even through small working channels. Also provided on plate 1300 is an opening 1315 that can be either blind or extend through plate 1300. Instrument opening 1314, which can be threaded, extends completely through the thickness of plate 1300, as shown in FIGS. 23A and 23B. Blind opening 1315 extends into, but not completely through, the thickness of plate 1300. Instrument opening 1314 is used to engage an insertion tool or an insertion guide, such as guide 1200 or plate inserter 700 described above. Blind opening 1315 may be used to connect with another aspect of a guide or instrument to prevent rotation between plate 1300 and the respective guide or instrument.

Figure 22A:
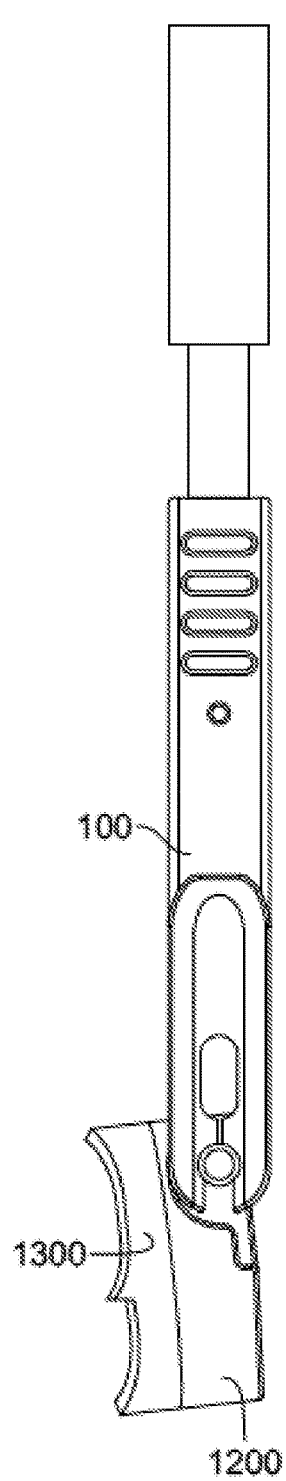
FIGS. 22A-22C are perspective views of various stages of the positioning of the vertebral plate and the screw guide with respect to the insertion instrument, all as shown in FIGS. 20 and 21.
Figure 22B:
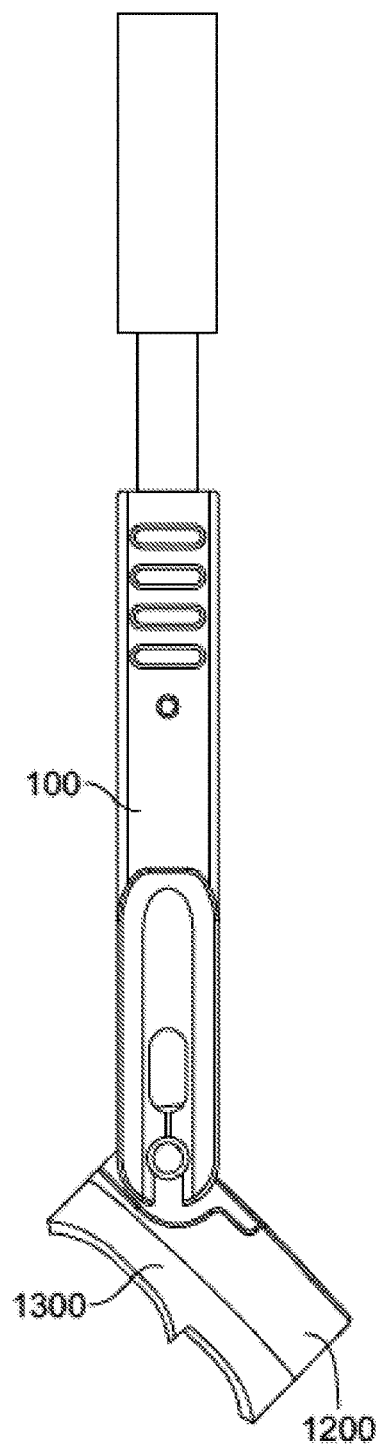
Figure 22C:
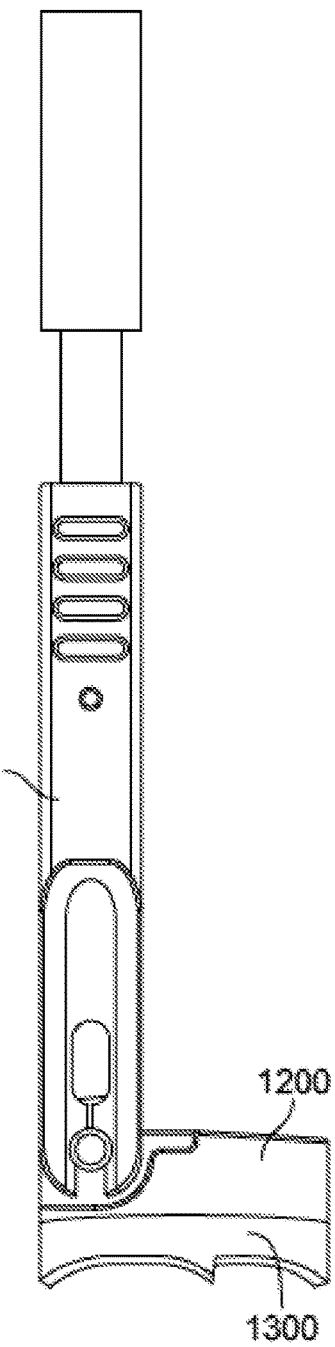

A method of using the instrument 100 and guide 1200 for insertion of vertebral plate 1300 is shown in FIGS. 22A-22C and is similar to the method described above. FIG. 22A depicts guide 1200 and plate 1300 angled with respect to instrument 100 so that a low profile can be achieved for insertion of the construct. The axis of instrument 100 is approximately parallel with a plane defined by proximal surface 1201 of guide 1200. That is, channel 1205 is configured such that instrument 100 can be configured with its axis perpendicular or nearly perpendicular to the orientation of its axis when normal to guide 1200, as shown in FIG. 22C. FIG. 22B depicts guide 1200 and plate 1300 rotated toward their implantation position, which is shown in FIG. 22C.

Two embodiments of plate inserters 600 and 700 are shown in FIGS. 24A-24C and FIGS. 25A-25E, respectively. Plate inserters 600 and 700 are configured to be used for insertion of a vertebral plate without the need for a guide attached to the plate. That is, the above described embodiments include an instrument attached to a guide that is in turn attached to a plate. Plate inserters 600 and 700 attach directly to a plate.

Plate inserter 600 includes a proximal end 601 having a quick connect end and a distal end 602 having an interface for mating with a vertebral plate. At distal end 602, a shaft 604 is pivotally connected with a link 605 about a pin 603. A Belleville washer is assembled under load at the interfacing joint between shaft 604 and link 605 so that the interfacing joint does not allow the components connected thereat to move freely. That is, some manipulation is required by the user to cause movement of link 605 with respect to shaft 604.

Housed in the distal portion of link 605 is an engagement end 606 configured to mate within a female feature of the intervertebral plate. It will be appreciated that engagement end 606 is similar in nature to antirotation (or male) feature 207 of guide 200, described above. Indeed, link 605 can be configured and dimensioned to be used within female mating feature 303 of plate 300 or female mating feature 2713 of plate 2700. In that way, plate inserter 600 can be used as an alternative to instrument 100 and guide 200 if a direct connection between the insertion instrument and the plate is desired.

Figure 24A:
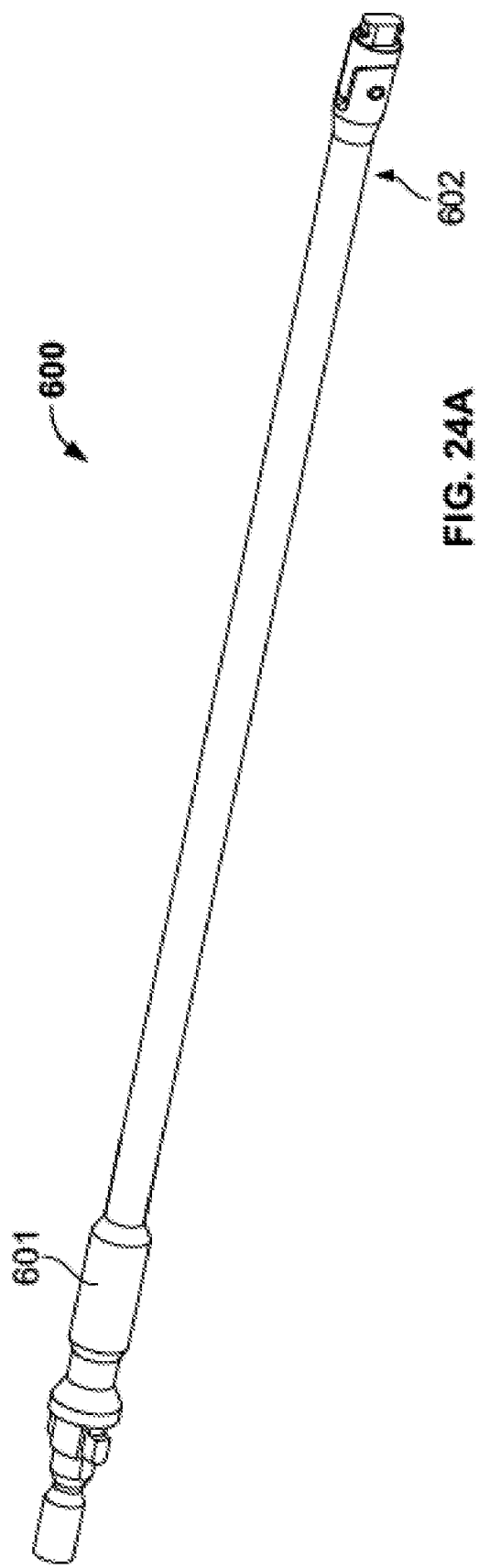
FIG. 24A is a perspective view of a plate inserter instrument in accordance with another embodiment of the present invention.
Figure 24B:
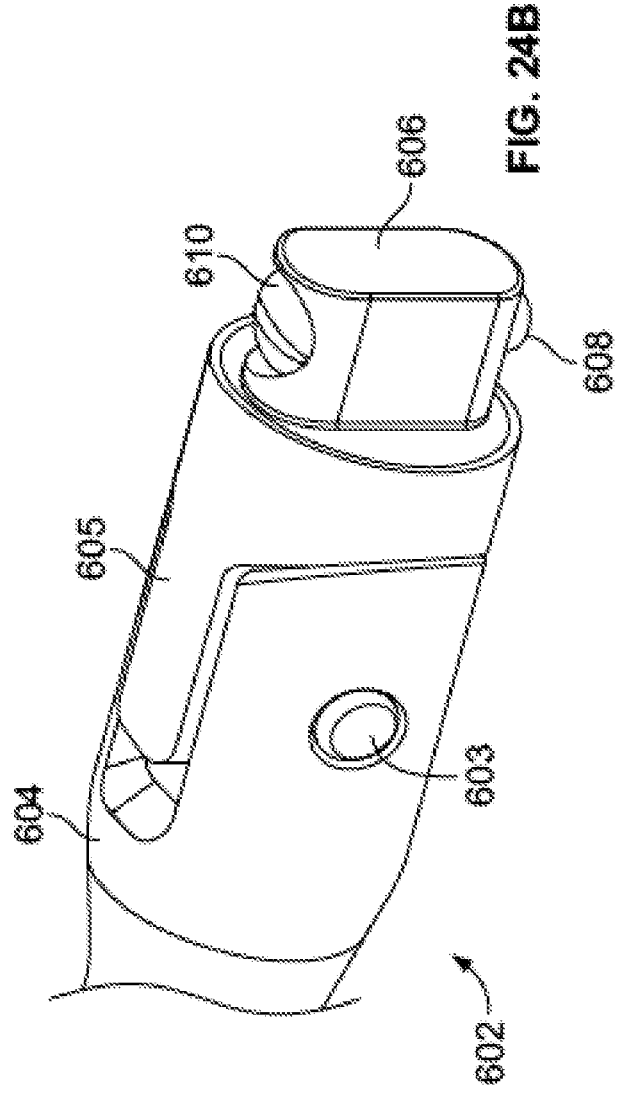
FIG. 24B is a perspective view of a distal end of the plate inserter instrument shown in FIG. 24A.
Figure 24C:
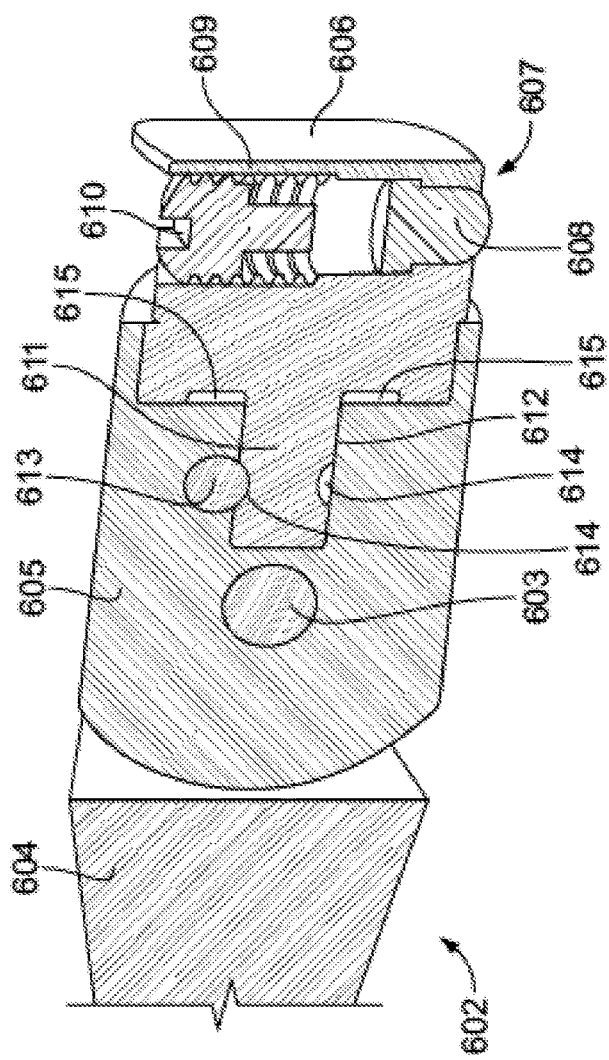
FIG. 24C is a perspective sectional view of the distal end of the plate inserter instrument shown in FIG. 24B.
Figure 25A:
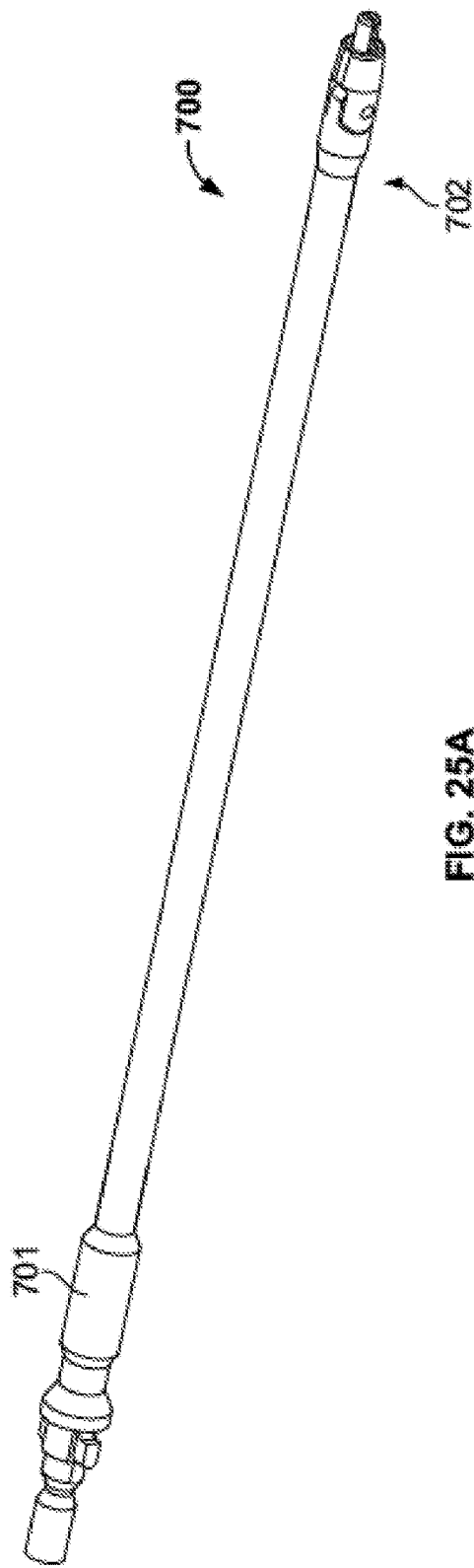
FIG. 25A is a perspective view of a plate inserter instrument in accordance with another embodiment of the present invention.
Figure 25B:
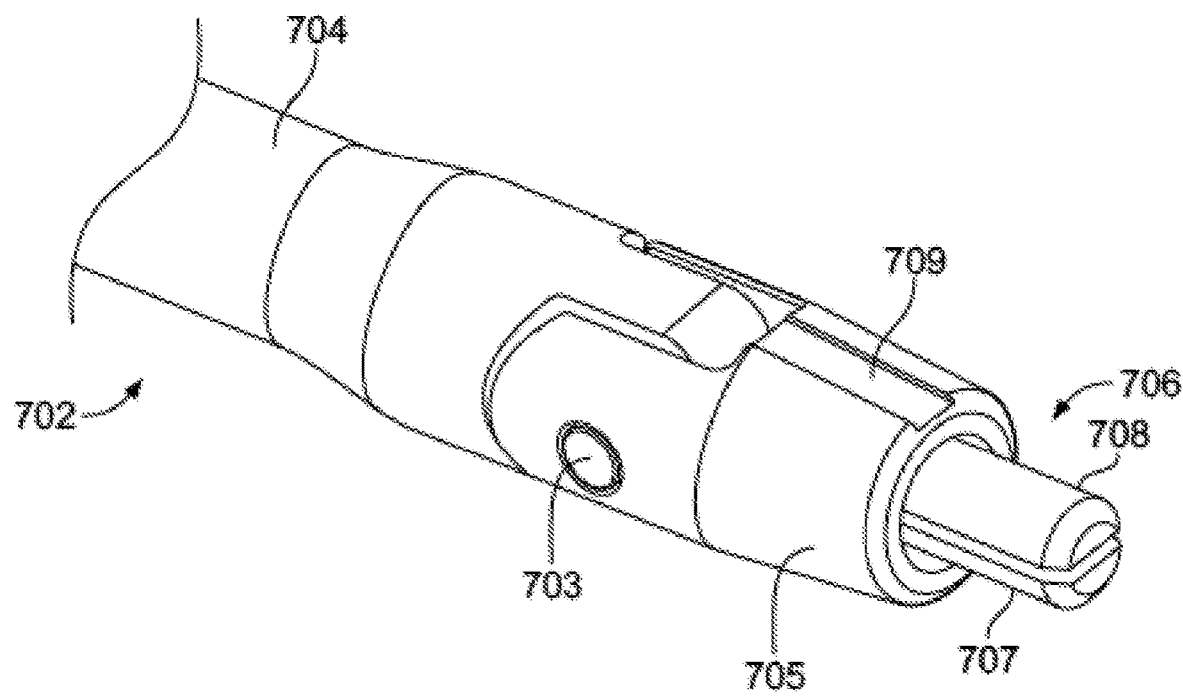
FIG. 25B is a perspective view of a distal end of the plate inserter instrument shown in FIG. 25A.
Figure 25C:
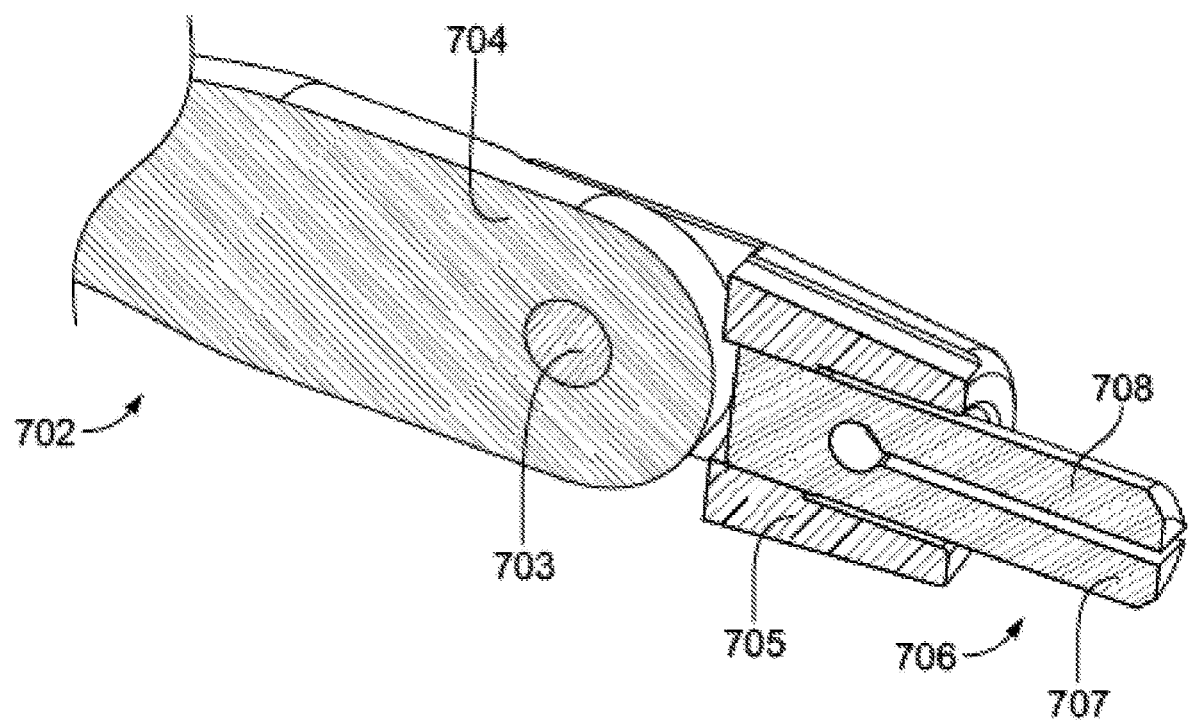
FIG. 25C is a perspective sectional view of the distal end of the plate inserter instrument shown in FIG. 25B.
Figure 25D:
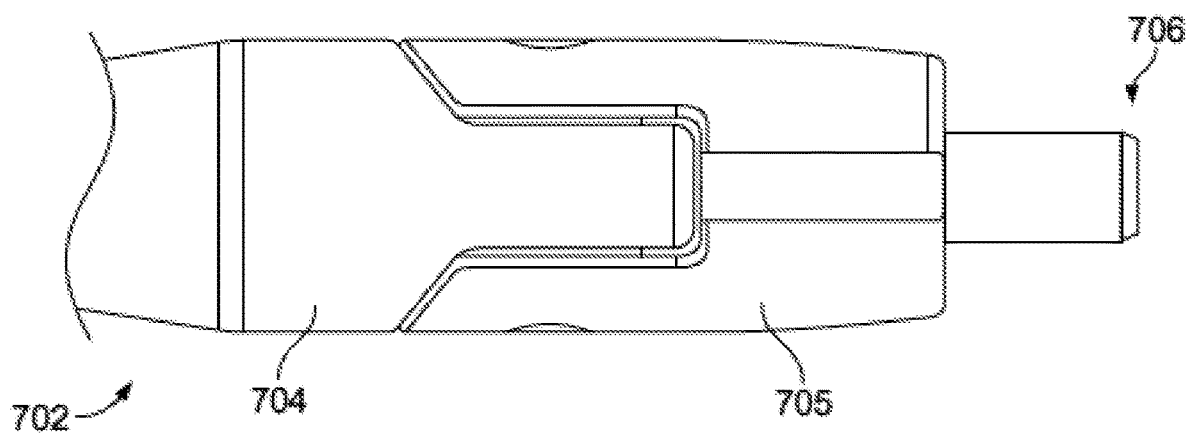
FIG. 25D is a top plan view of the distal end of the plate inserter instrument shown in FIG. 25B.
Figure 25E:
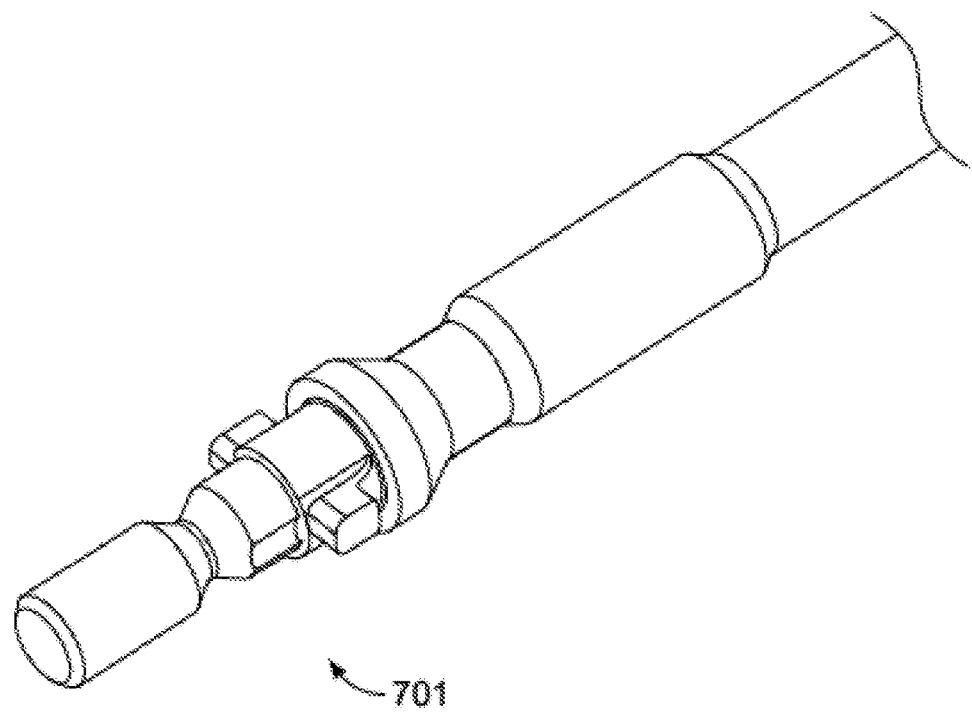
FIG. 25E is a perspective view of the proximal end of the plate inserter instrument shown in FIG. 25A.

Engagement end 606 includes a ball-detent feature 607 to assist in holding a plate in its removable engagement with inserter 600. Ball-detent feature 607 is similar in operation to ball-detent feature 206 described above and includes a bearing 608, a spring 609, and a set screw 610 housed within a passage of end 606, as depicted in FIG. 24C. The above description of feature 207 is descriptive of the functionality of feature 607, and accordingly, that functionality is not herein reproduced.

Another feature of inserter 600 is that end 606 is configured to rotate within link 605 about an axis perpendicular to that of pin 603. A post 611 of end 606 is disposed within a cylindrical bore 612 of link 605. A ball-detent feature is provided to assist in maintaining instrument end 606 in a particular orientation with respect to link 605. At least one ball 613 is provided to fit in any one of a number of detents 614 provided on post 611. This provides a finite number of positions at which end 606 can be oriented with respect to link 605. At least two springs 615 are also provided to ensure proper tensioning between end 606 and link 605 and to provide an amount of cushioning when engaging inserter 600 to a plate. End 606 can be rotated with respect to link 605 by the surgeon inserting end 606 into plate and twisting or rotating shaft 604 and link 605 to the correct vertical or horizontal position. This configuration of inserter 600 allows end 606 to be fully pivoted and rotated with respect to shaft 604.

Plate inserter 700 includes a proximal end 701 having a quick connect end and a distal end 702 having an interface for mating with a vertebral plate. At distal end 702, a shaft 704 is pivotally connected with a link 705 about a pin 703 in a similar configuration to that provided in inserter 600. A Belleville washer is assembled under load at the interfacing joint between shaft 704 and link 705 so that the interfacing joint does not allow the components connected thereat to move freely. That is, some manipulation is required by the user to cause movement of link 705 with respect to shaft 704.

Housed in the distal portion of link 705 is an engagement end 706 configured to mate within a female feature of the intervertebral plate, such as instrument opening 1314. It will be appreciated that engagement end 706 is similar in nature to male feature 1217 of guide 1200, described above. In that way, plate inserter 700 can be used as an alternative to instrument 100 and guide 1200 if a direct connection between the insertion instrument and the plate is desired.

Engagement end 706 operates is similar in operation to male feature 1217 described above and is split into two complimentary shanks 707 and 708 that can seat within a female feature of a vertebral plate to assist in holding a plate in its removable engagement with inserter 700. Shanks 707 and 708 also operate similarly to split head 541 of self-retraining screwdriver 540, described above, when removably engaging the female feature of a plate. The above description of feature 1217 is descriptive of the functionality of end 706, and accordingly, that functionality is not herein reproduced. End 706 is also removable within link 705 so that a differently configured end 706 can be utilized as needed. A marking 709 can be located at one or more points on link 705 to give the user an indication of the orientation of link 705.

Additional embodiments of plates in connection with the present invention are described below. Certain similarities are present between the following embodiments and those described above.

Figure 26A:
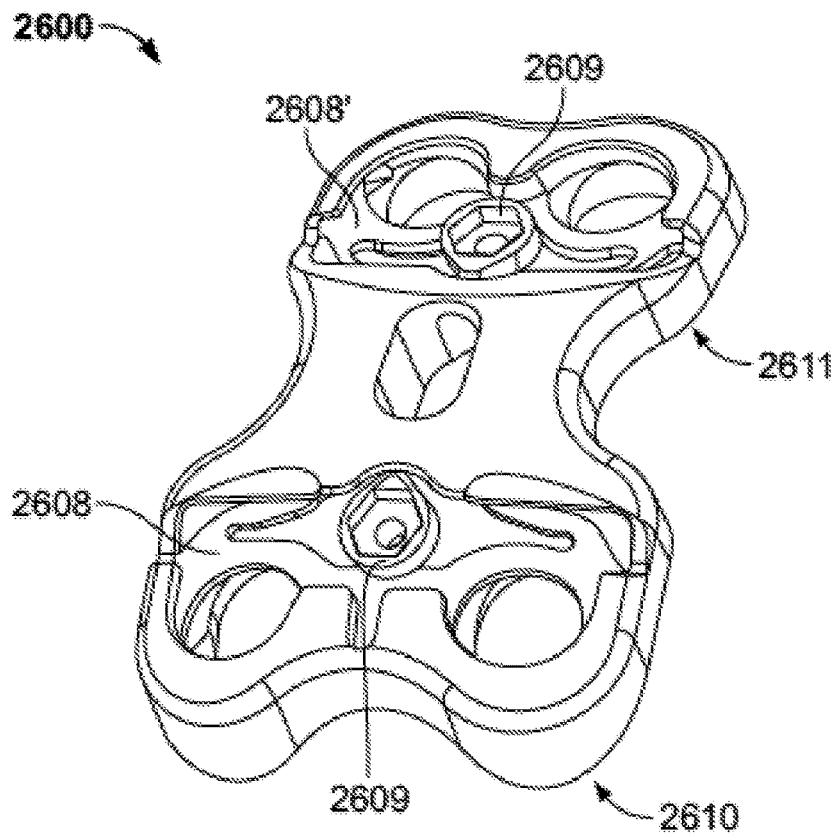
FIGS. 26A and 26B are views of a vertebral plate in accordance with another embodiment of the present invention.
Figure 26B:
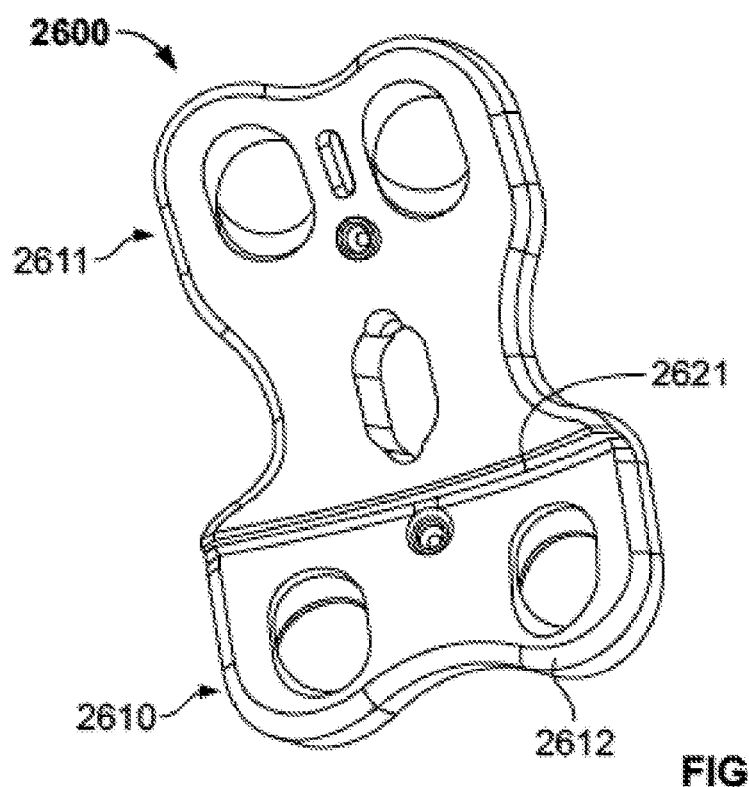

A sacral plate 2600 is shown in FIGS. 26A and 26B and is preferably for use in the lumbar spine, for example, the L5/S1 vertebrae and the disc space therebetween. A caudal (lower) end 2610 has substantially identical features to those of plate 300. A cephalad (upper) end 2611 has a smaller blocker 2608' than both blocker 2608 and blocker 308 of plate 300. Cams 2609 are the same as cams 309 of plate 300. Plate 2600 includes increased curvature compared with plate 300 to accommodate the lumbosacral anatomy (vertebrae L5-S1), though the curvature in the medial direction is substantially the same as that of plate 300. A ledge or ridge 2621 allows plate 2600 to firmly seat on the cortical rim of vertebra S1, for example, while screws are being driven into the bone. The lordotic curvature adjacent the wider portion of plate 2600 is sharper to accommodate the curvature of the S1 vertebra. That curvature terminates with a lip feature 2612 that allows plate 2600 to hug the anterior sacral anatomy. Thus, plate 2600 includes two different lordotic curvatures according to the anatomy.

The cuts on caudal (lower) end 2610 are substantially identical to those on plate 300. Blocker 2608 is the same as blocker 308. Cephalad (upper) end 2611 has a simple radial cut. The upper narrow end 2611 is narrowed to seat beneath the bifurcation of the aorta and vena cava and is configured to prevent or minimize any interaction with that vasculature. The particular geometry and dimensions of plate 2600 still allow for a pair of screws to be provided at cephalad end 2611, and do not require a third screw at caudal end 2610. This allows for cephalad end 2611 to be secured with two screws, whereas some existing plates are configured to provide a less sturdy attachment with only one available screw hole at the upper end of the plate. In one embodiment, the width of cephalad end is approximately 21 mm and the width of caudal end 2610 is approximately 26 mm (which is the same as both ends of plate 300).

The trajectories of the screws defined by the screw holes in caudal end 2610 can converge toward each other due to the medial-lateral curvature of the bottom of plate 2600. In cephalad end 2611, the screw trajectories defined by the screw holes are preferably substantially parallel. There is a medial-lateral curvature of the plate in that area.

Figure 27A:
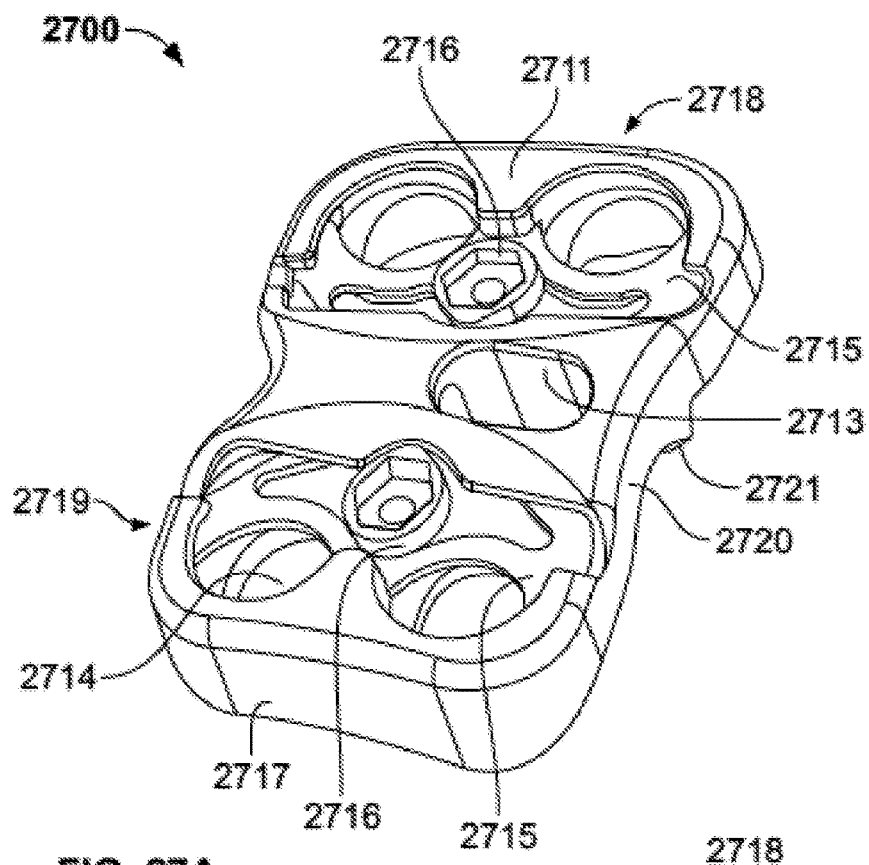
FIGS. 27A and 27B are views of a vertebral plate in accordance with another embodiment of the present invention.
Figure 27B:
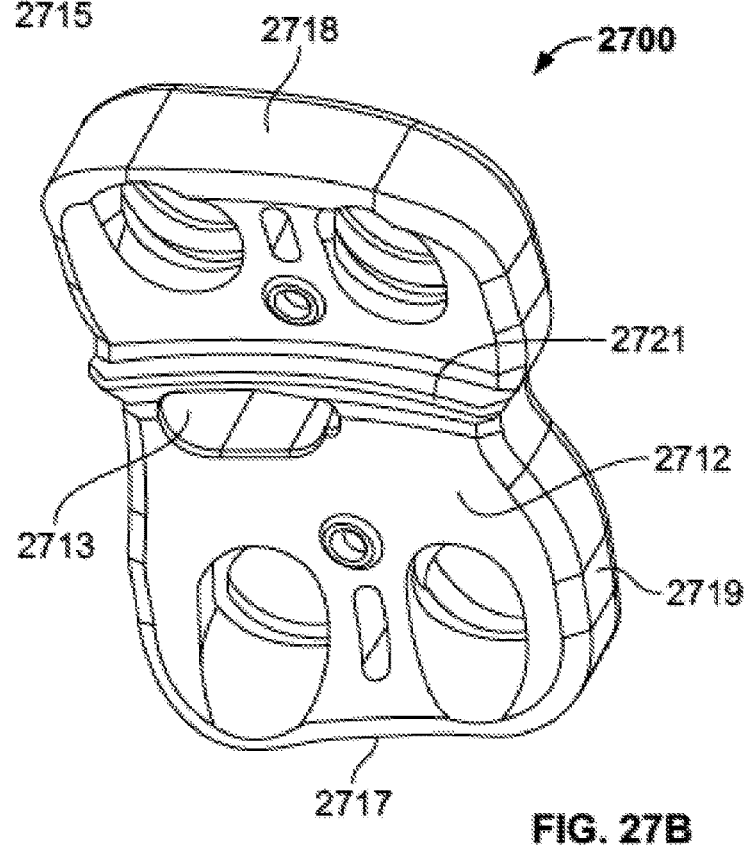

A 4-hole lateral plate 2700 preferably for use in the lumbar region of the spine is shown in FIGS. 27A and 27B. As plate 2700 is configured to fit on the lateral portion of the spine, it can also be inserted via a lateral procedure. Plate 2700 includes a proximal surface 2711, a distal surface 2712, end surfaces 2717 and 2718, side surfaces 2719 and 2720, and a female mating feature 2713 that is located slightly off-center at the proximal surface 2711. A ridge or protrusion 2721 extends distally from distal surface 2712 and may be placed to fit between and/or to abut one or both of the adjacent vertebrae upon implantation of plate 2700. Ridge 2721 is configured such that it can extend across the length of surface 2712. Ridge 2721 may aide in rotating plate 2700 into place, and may also be used in acting as an antirotation feature once plate 2700 is disposed on the bone. Plate 2700 includes a greater curvature at its lateral side to accommodate for the geometry of the vertebrae with which it is attached.

In use, ridge 2721 can be located against the cortical rim of one of the vertebrae adjacent the disc space at which plate 2700 is implanted. Ridge 2721 can therefore provide the surgeon with tactile feedback that plate 2700 is in its implantable position by allowing the surgeon to determine when ridge 2721 is seated against the cortical rim of a vertebra. Ridge 2721 can also be located on plate 2700 in a particular position such that an accurate placement on the exterior surfaces of the vertebrae is facilitated. Ridge 2721 or any other point on plate 2700 can be engaged with the anatomy and utilized as a pivot point for facilitating rotation of plate 2700 during insertion.

Blockers 2715 and cams 2716 are disposed within recesses at proximal surface 2711. Blockers 2715 are utilized to prevent backout of bone screws inserted through the apertures 2714 of plate 2700. Plate 2700 uses the same blocker and features as cephalad (upper) end 2611 of plate 2600, and includes the same cam 2709 as cams 309 and 2609. The backout system provided by blockers 2715 and cams 2716, as well as other aspects of plate 2700, are further disclosed in U.S. patent application Ser. No. 12/291,335, filed on Nov. 7, 2008 and titled "Cervical plate with a feedback device for selective association with bone screw blocking mechanism," the disclosure of which is hereby incorporated by reference herein. The curvature and lip features of plate 2700 accommodate lateral aspects of vertebral bodies (i.e. osteophytes).

Figure 28:
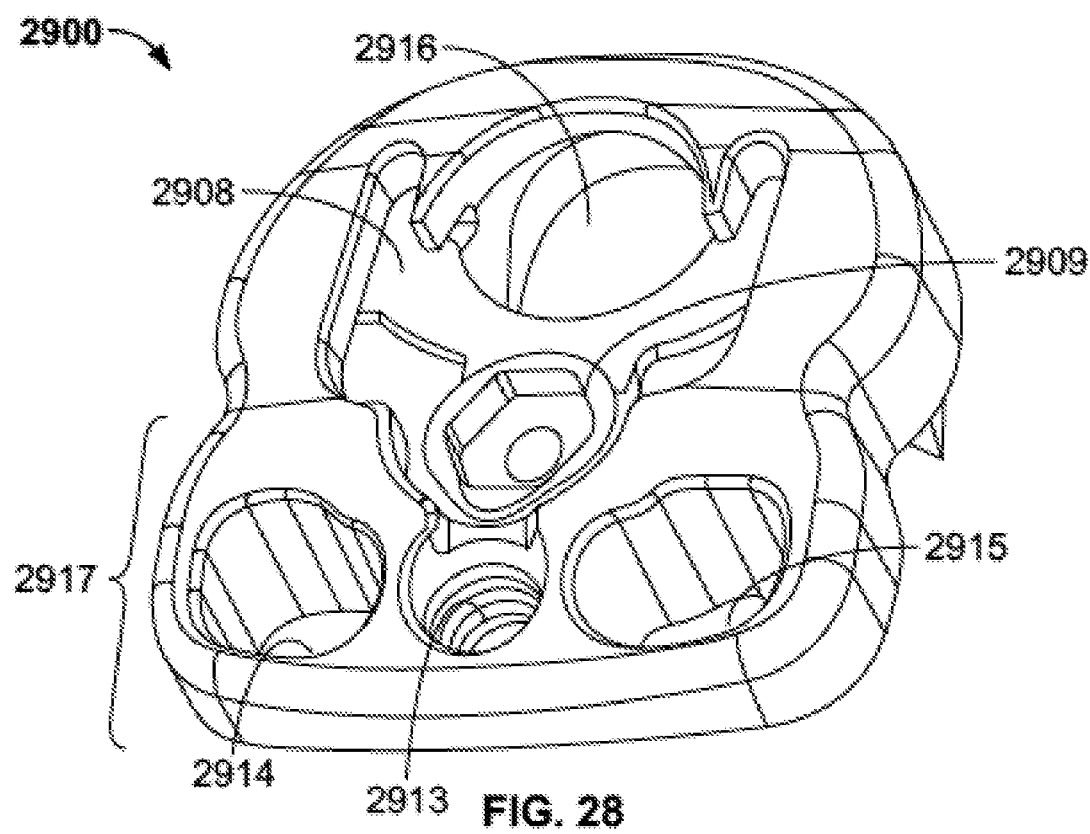
FIGS. 28 and 29 are views of a vertebral plate in accordance with another embodiment of the present invention.
Figure 29:
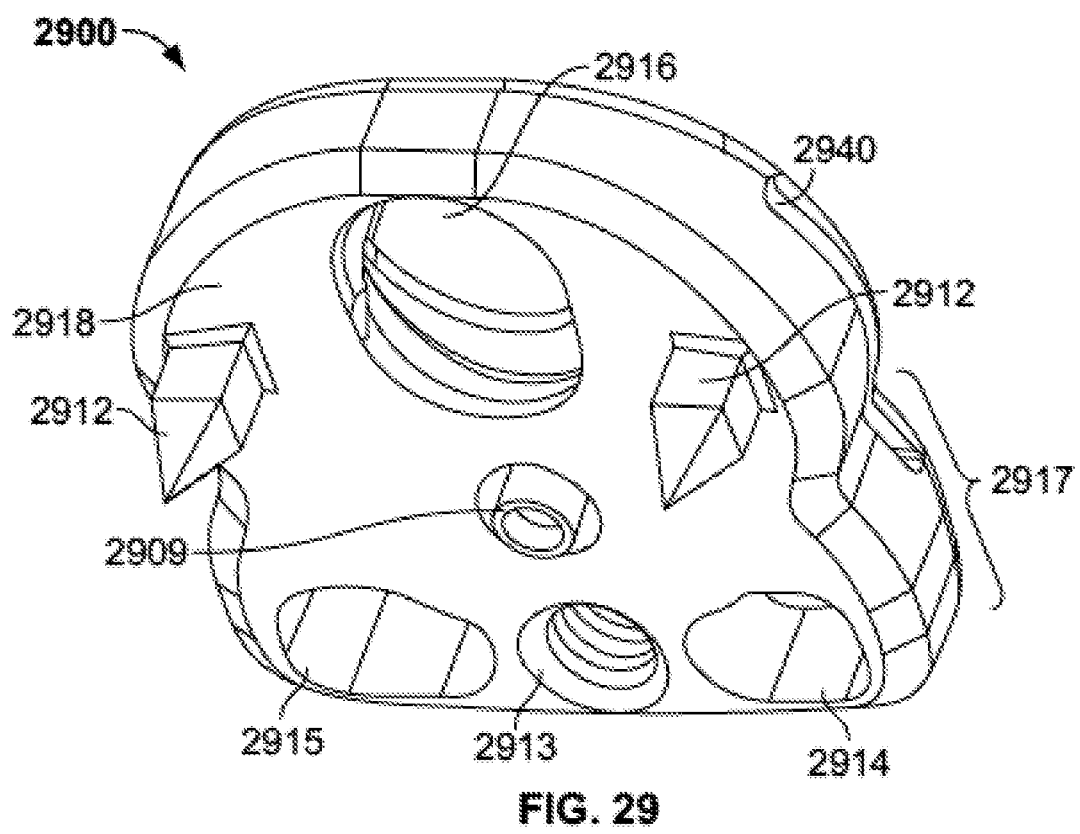

A buttress plate 2900 is shown in FIGS. 28 and 29. Plate 2900 uses a blocker 2908 that is the same as blocker 1308 of plate 1300. Plate 2900 includes the same cam 2909 as cam 309. Cam 2909 protrudes past the bottom surface 2918 of buttress plate 2900, as shown in FIG. 29. The protruding portion of the shaft of cam 2909 can be crimped toward plate 2900 after assembly with buttress plate 2900 to be substantially flush with bottom surface 2918. A channel 2940, similar to channel 2840, is cut through a side of plate 2900. A threaded hole 2913 is provided for engagement with an inserter 3000, described below. Two lateral holes 2914 and 2915 are provided for visibility for the surgeon. Either or both of holes 2914 and 2915 can also be for engagement with a portion of the inserter to prevent rotation between the inserter and plate 2900. Holes 2914 and 2915 can have any geometry including square, circle, oval or other geometries. More or fewer holes like holes 2914 and 2915 can be provided as desired. Of course, a guide and an inserter can be used with plate 2900 in accordance with the description above.

Plate 2900 includes axial curvature to accommodate lumbar anatomy (vertebrae L1-L5). Two spike features 2912 of plate 2900 fix in bone during screw insertion and act as antirotation post implantations. During insertion, plate 2900 can be attached to a single vertebra via a screw through screw hole 2916 and spike features 2912. The lower portion 2917 of plate 2900 can be positioned over or to cover at least a portion of the adjacent vertebral disc space so that an implant previously inserted in the disc space can be substantially prevented from migrating or backing out. Plate 2900 is not necessarily configured to bear a load on the vertebral column, but acts to keep the implant in place while the patient may be moved from a position providing anterior access to the disc space to one providing posterior access to the disc space, which may allow for further screws, rods, implants, etc. to be provided during the procedure.

Inserter 3000 is configured for use with buttress plate 2900 and is shown in FIGS. 30A-30E. Inserter 3000 includes a shaft 3001 having two bends 3002, 3003 that allow a proximal quick connect end 3004 of shaft 3001 to be offset with respect to the distal portion of shaft 3001. Other straight, angled, or curved shafts are contemplated. Proximal quick connect end 3004 can be attached with a handle.

A distal portion 3005 of inserter 3000 is secured to a distal end of shaft 3001 via a pin or screw 3006. Distal portion 3005 includes a distal face 3007 for attachment with buttress plate 2900 and a channel 3008 through which a bone screw can be inserted into buttress plate 2900 and implanted into bone. A threaded set screw 3009 is disposed adjacent distal face 3007 and is assembled onto inserter 3000 through channel 3008 and locked into place with a cross pin or screw 3010. In that way, set screw 3009 can be rotated for engagement with threaded hole 2913 of buttress plate 2900, though rotation of set screw 3009 does not translate set screw 3009 with respect to instrument 3000. A window 3011 provides visibility of the bone screw and set screw 3009 to a surgeon. Two pins 3012 are located at distal face 3007 to engage lateral holes 2914 and 2915 of buttress plate 2900 and to prevent rotation between inserter 3000 and the attached buttress plate 2900.

Figure 30A:
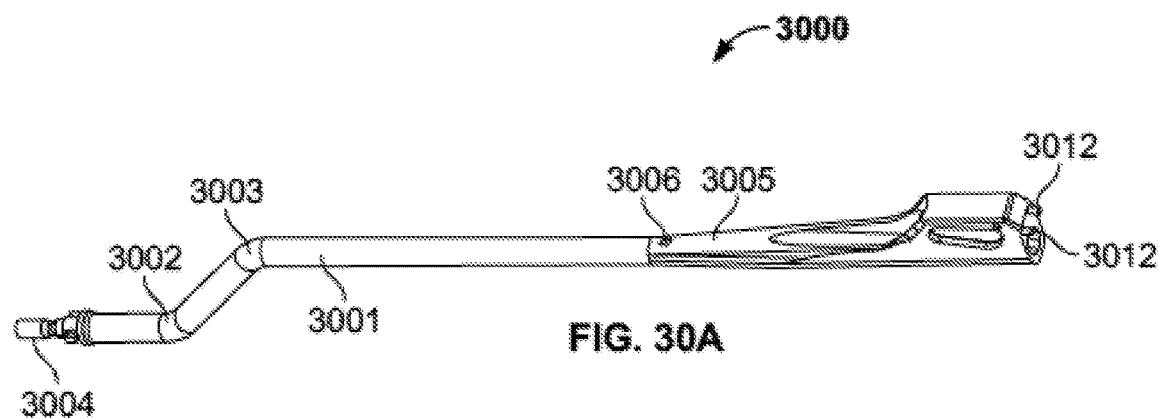
FIGS. 30A-30E are views of an inserter in accordance with another embodiment of the present invention.
Figure 30B:
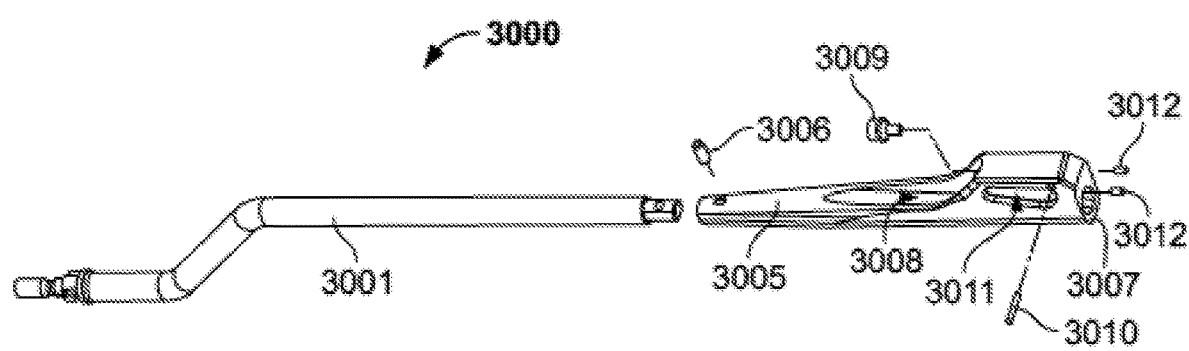
Figure 30C:
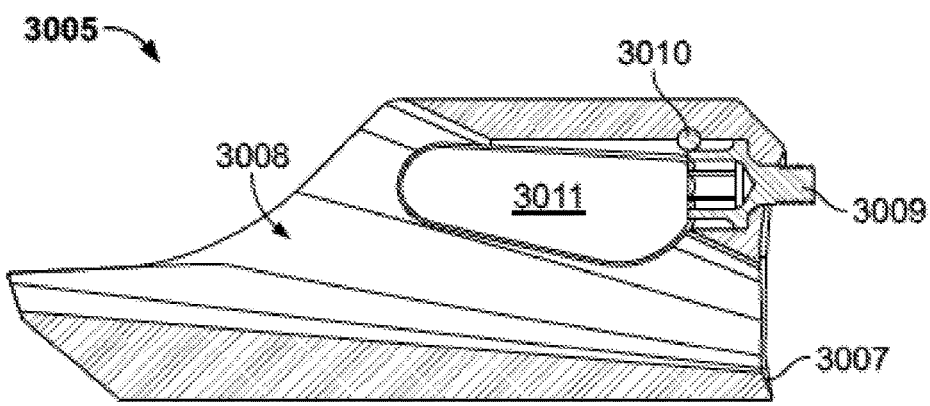
Figure 30D:
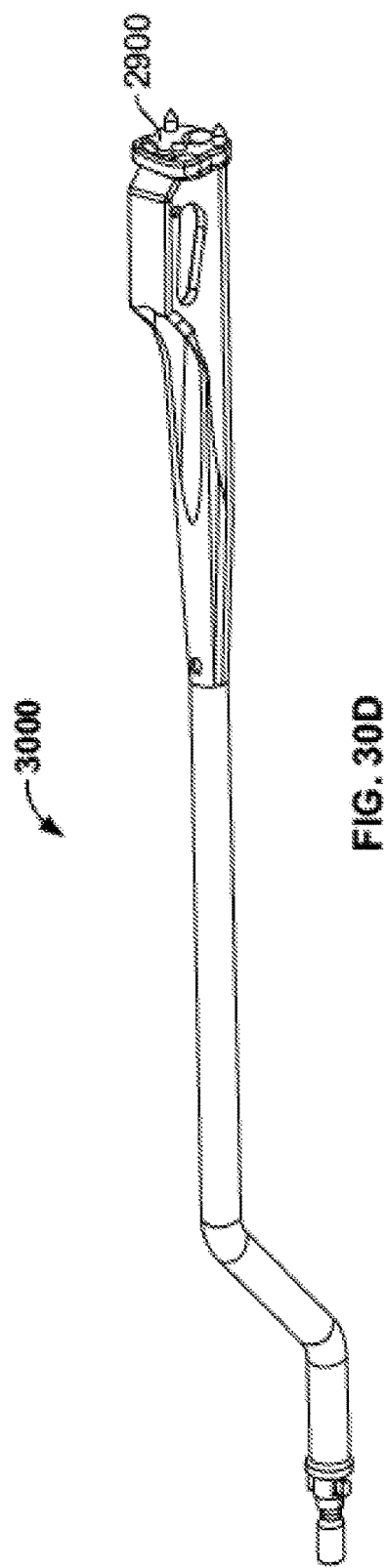
Figure 30E:
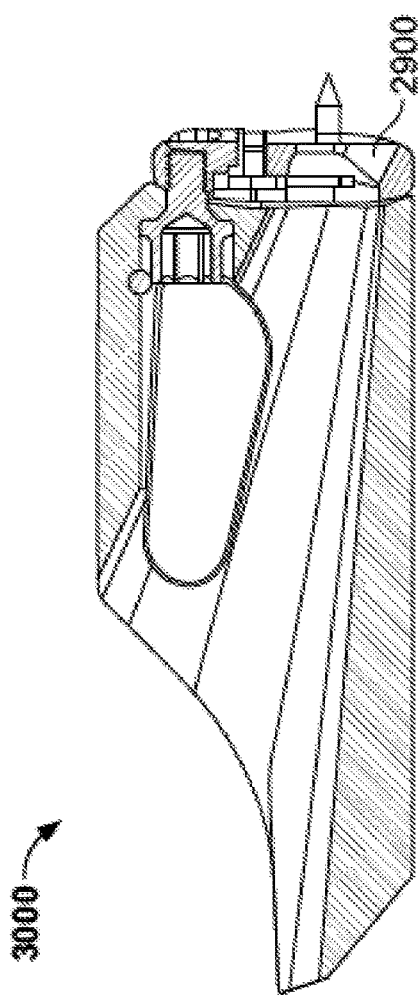

In use, inserter 3000 can be connected with buttress plate 2900 by contacting a top surface of plate 2900 with distal face 3007 in a configuration as shown in FIGS. 30D and 30E. Pins 3012 can be aligned to be located within lateral holes 2914 and 2915. A driver instrument can be used to thread set screw 3009 into threaded hole 2913 of buttress plate 2900 to temporarily secure the engagement between instrument 300 and buttress plate 2900. Instrument can then be used to guide buttress plate 2900 into position adjacent a vertebral body. An impaction force can be provided to instrument 3000 to drive spike features 2912 of buttress plate 2900 into the vertebral body. A bone screw can then be inserted through channel 3008 and screw hole 2916 and into an implant located in the disc space adjacent the vertebral body to which buttress plate 2900 is anchored. The driver instrument can then be used to unthread set screw 3009 from threaded hole 2913, and instrument 3000 can be removed. Buttress plate 2900 will maintain the implant with which it is connected in this location while the patient may be moved to a different position for the implant to be accessed and/or anchored further from a different approach.

The instruments herein described are autoclavable for re-use. The plates described herein may be provided in kits of different sizes. For example, the lateral plates 1300 or 2700 may be provided in lengths of 18-28 mm. Anterior plate 300 may be provided in lengths of 21-37 mm. Sacral plate 2600 may be provided in lengths of 21-37 mm. Of course, other sizes of each of the plates provided herein are contemplated according to patient anatomy and need. Smaller plates in these ranges may have slightly different features, such as female mating feature 303 of plate 300 being oriented differently (i.e. horizontally) on the plate 300 to preserve its size on the smaller overall plate.

A hex-head screw can be provided for use with any or all of the aforementioned plates. Such screws, for example screws 400, can have a hexagonal recess for mating with a complimentary driver, and also a threaded recess for engagement with a removal instrument. Some screws may be provided with a double helical thread for cortical and cancelous bone. Certain screws that can be used with any of the aforementioned plates are those used in connection with the Xia product of Stryker Spine.

In accordance with an embodiment of the invention, multiple plates can be provided together in a kit, with each of those plates provided in multiple sizes. For example, an anterior vertebral plate kit can include one or more universal anterior vertebral plates 300, one or more sacral anterior vertebral plates 2600, and one or more buttress anterior vertebral plates 2900. Multiple sizes of each of plates 300, 2600, and 2900 can be provided so that the surgeon can choose the most appropriate plate for the patient. At least one screw can be provided in the kit for use with the plates. Instrumentation can also be provided for insertion of the plates and screws, in accordance with the instrumentation disclosed above.

In another example, a lateral vertebral plate kit can include one or more lateral vertebral plates 2700 having four screw holes, and one or more lateral vertebral plates 1300 having two screw holes. At least one screw can be provided in the kit, and instrumentation for insertion of the plates and screws can also be provided.

Further to the instrumentation described above, an instrument kit can include a first insertion instrument including an inserter and a guide, and a second insertion instrument directly engageable with the implant.

Larger systems can be provided including multiple of these kits. One system can include the anterior vertebral plate kit and the instrument kit. Another system can include the lateral vertebral plate kit and the instrument kit. A third system can include the anterior vertebral plate kit, the lateral vertebral plate kit, and the instrument kit. In this way, a surgeon can be provided with different components of the system herein described according to need.

Figure 33:
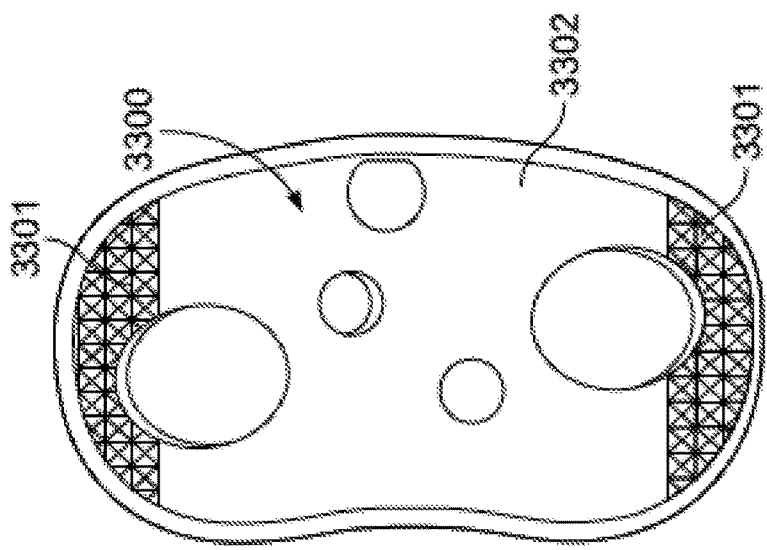
FIGS. 31-33 are views of vertebral plates in accordance with other embodiments of the present invention.
Figure 32:
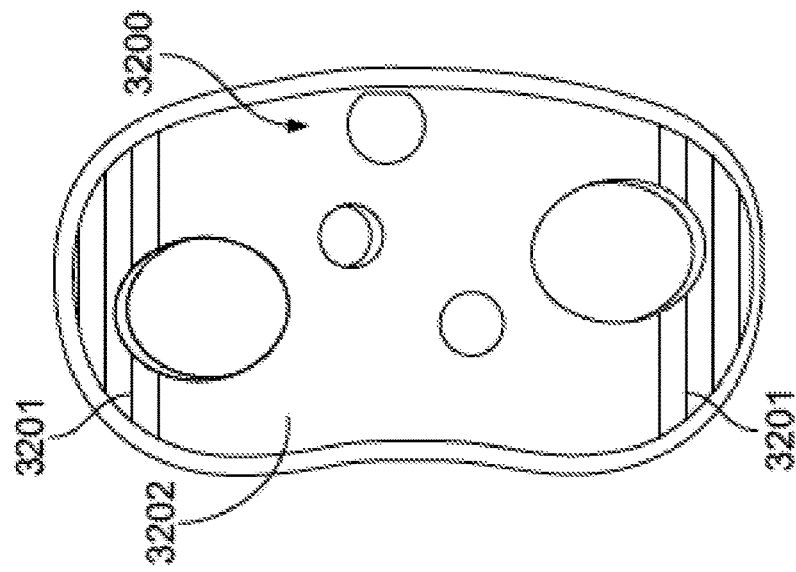
Figure 31:
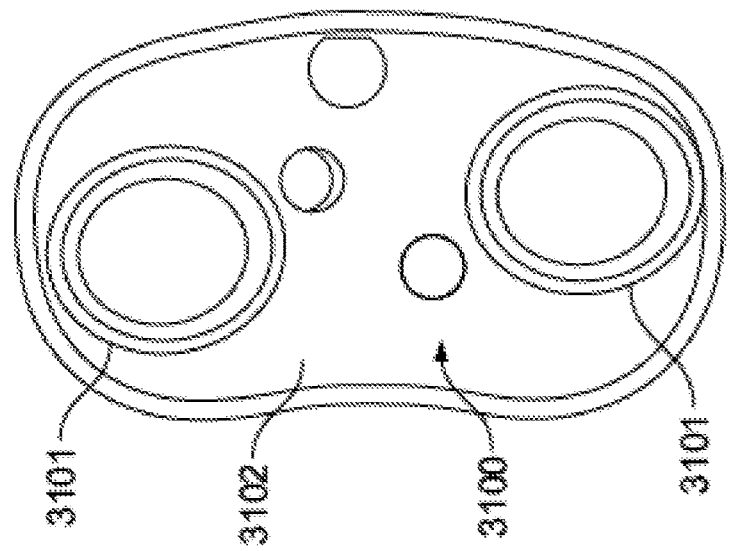

Plates 3100, 3200, and 3300 are shown in FIGS. 31-33, respectively. Plates 3100, 3200, and 3300 are each similar in nature to lateral plate 1300, though none includes a ridge on a bone contacting surface thereof. Instead, each of plates 3100, 3200, and 3300 each includes a type of surface texturing on its bone contacting surface to aid in fixing the plate onto the Lateral aspects of a vertebral body. These surface texturing allow for a reduced plate profile. Such surface texturing are primarily utilized during a surgical procedure, but can also provide extra fixation after implantation, as well.

In particular, plate 3100 includes an ellipse ring 3101 on bone contacting surface 3102 around a periphery of each screw hole. Plate 3200 provides generally medial-lateral extending cuts or ridges 3201 on bone contacting surface 3202 adjacent each of the superior and inferior ends. Plate 3300 provides pyramid-like cuts or ridges 3301 on bone contacting surface 3302 adjacent each of the superior and inferior ends. Other types of surface texturing or surface features can be provided in place of or in addition to those shown and described above to aid in the implantation process and/or to enhance fixation after implantation. Different types of texturing or features can be provided on a single plate in the areas shown or in different areas to facilitate the above-described benefits.

Figure 34:
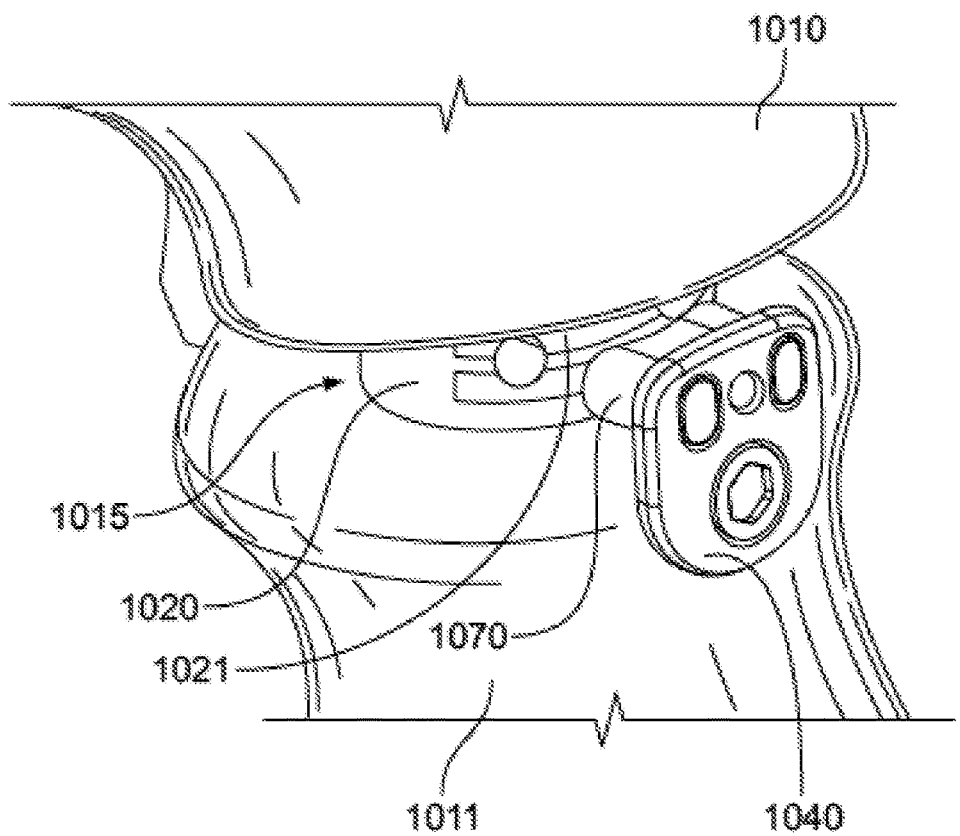
FIGS. 34 and 35 are perspective and side elevational views of a plate and spacer connected with an implant between two vertebral bodies, in accordance with another embodiment of the present invention.
Figure 35:
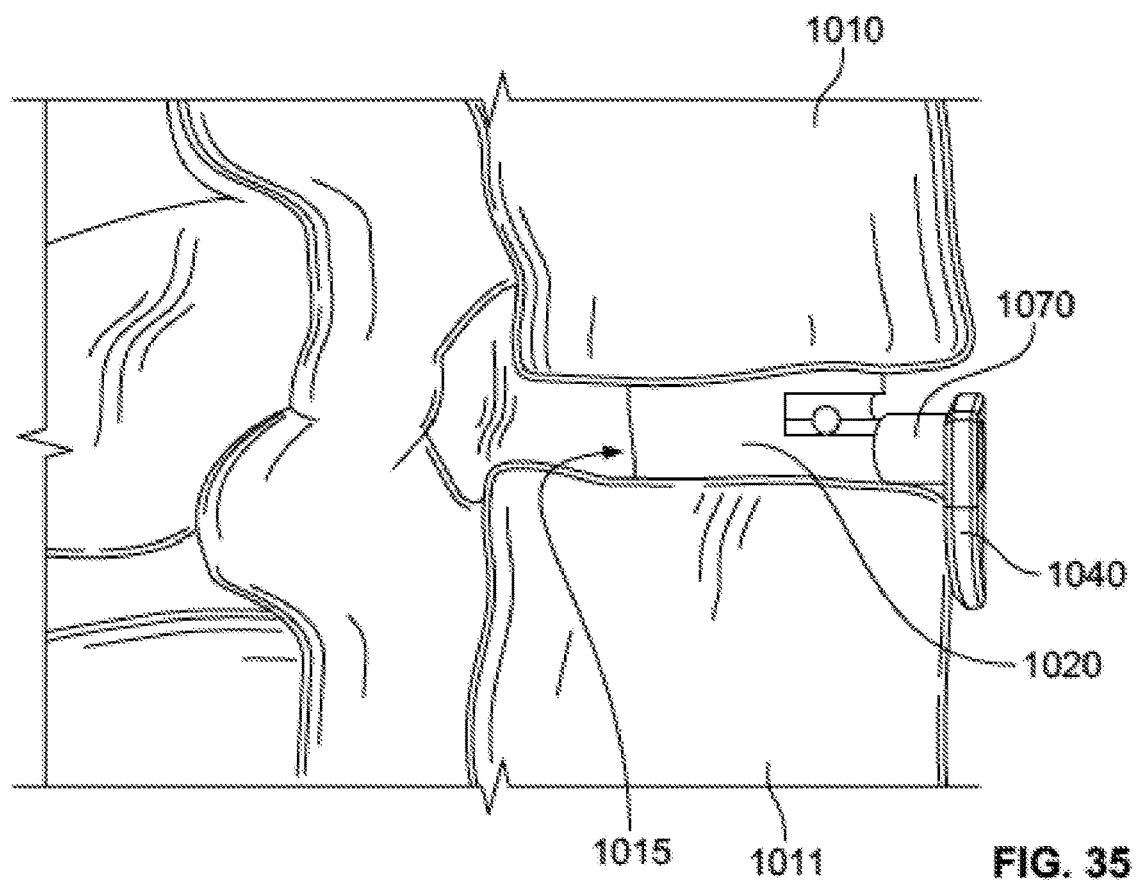

FIGS. 34 and 35 show a spine including a first superior vertebral body 1010, a second inferior vertebral body 1011, and a disc space 1015 located therebetween. Disc material has been removed to allow for the placement of an interbody fusion implant 1020. A buttress plate 1040, similar in nature to buttress plate 2900 described above, is attached to body 1011. It is understood that a spacer of the present invention can be used with either buttress plate 1040 or 2900, or with any other similar buttress plate. A spacer 1070 is coupled to buttress plate 1040 and is also in contact with an anterior aspect 1021 of implant 1020. As shown, anterior aspect 1021 has a rounded or curved geometry.

Figure 36:
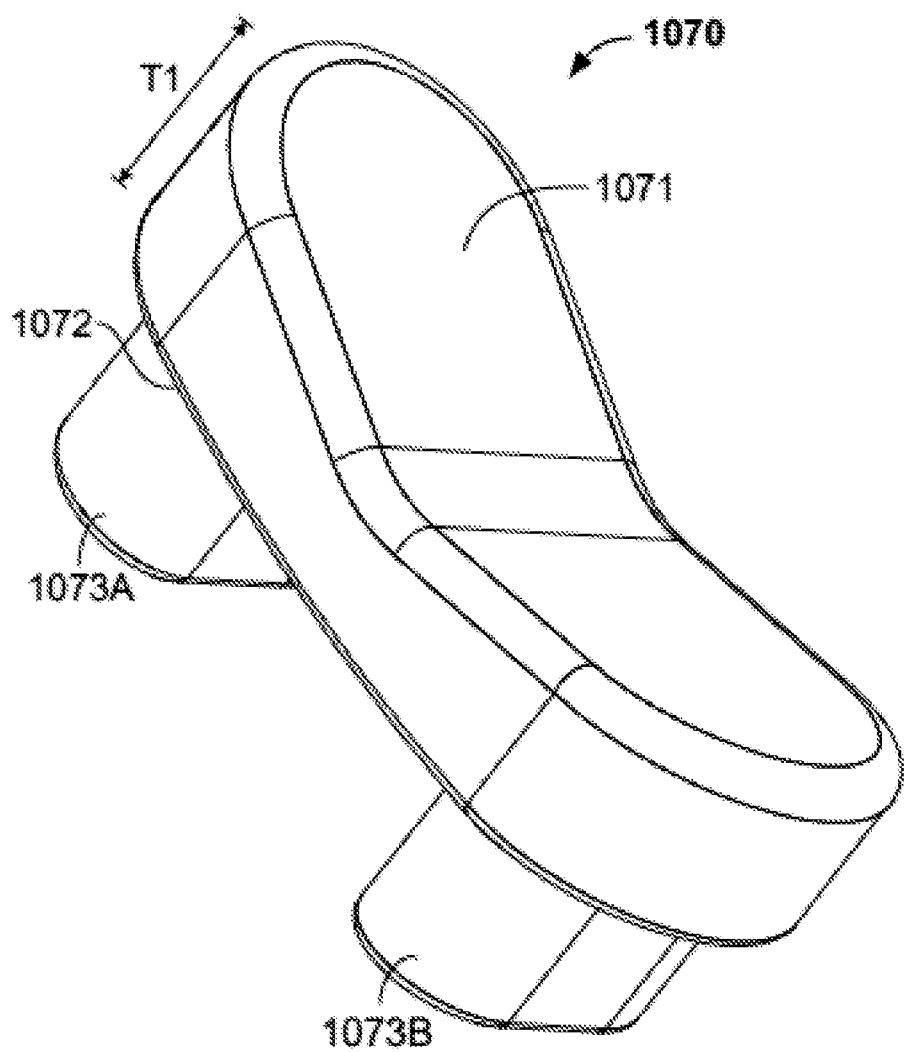
FIGS. 36 and 37 are perspective views of spacers in accordance with the invention shown in FIGS. 34 and 35.

As shown in FIG. 36, spacer 1070 has an implant contacting surface 1071, a plate contacting surface 1072 and two engagement members 1073A and 1073B. Members 1073A and 1073B each extend a certain distance from surface 1072 and are designed to interface with corresponding features, such as apertures, of plate 1040. Such apertures can be, for example, holes 2914 and 2915 of plate 2900 described above. Members 1073A and 1073B are substantially oval in cross-section and extend in a perpendicular direction from surface 1072. Further, the oval shape is designed to have a "press-fit" engagement with the corresponding apertures in plate 1040, such that when spacer 1070 is assembled with plate 1040, force would be required to disassemble one from the other. In alternate embodiments, the cross-sectional shape of members 1073A and 1073B may be circular, square, rectangular or any other geometry designed to interface with similarly configured apertures in plate 1040. Further, there can be various attachment means between spacer 1070 and plate 1040 including: "press-fit", dovetail locking type geometries, threaded engagement or other known attachment means. There may be one, two, or more engagement members in an embodiment of a spacer in accordance with the present invention.

Surface 1072 is designed to correspond to the profile of plate 1040 such that it is removably connected therewith. Other embodiments of a spacer can be configured to be permanently connected to plate 1040. As shown, surface 1072 is substantially flat, but may be contoured, radiused, or curved in alternate embodiments.

Surface 1071 has a "v-type" geometry. This geometry is designed to engage the rounded surface of implant 1020, which has a rounded anterior aspect 1021. Accordingly, this "v-type" geometry provides the desired amount of contact and also makes spacer 1070 suitable for contacting many differently sized, shaped, and curved implants. In alternate embodiments, surface 1071 may be flat, curved or defined by any other geometry designed to mate with the anterior aspect of an implant.

Spacer 1070 abuts implant 1020 at surface 1071 and does not fixedly connect with implant 1020. That surface contact allows plate 1040 and spacer 1070 to maintain implant 1020 in a desired implanted location or at least to prevent implant 1020 from moving anteriorly from its implanted location. In some embodiments, spacer 1070 may be placed so that it does not directly touch or abut implant 1020 when implanted, but that it prevents implant 1020 from moving anteriorly more than a certain distance, that distance being the space between the surgically positioned implant 1020 and the surgically positioned spacer 1070.

Figure 37:
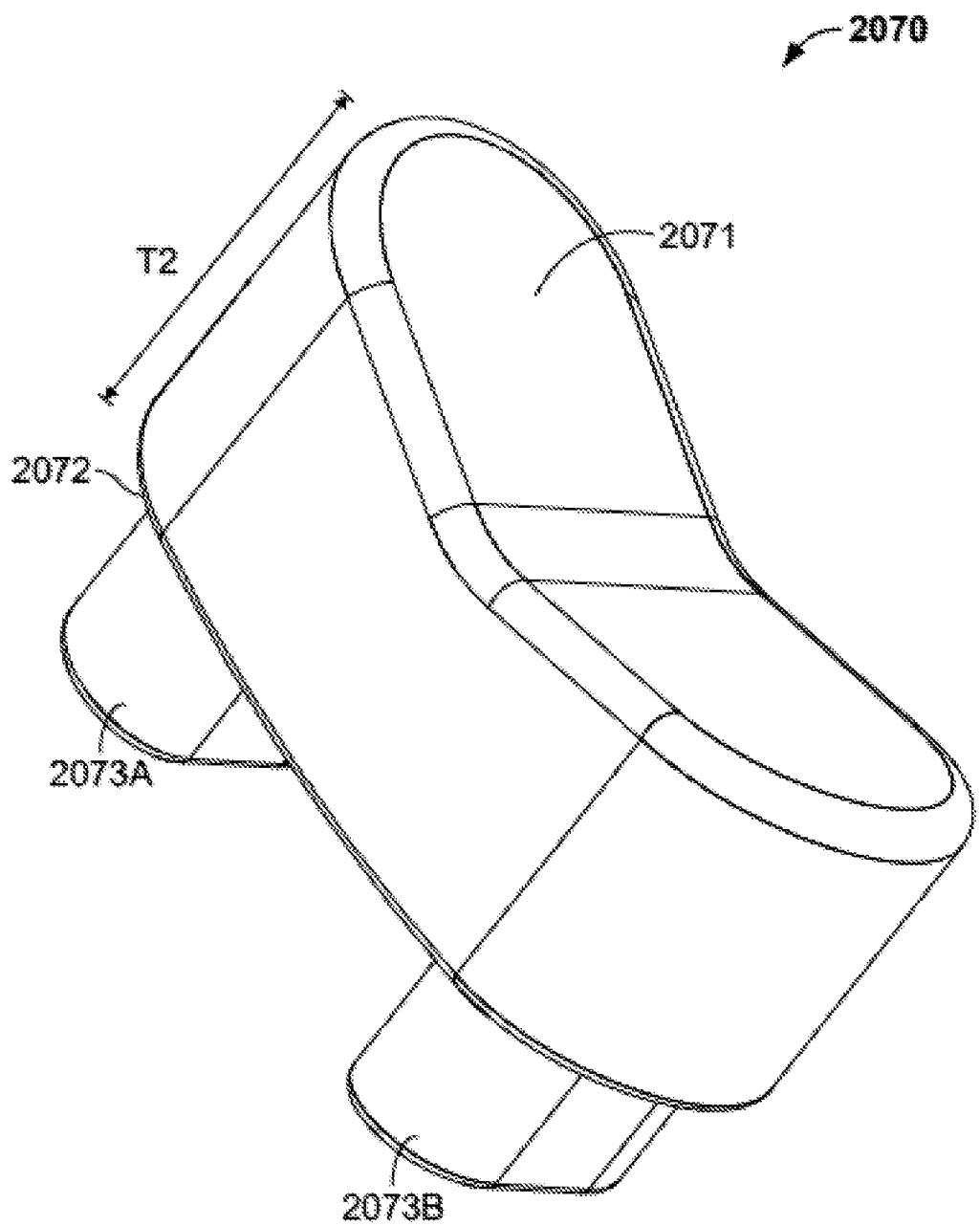

Spacer 1070 may be provided in different thicknesses T1 measured between surfaces 1071 and 1072. For example, a spacer 2070 is shown in FIG. 37 having a thickness T2 greater than thickness T1. A kit can include a set of spacers of various different thicknesses. Other aspects of the set of spacers can be varied in the kit as well, including the number and configuration of members 1073A and 1073B, the material, and the height and width of each spacer in addition to the thickness. This provides a surgeon with great flexibility to set the anterior/posterior placement of the implant 1020. For example, one spacer may have a thickness of 2 mm and another spacer may have a thickness of 5 mm. The thicknesses may change from spacer to spacer in the kit by any increment. For example the thickness may change by 0.5 mm increments from spacer to spacer.

In use, a surgeon can select a spacer 1070 based on the desired thickness, for example, by correlation to the inserter instrument used to place implant 1020. An example of an inserter instrument is described in U.S. Patent Application Publication No. 2009/0048604, titled Insertion Instrument for Intervertebral Implants, the disclosure of which is hereby incorporated herein by reference. With the known depth from the anterior aspect of vertebral bodies 1010 and 1011 at which implant 1020 is or is intended to be located, the surgeon may select an appropriate thickness of a spacer 1070 accordingly. Preferably, spacer 1070 is assembled to plate 1040 and the assembled components are introduced into the body as a single unit.

A spacer according to the present invention may be made of known biocompatible materials such as PEEK, PAEK, polyethelene, bioresorbably plastics, stainless steel, titanium or other known biocompatible materials. A set of spacers having different thicknesses may be presented in the operating room as in a non-sterile tray. Alternately, the spacers may be individually sterile packaged, in which case the surgeon would only need to open a single spacer package per operative level. Another kit can be provided including a set of spacers each configured to operate with a particular plate or set of plates included in the kit. Of course, larger kits can be provided including more iterations of the spacers and plates according to the present inventions. It is also contemplated that spacer 1070 may be attached to other spinal plates such as any of those described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of using a surgical system comprising the steps of:
   removably attaching an inserter to a guide, the guide including a channel extending along a central axis of the guide,
   removably attaching the guide to an implant, the guide having substantially the same footprint as the implant such that when the guide is attached to the implant the guide is substantially aligned with the implant,
   manipulating the inserter to guide the implant, and
   pivoting a proximal end of the inserter with respect to the implant about a rotation axis at a junction between the inserter and the guide to guide the implant into its final positioning, wherein the rotation axis extends transverse to the central axis.

2. The method of claim 1 further comprising inserting a screw through a screw hole of the implant.

3. The method of claim 2, wherein inserting the screw includes inserting the screw through an aperture of the guide aligned with the screw hole of the implant.

4. The method of claim 1, further comprising removing the inserter from the guide with the implant at least temporarily anchored to a vertebra.

5. The method of claim 1, wherein the step of removably attaching the inserter to the guide includes removably attaching two clips of the inserter to pivotally grasp a pin of the guide.

6. The method of claim 5, further comprising moving a sleeve of the inserter from an unlocked position in which the sleeve is disengaged from the clips and the clips can move apart from one another to a locked position in which the sleeve overlaps at least a portion of the clips to at least partially prevent the clips from moving apart from one another.

7. The method of claim 1, further comprising selecting the implant from a group of differently configured implants.

8. The method of claim 1, further comprising inserting a screw through a screw hole of the implant by using a self-retaining screwdriver.

9. The method of claim 1, further comprising inserting a screw through a screw hole of the implant by using a finishing screwdriver.

10. The method of claim 1, further comprising inserting a screw through a screw hole of the implant by using a flexible screwdriver.

11. The method of claim 1, wherein the implant is a vertebral plate configured to engage with an intervertebral implant.

12. A method of using a surgical system comprising the steps of:
- coupling first and second arms of an inserter to a central pin of a guide such that the first and second arms grasp the central pin to removably attach the inserter to the guide, the guide including a channel extending along a central axis of the guide, the pin extending transverse to the central axis and across the channel,
- placing a projection of the guide in a central recess of an implant to removably attach the guide to the implant, the guide having substantially the same footprint as the implant,
- manipulating the inserter to guide the implant, and
- pivoting a proximal end of the inserter with respect to the pin of the guide to position the implant into a target surgical location.

* * * * *